(12) United States Patent
Wyeth et al.

(10) Patent No.: US 12,048,791 B2
(45) Date of Patent: Jul. 30, 2024

(54) PERITONEAL DIALYSIS FLUID PREPARATION AND/OR TREATMENT DEVICES METHODS AND SYSTEMS

(71) Applicant: NxStage Medical, Inc., Lawrence, MA (US)

(72) Inventors: Mark T. Wyeth, Andover, MA (US); Gregory Yantz, Boxford, MA (US); James Ian Johnson, Charlestown, MA (US); James M. Brugger, Newburyport, MA (US); Dennis M. Treu, Castle Rock, CO (US); Dritan Kurshumi, Boston, MA (US); Jeffrey H. Burbank, Manchester, MA (US); William J. Schnell, Libertyville, IL (US); Robert Paul McCarty, Reading, MA (US)

(73) Assignee: NxStage Medical, Inc., Lawrence, MA (US)

( * ) Notice: Subject to any disclaimer, the term of this patent is extended or adjusted under 35 U.S.C. 154(b) by 663 days.

(21) Appl. No.: 16/621,824

(22) PCT Filed: Jun. 24, 2018

(86) PCT No.: PCT/US2018/039188
§ 371 (c)(1),
(2) Date: Dec. 12, 2019

(87) PCT Pub. No.: WO2018/237375
PCT Pub. Date: Dec. 27, 2018

(65) Prior Publication Data
US 2021/0308349 A1    Oct. 7, 2021

Related U.S. Application Data

(60) Provisional application No. 62/524,492, filed on Jun. 24, 2017.

(51) Int. Cl.
*A61M 1/16* (2006.01)
*A61M 1/14* (2006.01)
(Continued)

(52) U.S. Cl.
CPC .......... *A61M 1/1672* (2014.02); *A61M 1/154* (2022.05); *A61M 1/155* (2022.05);
(Continued)

(58) Field of Classification Search
None
See application file for complete search history.

(56) References Cited

U.S. PATENT DOCUMENTS

| 2,369,070 A | 2/1945 | Nielsen |
| 2,575,447 A | 11/1951 | Gossick |

(Continued)

FOREIGN PATENT DOCUMENTS

| CA | 2544144 | 10/2012 |
| CA | 2791816 | 12/2013 |

(Continued)

OTHER PUBLICATIONS

Communication under Rule 71(3) EPC dated Apr. 23, 2020, issued in EP 19 166 992.8.

(Continued)

*Primary Examiner* — Jonathan M Peo
(74) *Attorney, Agent, or Firm* — Potomac Law Group, PLLC

(57) ABSTRACT

Peritoneal dialysis admixing and/or treatment devices, methods, and systems are disclosed. The systems, methods, and devices provide high-level guarantees of sterility and employs relatively inexpensive disposable components to provide pumping. Disclosed systems, methods, and devices and features thereof are adapted for point of use generation of medicament. In particular admixing systems that employ (Continued)

independently-replaceable long term concentrate are disclosed. Features are directed to assurance of sterility and accurate admixing of water and concentrate to generate ready-to-use medicaments and other benefits.

2 Claims, 24 Drawing Sheets

(51) Int. Cl.
*A61M 1/28* (2006.01)
*A61M 39/22* (2006.01)

(52) U.S. Cl.
CPC .......... *A61M 1/156* (2022.05); *A61M 1/1565* (2022.05); *A61M 1/159* (2022.05); *A61M 1/1668* (2014.02); *A61M 1/287* (2013.01); *A61M 39/22* (2013.01); *A61M 2205/3331* (2013.01)

(56) References Cited

U.S. PATENT DOCUMENTS

| | | |
|---|---|---|
| 2,874,351 A | 2/1959 | John |
| 3,490,591 A | 1/1970 | Jones et al. |
| 3,526,834 A | 9/1970 | Brown |
| 3,753,493 A | 8/1973 | Mellor |
| 3,786,810 A | 1/1974 | Pannier et al. |
| 3,847,809 A | 11/1974 | Kopf |
| 3,861,388 A | 1/1975 | Vaughn |
| 3,871,913 A | 3/1975 | Shaldon |
| 3,992,301 A | 11/1976 | Shippey et al. |
| 3,994,293 A | 11/1976 | Ferro |
| 4,138,639 A | 2/1979 | Hutchins |
| 4,158,034 A | 6/1979 | Riede et al. |
| 4,161,264 A | 7/1979 | Malmgren et al. |
| 4,197,848 A | 4/1980 | Garrett et al. |
| 4,209,391 A | 6/1980 | Lipps et al. |
| 4,338,190 A | 7/1982 | Kraus et al. |
| 4,361,485 A | 11/1982 | Boonstra |
| 4,396,382 A | 8/1983 | Goldhaber |
| 4,399,030 A | 8/1983 | Hlavinka et al. |
| 4,412,834 A | 11/1983 | Kulin et al. |
| 4,420,752 A | 12/1983 | Davis et al. |
| 4,432,759 A | 2/1984 | Gross et al. |
| 4,432,765 A | 2/1984 | Oscarsson |
| 4,435,171 A | 3/1984 | Goldberg et al. |
| 4,439,179 A | 3/1984 | Lueders et al. |
| 4,439,188 A | 3/1984 | Dennehey et al. |
| 4,440,207 A | 4/1984 | Genatempo et al. |
| 4,447,230 A | 5/1984 | Gula et al. |
| 4,479,760 A | 10/1984 | Bilstad et al. |
| 4,489,535 A | 12/1984 | Veltman |
| 4,493,705 A | 1/1985 | Gordon et al. |
| 4,526,572 A | 7/1985 | Donnan et al. |
| 4,553,552 A | 11/1985 | Valdespino et al. |
| 4,559,043 A | 12/1985 | Whitehouse et al. |
| 4,585,436 A | 4/1986 | Davis et al. |
| 4,605,895 A | 8/1986 | Park |
| 4,612,170 A | 9/1986 | Luther et al. |
| 4,617,115 A | 10/1986 | Vantard |
| 4,618,343 A | 10/1986 | Polaschegg |
| 4,636,204 A | 1/1987 | Christopherson et al. |
| 4,654,026 A | 3/1987 | Underwood |
| 4,655,742 A | 4/1987 | Vantard |
| 4,657,529 A | 4/1987 | Prince et al. |
| 4,663,006 A | 5/1987 | Yao et al. |
| 4,670,007 A | 6/1987 | Wheeldon et al. |
| 4,673,506 A | 6/1987 | Henne et al. |
| 4,695,385 A | 9/1987 | Boag |
| 4,702,829 A | 10/1987 | Polaschegg et al. |
| 4,747,822 A | 5/1988 | Peabody |
| 4,747,950 A | 5/1988 | Guinn |
| 4,752,292 A | 6/1988 | Lopez et al. |
| 4,797,191 A | 1/1989 | Metzner et al. |
| 4,823,833 A | 4/1989 | Hogan et al. |
| 4,825,168 A | 4/1989 | Ogawa et al. |
| 4,846,950 A | 7/1989 | Yao et al. |
| 4,857,199 A | 8/1989 | Cortial |
| 4,867,739 A | 9/1989 | Kawano |
| 4,871,353 A | 10/1989 | Thomsen |
| 4,876,515 A | 10/1989 | Ball |
| 4,954,782 A | 9/1990 | Ball |
| 4,966,585 A | 10/1990 | Gangemi |
| 4,976,685 A | 12/1990 | Block, Jr. |
| 4,981,469 A | 1/1991 | Whitehouse et al. |
| 4,997,570 A | 3/1991 | Polaschegg |
| 5,004,535 A | 4/1991 | Bosko et al. |
| 5,061,365 A | 10/1991 | Utterberg |
| 5,062,774 A | 11/1991 | Kramer et al. |
| 5,071,413 A | 12/1991 | Utterberg |
| 5,078,699 A | 1/1992 | Haber et al. |
| 5,087,245 A | 2/1992 | Doan |
| 5,139,483 A | 8/1992 | Ryan |
| 5,139,675 A | 8/1992 | Arnold et al. |
| 5,141,493 A | 8/1992 | Jacobsen et al. |
| 5,203,771 A | 4/1993 | Melker et al. |
| 5,209,800 A * | 5/1993 | Spencer ................ B29C 66/80 156/304.6 |
| 5,224,932 A | 7/1993 | Lappas |
| 5,225,783 A | 7/1993 | Suzuki et al. |
| 5,242,392 A | 9/1993 | Vaughn |
| 5,256,371 A | 10/1993 | Pippert |
| 5,268,144 A | 12/1993 | Heilmann et al. |
| 5,326,476 A | 7/1994 | Grogan et al. |
| 5,330,425 A | 7/1994 | Utterberg |
| 5,336,173 A | 8/1994 | Folden |
| 5,344,392 A | 9/1994 | Senninger et al. |
| 5,344,568 A | 9/1994 | Kitaevich et al. |
| 5,346,472 A | 9/1994 | Keshaviah et al. |
| 5,360,395 A | 11/1994 | Utterberg |
| 5,442,969 A | 8/1995 | Troutner et al. |
| 5,484,397 A | 1/1996 | Twardowski |
| 5,485,083 A | 1/1996 | Pulice |
| 5,486,286 A | 1/1996 | Peterson et al. |
| 5,490,925 A | 2/1996 | Eigendorf |
| 5,522,998 A | 6/1996 | Polaschegg |
| 5,567,320 A | 10/1996 | Goux et al. |
| 5,570,026 A | 10/1996 | Buffaloe, IV et al. |
| 5,589,070 A | 12/1996 | Maltais et al. |
| 5,591,344 A | 1/1997 | Kenley et al. |
| 5,603,902 A | 2/1997 | Maltais et al. |
| 5,628,908 A | 5/1997 | Kamen et al. |
| 5,631,552 A | 5/1997 | Ogawa et al. |
| 5,650,071 A | 7/1997 | Brugger et al. |
| 5,651,893 A | 7/1997 | Kenley et al. |
| 5,674,390 A | 10/1997 | Matthews et al. |
| 5,725,773 A | 3/1998 | Polaschegg |
| 5,800,383 A | 9/1998 | Chandler et al. |
| 5,836,933 A | 11/1998 | Buttitta et al. |
| 5,865,764 A | 2/1999 | Moorhead |
| 5,895,578 A | 4/1999 | Simard et al. |
| 5,900,136 A | 5/1999 | Gotsu et al. |
| 5,925,011 A | 7/1999 | Faict et al. |
| 5,932,110 A | 8/1999 | Shah et al. |
| 5,938,634 A | 8/1999 | Packard |
| 5,945,449 A | 8/1999 | Purcell et al. |
| 6,036,680 A | 3/2000 | Horne et al. |
| 6,110,384 A | 8/2000 | Goux et al. |
| 6,129,699 A | 10/2000 | Haight et al. |
| 6,136,201 A | 10/2000 | Shah et al. |
| 6,139,754 A | 10/2000 | Hartranft et al. |
| 6,156,797 A | 12/2000 | Kubo et al. |
| 6,168,578 B1 | 1/2001 | Diamond |
| 6,196,991 B1 | 3/2001 | Keilman |
| 6,228,047 B1 | 5/2001 | Dadson |
| 6,241,943 B1 | 6/2001 | Wieslander et al. |
| 6,254,567 B1 | 7/2001 | Treu et al. |
| 6,270,673 B1 | 8/2001 | Belt et al. |
| 6,280,634 B1 | 8/2001 | Shah et al. |
| 6,327,895 B1 | 12/2001 | Jeppsson et al. |
| 6,391,404 B1 | 5/2002 | Rosenbaum et al. |
| 6,409,699 B1 | 6/2002 | Ash |
| 6,423,029 B1 | 7/2002 | Elsberry |

(56) References Cited

U.S. PATENT DOCUMENTS

| | | |
|---|---|---|
| 6,460,592 B1 | 10/2002 | Sano et al. |
| 6,463,979 B1 | 10/2002 | Sano et al. |
| 6,471,855 B1 | 10/2002 | Odak et al. |
| 6,488,647 B1 | 12/2002 | Miura et al. |
| 6,489,785 B2 | 12/2002 | McAllister |
| 6,491,658 B1 | 12/2002 | Miura et al. |
| 6,492,336 B1 | 12/2002 | Mahiout |
| 6,503,062 B1 | 1/2003 | Gray et al. |
| 6,537,976 B1 | 3/2003 | Gupta |
| 6,585,682 B1 | 7/2003 | Haraldsson et al. |
| 6,591,126 B2 | 7/2003 | Roeper et al. |
| 6,595,948 B2 | 7/2003 | Suzuki et al. |
| 6,605,214 B1 | 8/2003 | Taylor |
| 6,610,206 B1 | 8/2003 | Callan et al. |
| 6,626,862 B1 | 9/2003 | Duchon et al. |
| 6,645,191 B1 | 11/2003 | Knerr et al. |
| 6,648,906 B2 | 11/2003 | Lasheras et al. |
| 6,666,842 B1 | 12/2003 | Sakai |
| 6,689,275 B1 | 2/2004 | Gupta |
| 6,705,372 B2 | 3/2004 | Sano et al. |
| 6,738,052 B1 | 5/2004 | Manke et al. |
| 6,749,580 B2 | 6/2004 | Work et al. |
| 6,758,975 B2 | 7/2004 | Peabody et al. |
| 6,769,231 B2 | 8/2004 | Danby |
| 6,803,363 B2 | 10/2004 | Polaschegg |
| 6,808,369 B2 | 10/2004 | Gray et al. |
| 6,814,869 B2 | 11/2004 | Brandl et al. |
| 6,861,033 B2 | 3/2005 | Mullins et al. |
| 6,877,713 B1 | 4/2005 | Gray et al. |
| 6,887,214 B1 | 5/2005 | Levin |
| 6,889,713 B2 | 5/2005 | Navis |
| 6,911,014 B2 | 6/2005 | Wentling et al. |
| 6,912,917 B2 | 7/2005 | Brugger et al. |
| 6,929,751 B2 | 8/2005 | Bowman et al. |
| 6,981,977 B2 | 1/2006 | Herweck et al. |
| 6,986,752 B2 | 1/2006 | McGuckin et al. |
| 6,995,563 B2 | 2/2006 | Talutis |
| 7,013,928 B2 | 3/2006 | Navis |
| 7,033,539 B2 | 4/2006 | Krensky et al. |
| 7,053,059 B2 | 5/2006 | Zieske et al. |
| 7,057,400 B2 | 6/2006 | Gaignet |
| 7,067,061 B2 | 6/2006 | Bosetto et al. |
| 7,083,719 B2 | 8/2006 | Bowman et al. |
| 7,119,305 B2 | 10/2006 | Sano et al. |
| 7,138,088 B2 | 11/2006 | Wariar et al. |
| 7,175,606 B2 | 2/2007 | Bowman, Jr. et al. |
| 7,214,228 B2 | 5/2007 | Crabtree |
| 7,235,589 B2 | 6/2007 | Hausheer |
| 7,243,893 B2 | 7/2007 | Sobue et al. |
| 7,250,619 B2 | 7/2007 | Taylor et al. |
| 7,320,676 B2 | 1/2008 | Miesel |
| 7,354,190 B2 | 4/2008 | Demers et al. |
| 7,410,475 B2 | 8/2008 | Krensky et al. |
| 7,421,316 B2 | 9/2008 | Gray et al. |
| 7,441,108 B2 | 10/2008 | Fisher et al. |
| 7,459,054 B2 | 12/2008 | Landherr et al. |
| 7,544,301 B2 | 6/2009 | Shah et al. |
| 7,559,483 B2 | 7/2009 | Hickle et al. |
| 7,559,524 B2 | 7/2009 | Gray et al. |
| 7,559,913 B1 | 7/2009 | Jeppsson et al. |
| 7,641,753 B2 | 1/2010 | Gao et al. |
| 7,670,491 B2 | 3/2010 | Callan et al. |
| 7,686,279 B2 | 3/2010 | Nerbonne et al. |
| 7,758,552 B2 | 7/2010 | Zoltan et al. |
| 7,763,013 B2 | 7/2010 | Baldwin et al. |
| 7,803,628 B2 | 9/2010 | Glocker |
| 7,837,666 B2 | 11/2010 | Jensen et al. |
| 7,842,002 B2 | 11/2010 | Mantle |
| 7,847,564 B2 | 12/2010 | Rossi |
| 7,857,805 B2 | 12/2010 | Raines |
| 7,862,530 B2 | 1/2011 | Callan et al. |
| 7,867,214 B2 | 1/2011 | Childers et al. |
| 7,883,725 B2 | 2/2011 | Shah et al. |
| 7,892,423 B2 | 2/2011 | Rohde et al. |
| 7,901,376 B2 | 3/2011 | Steck et al. |
| 7,905,853 B2 | 3/2011 | Chapman et al. |
| 7,905,855 B2 | 3/2011 | Childers |
| 7,935,074 B2 | 5/2011 | Plahey et al. |
| 7,955,295 B2 | 6/2011 | Lee et al. |
| 7,988,849 B2 | 8/2011 | Biewer et al. |
| 7,993,050 B2 | 8/2011 | Demers et al. |
| 8,034,017 B2 | 10/2011 | Petersen |
| 8,083,709 B2 | 12/2011 | Childers et al. |
| 8,088,094 B2 | 1/2012 | Hamada et al. |
| 8,096,969 B2 | 1/2012 | Roberts et al. |
| 8,105,487 B2 | 1/2012 | Fulkerson et al. |
| 8,147,696 B1 | 4/2012 | Pandya |
| 8,178,040 B2 | 5/2012 | Brauer |
| 8,202,547 B2 | 6/2012 | Shah et al. |
| 8,222,229 B2 | 7/2012 | Kiribayashi et al. |
| 8,246,826 B2 | 8/2012 | Wilt et al. |
| 8,287,724 B2 | 10/2012 | Slepicka et al. |
| 8,297,954 B2 | 10/2012 | Moubayed |
| 8,298,167 B2 | 10/2012 | Peters et al. |
| 8,298,170 B2 | 10/2012 | Lundtveit et al. |
| 8,308,128 B2 | 11/2012 | Mackal |
| 8,348,904 B2 | 1/2013 | Petersen |
| 8,361,009 B2 | 1/2013 | Lee et al. |
| 8,367,731 B2 | 2/2013 | Wieslander et al. |
| 8,375,797 B2 | 2/2013 | Beden et al. |
| 8,382,447 B2 | 2/2013 | Wang et al. |
| 8,393,690 B2 | 3/2013 | Grant et al. |
| 8,398,590 B2 | 3/2013 | Sternberg et al. |
| 8,414,686 B2 | 4/2013 | Gura et al. |
| 8,414,768 B2 | 4/2013 | Shah et al. |
| 8,431,086 B2 | 4/2013 | Lurvey et al. |
| 8,444,593 B2 | 5/2013 | Hamada et al. |
| 8,449,496 B2 | 5/2013 | Tamada et al. |
| 8,460,544 B2 | 6/2013 | Völker |
| 8,474,784 B2 | 7/2013 | Kashmirian et al. |
| 8,491,184 B2 | 7/2013 | Kamen et al. |
| 8,500,676 B2 | 8/2013 | Jansson et al. |
| 8,501,009 B2 | 8/2013 | Peterson et al. |
| 8,516,902 B2 | 8/2013 | Beavis et al. |
| 8,529,496 B2 | 9/2013 | Britton et al. |
| 8,540,886 B2 | 9/2013 | Hedmann et al. |
| 8,556,225 B2 | 10/2013 | Gray |
| 8,560,510 B2 | 10/2013 | Brueggerhoff et al. |
| 8,587,516 B2 | 11/2013 | Kopychev et al. |
| 8,597,229 B2 | 12/2013 | Pan |
| 8,600,772 B2 | 12/2013 | Bacon |
| 8,613,739 B2 | 12/2013 | Sobue |
| 8,641,685 B2 | 2/2014 | Mansour et al. |
| 8,671,996 B2 | 3/2014 | Weilhoefer et al. |
| 8,678,224 B2 | 3/2014 | D'Ayot et al. |
| 8,685,251 B2 | 4/2014 | Smejtek et al. |
| 8,698,741 B1 | 4/2014 | Wang et al. |
| 8,708,992 B2 | 4/2014 | Kobayashi et al. |
| 8,728,056 B2 | 5/2014 | Colantonio et al. |
| 8,731,726 B2 | 5/2014 | Gray et al. |
| 8,740,864 B2 | 6/2014 | Hoang et al. |
| 8,741,131 B2 | 6/2014 | Bedingfield et al. |
| 8,747,370 B2 | 6/2014 | Feith et al. |
| 8,758,626 B2 | 6/2014 | Wong |
| 8,764,702 B2 | 7/2014 | Childers et al. |
| 8,774,885 B2 | 7/2014 | Abreu |
| 8,777,892 B2 | 7/2014 | Sandford et al. |
| 8,789,558 B2 | 7/2014 | Volker |
| 8,801,652 B2 | 8/2014 | Landherr et al. |
| 8,801,677 B2 | 8/2014 | Wallin |
| 8,808,595 B2 | 8/2014 | Babrowicz et al. |
| 8,813,769 B2 | 8/2014 | Gastauer et al. |
| 8,815,095 B2 | 8/2014 | Micheli |
| 8,828,232 B2 | 9/2014 | Shah et al. |
| 8,834,718 B2 | 9/2014 | Randall et al. |
| 8,834,719 B2 | 9/2014 | Childers et al. |
| 8,838,395 B2 | 9/2014 | Matsiev et al. |
| 8,840,581 B2 | 9/2014 | McGill et al. |
| 8,858,792 B2 | 10/2014 | Ding et al. |
| 8,869,612 B2 | 10/2014 | Chen et al. |
| 8,870,812 B2 | 10/2014 | Alberti et al. |
| 8,875,748 B2 | 11/2014 | Beden et al. |
| 8,876,753 B2 | 11/2014 | Roberts et al. |
| 8,882,700 B2 | 11/2014 | Chapman et al. |

(56) References Cited

U.S. PATENT DOCUMENTS

| | | |
|---|---|---|
| 8,924,458 B2 | 12/2014 | Levin et al. |
| 8,926,550 B2 | 1/2015 | Plahey et al. |
| 8,926,551 B2 | 1/2015 | Lo et al. |
| 8,930,213 B2 | 1/2015 | Gotlib et al. |
| 8,945,042 B2 | 2/2015 | Lee et al. |
| 8,961,444 B2 | 2/2015 | Chapman et al. |
| 8,961,466 B2 | 2/2015 | Steinbach |
| 8,980,070 B2 | 3/2015 | Nishio et al. |
| 8,989,906 B2 | 3/2015 | Gray et al. |
| 8,992,454 B2 | 3/2015 | Anand |
| 8,992,777 B2 | 3/2015 | Doyle |
| 9,004,886 B2 | 4/2015 | Beck et al. |
| 9,014,775 B2 | 4/2015 | Bennett et al. |
| 9,022,969 B2 | 5/2015 | Helmore et al. |
| 9,044,544 B2 | 6/2015 | Lo et al. |
| 9,060,727 B2 | 6/2015 | Saikley et al. |
| 9,066,968 B2 | 6/2015 | Ohta et al. |
| 9,067,017 B2 | 6/2015 | Tan et al. |
| 9,069,886 B2 | 6/2015 | Shimizu et al. |
| 9,108,031 B2 | 8/2015 | Brandenburger et al. |
| 9,112,245 B2 | 8/2015 | Yen |
| 9,132,220 B2 | 9/2015 | Kugelmann et al. |
| 9,138,523 B2 | 9/2015 | Burnett et al. |
| 9,152,918 B1 | 10/2015 | McNair |
| 9,153,002 B2 | 10/2015 | Jones et al. |
| 9,162,044 B2 | 10/2015 | Traversaz |
| 9,165,112 B2 | 10/2015 | Doyle et al. |
| 9,180,238 B2 | 11/2015 | Bedingfield et al. |
| 9,198,830 B2 | 12/2015 | Kugelmann et al. |
| 9,199,070 B2 | 12/2015 | Wegener et al. |
| 9,216,247 B2 | 12/2015 | Callan et al. |
| 9,217,702 B2 | 12/2015 | Sullivan |
| 9,242,035 B2 | 1/2016 | Karoor |
| 9,254,356 B2 | 2/2016 | Shah et al. |
| 9,254,358 B2 | 2/2016 | Volker |
| 9,274,073 B2 | 3/2016 | Nier et al. |
| 9,284,960 B2 | 3/2016 | Chappel et al. |
| 9,308,309 B2 | 4/2016 | Hedmann et al. |
| 9,310,232 B2 | 4/2016 | Heide et al. |
| 9,319,110 B2 | 4/2016 | Kopychev et al. |
| 9,320,680 B2 | 4/2016 | Schröder |
| 9,345,871 B2 | 5/2016 | Guala |
| 9,358,332 B2 | 6/2016 | McGill et al. |
| 9,381,290 B2 | 7/2016 | Yu et al. |
| 9,393,356 B2 | 7/2016 | Karoor et al. |
| 9,408,958 B2 | 8/2016 | Wang et al. |
| 9,427,518 B2 | 8/2016 | Brueckner |
| 9,433,768 B2 | 9/2016 | Tekeste et al. |
| 9,440,016 B2 | 9/2016 | Lin et al. |
| 9,440,019 B2 | 9/2016 | Falkenhagen et al. |
| 9,470,220 B2 | 10/2016 | Becker |
| 9,471,754 B2 | 10/2016 | Mastalli et al. |
| 9,474,841 B2 | 10/2016 | Volker |
| 9,495,511 B2 | 11/2016 | Harrington et al. |
| 9,500,188 B2 | 11/2016 | Ly et al. |
| 9,514,131 B1 | 12/2016 | Bochenko et al. |
| 9,519,969 B1 | 12/2016 | Kusens |
| 9,539,387 B2 | 1/2017 | Fini et al. |
| 9,555,232 B2 | 1/2017 | Davis et al. |
| 9,593,679 B2 | 3/2017 | Gray et al. |
| 9,610,518 B2 | 4/2017 | Kamen et al. |
| 9,616,163 B2 | 4/2017 | Wong et al. |
| 9,629,993 B2 | 4/2017 | Klewinghaus |
| 9,651,511 B2 | 5/2017 | Howell et al. |
| 9,669,145 B2 | 6/2017 | Günther et al. |
| 9,677,555 B2 | 6/2017 | Kamen et al. |
| 9,687,646 B2 | 6/2017 | Sobue et al. |
| 9,694,125 B2 | 7/2017 | Plahey et al. |
| 9,694,126 B2 | 7/2017 | Hedmann et al. |
| 9,700,711 B2 | 7/2017 | Grant et al. |
| 9,724,270 B2 | 8/2017 | Bonnal et al. |
| 9,724,298 B2 | 8/2017 | Nilsson et al. |
| 9,724,505 B2 | 8/2017 | Williams et al. |
| 10,973,968 B2 | 4/2021 | Rohde |
| 2001/0005487 A1 | 6/2001 | Kamibayashi et al. |
| 2002/0045851 A1 | 4/2002 | Suzuki et al. |
| 2002/0072718 A1 | 6/2002 | Brugger et al. |
| 2002/0087126 A1 | 7/2002 | Quah |
| 2002/0120227 A1 | 8/2002 | Childers et al. |
| 2002/0123715 A1 | 9/2002 | Sorenson et al. |
| 2002/0162778 A1 | 11/2002 | Peabody et al. |
| 2003/0065284 A1 | 4/2003 | Briggs |
| 2003/0086794 A1 | 5/2003 | Gray et al. |
| 2003/0143352 A1 | 7/2003 | Yang et al. |
| 2003/0153865 A1 | 8/2003 | Connell et al. |
| 2003/0217976 A1 | 11/2003 | Bowman et al. |
| 2003/0218623 A1 | 11/2003 | Krensky et al. |
| 2004/0019312 A1 | 1/2004 | Childers et al. |
| 2004/0031756 A1 | 2/2004 | Suzuki et al. |
| 2004/0040620 A1 | 3/2004 | Brauer et al. |
| 2004/0078024 A1 | 4/2004 | Peluso et al. |
| 2004/0087890 A1 | 5/2004 | Sakai |
| 2004/0099521 A1 | 5/2004 | Demers et al. |
| 2004/0108223 A1 | 6/2004 | Jansson |
| 2004/0111294 A1 | 6/2004 | McNally et al. |
| 2004/0215129 A1 | 10/2004 | Edgson et al. |
| 2004/0215336 A1 | 10/2004 | Udipi et al. |
| 2004/0221643 A1 | 11/2004 | Ehwald et al. |
| 2004/0254513 A1 | 12/2004 | Shang et al. |
| 2005/0006296 A1 | 1/2005 | Sullivan et al. |
| 2005/0020507 A1 | 1/2005 | Zieske et al. |
| 2005/0082226 A1 | 4/2005 | Bene et al. |
| 2005/0089994 A1 | 4/2005 | Neftel |
| 2005/0094483 A1 | 5/2005 | Demers et al. |
| 2005/0094485 A1 | 5/2005 | Demers et al. |
| 2005/0095154 A1 | 5/2005 | Tracey et al. |
| 2005/0126998 A1 | 6/2005 | Childers |
| 2005/0131141 A1 | 6/2005 | Poss et al. |
| 2005/0167363 A1 | 8/2005 | Taylor |
| 2005/0173344 A1 | 8/2005 | Bowman et al. |
| 2005/0202395 A1 | 9/2005 | Edrich et al. |
| 2005/0209563 A1 | 9/2005 | Hopping et al. |
| 2005/0211373 A1 | 9/2005 | Tomasetti et al. |
| 2005/0224372 A1 | 10/2005 | Sasso et al. |
| 2005/0244909 A1 | 11/2005 | Hamada et al. |
| 2005/0283132 A1 | 12/2005 | Stanus et al. |
| 2006/0005886 A1 | 1/2006 | Parrino et al. |
| 2006/0015015 A1 | 1/2006 | Kawamoto et al. |
| 2006/0161107 A1 | 7/2006 | Mantle |
| 2006/0172954 A1 | 8/2006 | Jensen et al. |
| 2006/0189923 A1 | 8/2006 | Neftel et al. |
| 2006/0195064 A1 | 8/2006 | Plahey et al. |
| 2007/0007208 A1 | 1/2007 | Brugger et al. |
| 2007/0043317 A1 | 2/2007 | Sugawara |
| 2007/0048161 A1 | 3/2007 | Moubayed |
| 2007/0088314 A1 | 4/2007 | Gollier et al. |
| 2007/0106197 A1 | 5/2007 | Lauman et al. |
| 2007/0106247 A1 | 5/2007 | Burnett et al. |
| 2007/0112297 A1 | 5/2007 | Plahey et al. |
| 2007/0149913 A1 | 6/2007 | Busby et al. |
| 2007/0179422 A1 | 8/2007 | Schnell et al. |
| 2007/0194792 A1 | 8/2007 | Quackenbush et al. |
| 2007/0213651 A1 | 9/2007 | Busby et al. |
| 2007/0213654 A1 | 9/2007 | Lundtveit et al. |
| 2007/0213665 A1 | 9/2007 | Curtin et al. |
| 2007/0253463 A1 | 11/2007 | Perry et al. |
| 2007/0276328 A1 | 11/2007 | Childers et al. |
| 2007/0287966 A1 | 12/2007 | Keeley |
| 2008/0015492 A1 | 1/2008 | Biesel |
| 2008/0023135 A1 | 1/2008 | Ivansons et al. |
| 2008/0027374 A1 | 1/2008 | Jensen et al. |
| 2008/0031746 A9 | 2/2008 | Gray et al. |
| 2008/0058712 A1 | 3/2008 | Plahey |
| 2008/0065006 A1 | 3/2008 | Roger et al. |
| 2008/0097283 A1 | 4/2008 | Plahey |
| 2008/0101969 A1 | 5/2008 | Moubayed |
| 2008/0112258 A1 | 5/2008 | Demers et al. |
| 2008/0125693 A1 | 5/2008 | Gavin et al. |
| 2008/0138223 A1 | 6/2008 | Lanigan et al. |
| 2008/0161751 A1 | 7/2008 | Plahey et al. |
| 2008/0183126 A1 | 7/2008 | Landherr et al. |
| 2008/0183127 A1 | 7/2008 | Landherr et al. |
| 2008/0200865 A1 | 8/2008 | Bedingfield |
| 2008/0200866 A1 | 8/2008 | Prisco et al. |

(56) References Cited

U.S. PATENT DOCUMENTS

| | | |
|---|---|---|
| 2008/0200867 A1 | 8/2008 | Bedingfield |
| 2008/0200868 A1 | 8/2008 | Alberti et al. |
| 2008/0200869 A1 | 8/2008 | Bedingfield |
| 2008/0208195 A1 | 8/2008 | Shores et al. |
| 2008/0216898 A1 | 9/2008 | Grant et al. |
| 2008/0230450 A1* | 9/2008 | Burbank ............ A61M 1/1668 210/85 |
| 2008/0240929 A1 | 10/2008 | Kamen et al. |
| 2008/0243211 A1 | 10/2008 | Cartwright et al. |
| 2008/0253427 A1 | 10/2008 | Kamen et al. |
| 2008/0253911 A1 | 10/2008 | Demers et al. |
| 2008/0273996 A1 | 11/2008 | Gray et al. |
| 2008/0275382 A1 | 11/2008 | Biesel et al. |
| 2009/0007642 A1 | 1/2009 | Busby et al. |
| 2009/0008306 A1 | 1/2009 | Cicchello et al. |
| 2009/0009290 A1 | 1/2009 | Kneip et al. |
| 2009/0012447 A1 | 1/2009 | Huitt et al. |
| 2009/0012451 A1 | 1/2009 | Sobue et al. |
| 2009/0012452 A1 | 1/2009 | Slepicka et al. |
| 2009/0012453 A1 | 1/2009 | Childers et al. |
| 2009/0012455 A1 | 1/2009 | Childers et al. |
| 2009/0012458 A1 | 1/2009 | Childers et al. |
| 2009/0012460 A1 | 1/2009 | Steck et al. |
| 2009/0012464 A1 | 1/2009 | Martin et al. |
| 2009/0024096 A1 | 1/2009 | Hai et al. |
| 2009/0054873 A1 | 2/2009 | Landherr et al. |
| 2009/0078592 A1 | 3/2009 | Jensen et al. |
| 2009/0082758 A1 | 3/2009 | Gill et al. |
| 2009/0095679 A1 | 4/2009 | Demers et al. |
| 2009/0098215 A1 | 4/2009 | Riser et al. |
| 2009/0101549 A1 | 4/2009 | Kamen et al. |
| 2009/0112151 A1 | 4/2009 | Chapman et al. |
| 2009/0143723 A1 | 6/2009 | Szpara et al. |
| 2009/0149810 A1 | 6/2009 | Ring et al. |
| 2009/0169872 A1 | 7/2009 | Krongauz et al. |
| 2009/0173682 A1* | 7/2009 | Robinson ............ A61M 1/28 210/240 |
| 2009/0177149 A1 | 7/2009 | Childers et al. |
| 2009/0182263 A1 | 7/2009 | Burbank et al. |
| 2009/0185920 A1 | 7/2009 | Lanigan et al. |
| 2009/0196776 A1 | 8/2009 | Moubayed |
| 2009/0198170 A1 | 8/2009 | Childers et al. |
| 2009/0206023 A1 | 8/2009 | Rohde et al. |
| 2009/0212178 A1 | 8/2009 | Westberg |
| 2009/0213521 A1 | 8/2009 | Bedingfield |
| 2009/0218290 A1 | 9/2009 | Poss et al. |
| 2009/0222119 A1 | 9/2009 | Plahey et al. |
| 2009/0223899 A1 | 9/2009 | Poss et al. |
| 2009/0232908 A1 | 9/2009 | Zhou |
| 2009/0264854 A1 | 10/2009 | Jensen et al. |
| 2009/0275881 A1 | 11/2009 | Lo et al. |
| 2009/0275883 A1 | 11/2009 | Chapman et al. |
| 2009/0277276 A1 | 11/2009 | Evering et al. |
| 2009/0294339 A1 | 12/2009 | Biewer et al. |
| 2009/0295591 A1 | 12/2009 | Bedingfield |
| 2009/0299272 A1 | 12/2009 | Hopping et al. |
| 2009/0299273 A1 | 12/2009 | Lee et al. |
| 2010/0004588 A1 | 1/2010 | Yeh et al. |
| 2010/0004589 A1 | 1/2010 | Hedmann et al. |
| 2010/0004590 A1 | 1/2010 | Hedmann et al. |
| 2010/0005416 A1 | 1/2010 | Hedmann et al. |
| 2010/0010423 A1 | 1/2010 | Yu et al. |
| 2010/0010424 A1 | 1/2010 | Yu et al. |
| 2010/0010425 A1 | 1/2010 | Yu et al. |
| 2010/0010426 A1 | 1/2010 | Childers et al. |
| 2010/0010427 A1 | 1/2010 | Yu et al. |
| 2010/0010428 A1 | 1/2010 | Yu et al. |
| 2010/0016802 A1 | 1/2010 | Tambourgi et al. |
| 2010/0019686 A1 | 1/2010 | Gutierrez |
| 2010/0028170 A1 | 2/2010 | Schneeberger et al. |
| 2010/0028208 A1 | 2/2010 | Shekalim et al. |
| 2010/0038322 A1 | 2/2010 | Hedmann et al. |
| 2010/0049158 A1 | 2/2010 | Roger |
| 2010/0051552 A1 | 3/2010 | Rohde et al. |
| 2010/0063445 A1 | 3/2010 | Sternberg et al. |
| 2010/0069817 A1* | 3/2010 | Falkvall ............ A61M 1/1668 604/416 |
| 2010/0078387 A1 | 4/2010 | Wong |
| 2010/0084326 A1 | 4/2010 | Takesawa |
| 2010/0087777 A1 | 4/2010 | Hopping et al. |
| 2010/0096329 A1 | 4/2010 | Kotanko et al. |
| 2010/0100027 A1 | 4/2010 | Schilthuizen et al. |
| 2010/0100034 A1 | 4/2010 | Wich-Heiter |
| 2010/0114012 A1 | 5/2010 | Sandford et al. |
| 2010/0129247 A1 | 5/2010 | Lauer |
| 2010/0130918 A1 | 5/2010 | Elahi |
| 2010/0130919 A1 | 5/2010 | Elahi |
| 2010/0133153 A1 | 6/2010 | Beden et al. |
| 2010/0137782 A1 | 6/2010 | Jansson et al. |
| 2010/0168652 A1 | 7/2010 | Andherr et al. |
| 2010/0169513 A1 | 7/2010 | Levin |
| 2010/0185132 A1 | 7/2010 | Han et al. |
| 2010/0187476 A1 | 7/2010 | Yugari et al. |
| 2010/0191180 A1 | 7/2010 | Childers et al. |
| 2010/0191181 A1 | 7/2010 | Childers et al. |
| 2010/0192686 A1 | 8/2010 | Kamen et al. |
| 2010/0197817 A1 | 8/2010 | Bui et al. |
| 2010/0204765 A1 | 8/2010 | Hall et al. |
| 2010/0217178 A1 | 8/2010 | Lo et al. |
| 2010/0217179 A1 | 8/2010 | Lo et al. |
| 2010/0217180 A1 | 8/2010 | Akonur et al. |
| 2010/0222735 A1 | 9/2010 | Plahey et al. |
| 2010/0224492 A1 | 9/2010 | Ding et al. |
| 2010/0229978 A1 | 9/2010 | Zhou |
| 2010/0241062 A1 | 9/2010 | Morris et al. |
| 2010/0252490 A1 | 10/2010 | Fulkerson et al. |
| 2010/0252702 A1 | 10/2010 | Spang et al. |
| 2010/0258690 A1 | 10/2010 | Kleitsch et al. |
| 2010/0296953 A1 | 11/2010 | Gray |
| 2010/0308243 A1 | 12/2010 | Bedingfield |
| 2010/0312174 A1 | 12/2010 | Hoffman |
| 2010/0314314 A1 | 12/2010 | Ding et al. |
| 2010/0326916 A1 | 12/2010 | Wrazel et al. |
| 2010/0331768 A1 | 12/2010 | Hedmann et al. |
| 2011/0000902 A1 | 1/2011 | Hedmann et al. |
| 2011/0004152 A1 | 1/2011 | Brady et al. |
| 2011/0010101 A1 | 1/2011 | Lo et al. |
| 2011/0015610 A1 | 1/2011 | Plahey et al. |
| 2011/0017665 A1 | 1/2011 | Updyke et al. |
| 2011/0034866 A1 | 2/2011 | Zhang et al. |
| 2011/0038755 A1 | 2/2011 | Pesci et al. |
| 2011/0040242 A1 | 2/2011 | Fallon et al. |
| 2011/0040243 A1 | 2/2011 | Busby et al. |
| 2011/0040244 A1 | 2/2011 | Busby et al. |
| 2011/0046533 A1 | 2/2011 | Stefani et al. |
| 2011/0054397 A1 | 3/2011 | Schneeberger |
| 2011/0064608 A1 | 3/2011 | Lee et al. |
| 2011/0085923 A1 | 4/2011 | Gray et al. |
| 2011/0092893 A1 | 4/2011 | Demers et al. |
| 2011/0092895 A1 | 4/2011 | Yardimci et al. |
| 2011/0093294 A1 | 4/2011 | Elahi et al. |
| 2011/0098635 A1 | 4/2011 | Helmore et al. |
| 2011/0105979 A1 | 5/2011 | Schlaeper et al. |
| 2011/0105981 A1 | 5/2011 | Wagner et al. |
| 2011/0114559 A1 | 5/2011 | Fislage et al. |
| 2011/0131058 A1 | 6/2011 | McNally et al. |
| 2011/0132838 A1 | 6/2011 | Curtis et al. |
| 2011/0137236 A1 | 6/2011 | Prisco et al. |
| 2011/0137237 A1 | 6/2011 | Prisco et al. |
| 2011/0138936 A1 | 6/2011 | Collins et al. |
| 2011/0141116 A1 | 6/2011 | Dalesch et al. |
| 2011/0144557 A1 | 6/2011 | Childers et al. |
| 2011/0144569 A1 | 6/2011 | Britton et al. |
| 2011/0158823 A1 | 6/2011 | Wang et al. |
| 2011/0160649 A1 | 6/2011 | Pan |
| 2011/0163033 A1 | 7/2011 | Chapman et al. |
| 2011/0166507 A1 | 7/2011 | Childers et al. |
| 2011/0171713 A1 | 7/2011 | Bluchel et al. |
| 2011/0184339 A1 | 7/2011 | Tan |
| 2011/0184340 A1 | 7/2011 | Tan et al. |
| 2011/0186517 A1 | 8/2011 | Hedmann et al. |
| 2011/0189048 A1 | 8/2011 | Curtis et al. |
| 2011/0190691 A1 | 8/2011 | Cazzini |
| 2011/0192796 A1 | 8/2011 | Smejtek et al. |

(56) References Cited

U.S. PATENT DOCUMENTS

| | | |
|---|---|---|
| 2011/0196289 A1 | 8/2011 | Plahey et al. |
| 2011/0198350 A1 | 8/2011 | Meisberger et al. |
| 2011/0218486 A1 | 9/2011 | Huitt et al. |
| 2011/0224603 A1 | 9/2011 | Richter |
| 2011/0230822 A1 | 9/2011 | Lee et al. |
| 2011/0249916 A1 | 10/2011 | Herrenbauer et al. |
| 2011/0257124 A1 | 10/2011 | Fenn et al. |
| 2011/0262555 A1 | 10/2011 | Riser et al. |
| 2011/0264042 A1 | 10/2011 | Shang et al. |
| 2011/0266221 A1 | 11/2011 | Ware et al. |
| 2011/0275984 A1 | 11/2011 | Biewer et al. |
| 2011/0284377 A1 | 11/2011 | Rohde |
| 2011/0286167 A1 | 11/2011 | Winkler |
| 2011/0288480 A1 | 11/2011 | Bedingfield et al. |
| 2011/0300231 A1 | 12/2011 | Peterson et al. |
| 2011/0309019 A1 | 12/2011 | Ahrens |
| 2012/0001762 A1 | 1/2012 | Turner et al. |
| 2012/0022440 A1 | 1/2012 | Childers et al. |
| 2012/0029325 A1 | 2/2012 | Neftel |
| 2012/0029937 A1 | 2/2012 | Neftel et al. |
| 2012/0030933 A1 | 2/2012 | Lanigan et al. |
| 2012/0031826 A1 | 2/2012 | Childers et al. |
| 2012/0035533 A1 | 2/2012 | Britton et al. |
| 2012/0058328 A1 | 3/2012 | Tourvieille et al. |
| 2012/0065581 A1 | 3/2012 | Childers et al. |
| 2012/0067805 A1 | 3/2012 | Childers et al. |
| 2012/0071815 A1 | 3/2012 | Childers et al. |
| 2012/0071816 A1 | 3/2012 | Busby et al. |
| 2012/0074060 A1 | 3/2012 | Lass |
| 2012/0078168 A1 | 3/2012 | Veneroni et al. |
| 2012/0082576 A1 | 4/2012 | Beck et al. |
| 2012/0089085 A1 | 4/2012 | Childers et al. |
| 2012/0095392 A1 | 4/2012 | Jensen et al. |
| 2012/0105850 A1 | 5/2012 | Slepicka |
| 2012/0116294 A1 | 5/2012 | Boenig et al. |
| 2012/0132574 A1 | 5/2012 | Ware et al. |
| 2012/0145615 A1 | 6/2012 | Rohde et al. |
| 2012/0150102 A1 | 6/2012 | Childers et al. |
| 2012/0179133 A1 | 7/2012 | Bedingfield et al. |
| 2012/0185267 A1 | 7/2012 | Kamen et al. |
| 2012/0185619 A1 | 7/2012 | Levin |
| 2012/0199205 A1 | 8/2012 | Eyrard et al. |
| 2012/0205306 A1 | 8/2012 | Reich et al. |
| 2012/0209169 A1 | 8/2012 | Morris et al. |
| 2012/0211422 A1 | 8/2012 | Thys |
| 2012/0212434 A1 | 8/2012 | Bluemler et al. |
| 2012/0212455 A1 | 8/2012 | Kloeffel |
| 2012/0215151 A1 | 8/2012 | Han et al. |
| 2012/0215159 A1 | 8/2012 | Childers et al. |
| 2012/0226237 A1 | 9/2012 | Russo |
| 2012/0230844 A1 | 9/2012 | Farrell et al. |
| 2012/0232469 A1 | 9/2012 | Medina |
| 2012/0238525 A1 | 9/2012 | Leypoldt et al. |
| 2012/0241367 A1 | 9/2012 | Childers et al. |
| 2012/0248017 A1 | 10/2012 | Beiriger et al. |
| 2012/0259275 A1 | 10/2012 | Jensen et al. |
| 2012/0265145 A1 | 10/2012 | Mefti et al. |
| 2012/0271226 A1 | 10/2012 | Farrell et al. |
| 2012/0271273 A1 | 10/2012 | Childers et al. |
| 2012/0273354 A1 | 11/2012 | Orhan et al. |
| 2012/0283629 A1 | 11/2012 | Childers et al. |
| 2012/0310150 A1 | 12/2012 | Brandl et al. |
| 2012/0318740 A1 | 12/2012 | Ekdahl et al. |
| 2013/0006171 A1 | 1/2013 | Griessmann et al. |
| 2013/0020237 A1 | 1/2013 | Wilt et al. |
| 2013/0030356 A1 | 1/2013 | Ding et al. |
| 2013/0030404 A1 | 1/2013 | Gerlach et al. |
| 2013/0037142 A1 | 2/2013 | Farrell |
| 2013/0037461 A1 | 2/2013 | Biewer et al. |
| 2013/0037465 A1 | 2/2013 | Heyes et al. |
| 2013/0056419 A1 | 3/2013 | Curtis |
| 2013/0072895 A1* | 3/2013 | Kreischer ............... B29C 48/08 |
| | | 604/408 |
| 2013/0075309 A1 | 3/2013 | West et al. |
| 2013/0079705 A1 | 3/2013 | Cazzini |
| 2013/0079706 A1 | 3/2013 | Childers et al. |
| 2013/0085437 A1 | 4/2013 | Deshpande |
| 2013/0085451 A1 | 4/2013 | Sheu |
| 2013/0106609 A1 | 5/2013 | Singh et al. |
| 2013/0126430 A1 | 5/2013 | Kenley et al. |
| 2013/0131581 A1 | 5/2013 | Lundtveit et al. |
| 2013/0131583 A1 | 5/2013 | Chapman et al. |
| 2013/0138037 A1 | 5/2013 | Lee et al. |
| 2013/0150781 A1 | 6/2013 | Busby et al. |
| 2013/0153048 A1 | 6/2013 | Schwalm |
| 2013/0158469 A1 | 6/2013 | Hopping et al. |
| 2013/0165848 A1 | 6/2013 | Sebesta et al. |
| 2013/0167052 A1 | 6/2013 | Niesslein et al. |
| 2013/0172806 A1 | 7/2013 | Griessmann et al. |
| 2013/0177455 A1 | 7/2013 | Kamen et al. |
| 2013/0180905 A1 | 7/2013 | Wong |
| 2013/0186759 A1 | 7/2013 | Lin et al. |
| 2013/0190681 A1 | 7/2013 | Jansson et al. |
| 2013/0193041 A1 | 8/2013 | Rohde |
| 2013/0195792 A1 | 8/2013 | Chan et al. |
| 2013/0204173 A1 | 8/2013 | Kelly et al. |
| 2013/0205873 A1 | 8/2013 | Wagner et al. |
| 2013/0211322 A1 | 8/2013 | Degen et al. |
| 2013/0245530 A1 | 9/2013 | Brandl et al. |
| 2013/0245531 A1 | 9/2013 | Brandl et al. |
| 2013/0248448 A1 | 9/2013 | Shah et al. |
| 2013/0248449 A1 | 9/2013 | Kelly et al. |
| 2013/0263650 A1 | 10/2013 | Nier et al. |
| 2013/0272902 A1 | 10/2013 | Chappel |
| 2013/0277306 A1 | 10/2013 | Chapman et al. |
| 2013/0310726 A1 | 11/2013 | Miller et al. |
| 2013/0310735 A1 | 11/2013 | Yu et al. |
| 2013/0310736 A1 | 11/2013 | Hedmann et al. |
| 2013/0313191 A1 | 11/2013 | Wolf et al. |
| 2013/0317795 A1 | 11/2013 | Akonur et al. |
| 2013/0324915 A1 | 12/2013 | (Krensky) Britton et al. |
| 2013/0330208 A1 | 12/2013 | Ly et al. |
| 2013/0331774 A1 | 12/2013 | Farrell et al. |
| 2013/0331775 A1 | 12/2013 | Britton et al. |
| 2013/0334138 A1 | 12/2013 | Cicchello et al. |
| 2013/0338102 A1 | 12/2013 | Martis et al. |
| 2013/0345621 A1 | 12/2013 | Cicchello et al. |
| 2013/0346099 A1 | 12/2013 | Yu et al. |
| 2013/0346102 A1 | 12/2013 | Yu et al. |
| 2014/0010691 A1 | 1/2014 | Lanigan et al. |
| 2014/0018272 A1 | 1/2014 | Thoea et al. |
| 2014/0018727 A1 | 1/2014 | Burbank et al. |
| 2014/0021115 A1 | 1/2014 | Ellegaard |
| 2014/0027380 A1 | 1/2014 | Childers et al. |
| 2014/0031631 A1 | 1/2014 | Hall et al. |
| 2014/0046150 A1 | 2/2014 | Gagel et al. |
| 2014/0046248 A1 | 2/2014 | Fini et al. |
| 2014/0052044 A1 | 2/2014 | Crnkovich et al. |
| 2014/0074018 A1 | 3/2014 | Childers et al. |
| 2014/0098359 A1 | 4/2014 | Gross et al. |
| 2014/0129250 A1 | 5/2014 | Daniel et al. |
| 2014/0135878 A1 | 5/2014 | Burnett et al. |
| 2014/0148409 A1 | 5/2014 | Ohta et al. |
| 2014/0188040 A1 | 7/2014 | Busby et al. |
| 2014/0207055 A1 | 7/2014 | Junod et al. |
| 2014/0216994 A1 | 8/2014 | Ki |
| 2014/0217029 A1 | 8/2014 | Meyer et al. |
| 2014/0217030 A1 | 8/2014 | Meyer et al. |
| 2014/0249683 A1 | 9/2014 | Gray et al. |
| 2014/0263063 A1* | 9/2014 | Jones .................... G01N 24/08 |
| | | 210/96.2 |
| 2014/0288947 A1 | 9/2014 | Simpson et al. |
| 2014/0291218 A1 | 10/2014 | Bluchel et al. |
| 2014/0299545 A1 | 10/2014 | Wrazel et al. |
| 2014/0316332 A1 | 10/2014 | Lo et al. |
| 2014/0360594 A1 | 12/2014 | Lee et al. |
| 2015/0005699 A1* | 1/2015 | Burbank ............... A61M 1/282 |
| | | 604/29 |
| 2015/0014249 A1 | 1/2015 | Alberti et al. |
| 2015/0051536 A1 | 2/2015 | Mendels et al. |
| 2015/0088053 A1 | 3/2015 | Lundtveit et al. |
| 2015/0093450 A1 | 4/2015 | Riser et al. |
| 2015/0129055 A1 | 5/2015 | Byler |
| 2015/0133854 A1 | 5/2015 | Zhu et al. |

(56) References Cited

U.S. PATENT DOCUMENTS

| | | |
|---|---|---|
| 2015/0159643 A1 | 6/2015 | Koob |
| 2015/0196698 A1 | 7/2015 | Grant et al. |
| 2015/0197431 A1 | 7/2015 | Shiki |
| 2015/0204807 A1 | 7/2015 | Kamen et al. |
| 2015/0209500 A1 | 7/2015 | Lin et al. |
| 2015/0231571 A1 | 8/2015 | Volker |
| 2015/0233367 A1 | 8/2015 | Shimogata et al. |
| 2015/0273471 A1* | 10/2015 | Manzella, Jr. .......... A61M 1/34 422/501 |
| 2015/0276742 A1 | 10/2015 | Henrie |
| 2015/0335808 A1 | 11/2015 | White et al. |
| 2015/0359956 A1 | 12/2015 | Gray et al. |
| 2016/0030654 A1 | 2/2016 | Singh et al. |
| 2016/0051949 A1 | 2/2016 | Jansson et al. |
| 2016/0097382 A1 | 4/2016 | Kamen et al. |
| 2016/0106904 A1 | 4/2016 | Cicchello et al. |
| 2016/0153444 A1 | 6/2016 | Chappel et al. |
| 2016/0193399 A1 | 7/2016 | Wallace et al. |
| 2016/0206804 A1 | 7/2016 | Holmer et al. |
| 2016/0239637 A1 | 8/2016 | Miller et al. |
| 2016/0245277 A1 | 8/2016 | Lanigan et al. |
| 2016/0271312 A1 | 9/2016 | Lance et al. |
| 2016/0310653 A1 | 10/2016 | Wang et al. |
| 2016/0319954 A1 | 11/2016 | Smith |
| 2016/0346451 A1 | 12/2016 | Stonger et al. |
| 2016/0362234 A1 | 12/2016 | Peret et al. |
| 2016/0367794 A1 | 12/2016 | Bedingfield |
| 2017/0043079 A1 | 2/2017 | Jensen et al. |
| 2017/0112992 A1 | 4/2017 | Plahey et al. |
| 2017/0157310 A1 | 6/2017 | Scarpaci et al. |
| 2017/0157311 A1 | 6/2017 | Egley |
| 2017/0232175 A1 | 8/2017 | Burbank et al. |
| 2017/0281846 A1 | 10/2017 | Manda et al. |
| 2017/0319768 A1 | 11/2017 | Szpara et al. |
| 2017/0319769 A1 | 11/2017 | Wieslander et al. |
| 2017/0319770 A1 | 11/2017 | Fitzgerald et al. |
| 2017/0333609 A1 | 11/2017 | O'Brien et al. |
| 2018/0021501 A1 | 1/2018 | Gerber et al. |
| 2018/0043079 A1 | 2/2018 | Gerber et al. |
| 2018/0066648 A1 | 3/2018 | Kamen et al. |
| 2018/0078692 A1 | 3/2018 | Cicchello et al. |
| 2018/0093031 A1 | 4/2018 | Crawford et al. |
| 2018/0106246 A1 | 4/2018 | Kamen et al. |
| 2018/0128259 A1 | 5/2018 | Kamen et al. |

FOREIGN PATENT DOCUMENTS

| | | |
|---|---|---|
| CA | 2832661 | 8/2016 |
| CN | 201150709 | 11/2008 |
| CN | 201710718 U | 1/2011 |
| CN | 201806987 U | 4/2011 |
| CN | 101901000 B | 11/2011 |
| CN | 102258942 A | 11/2011 |
| CN | 202116617 U | 1/2012 |
| CN | 102363054 A | 2/2012 |
| CN | 202355628 U | 8/2012 |
| CN | 202379834 U | 8/2012 |
| CN | 202478260 U | 10/2012 |
| CN | 202505852 U | 10/2012 |
| CN | 202542986 U | 11/2012 |
| CN | 102989047 A | 3/2013 |
| CN | 202822485 U | 3/2013 |
| CN | 204723486 U | 10/2015 |
| CN | 105013031 A | 11/2015 |
| CN | 204824277 U | 12/2015 |
| DE | 2838414 A1 | 3/1980 |
| DE | 4308586 C1 | 5/1994 |
| DE | 19546027 C1 | 4/1997 |
| DE | 29918801 U1 | 3/2000 |
| DE | 69725104 | 7/2004 |
| DE | 102007020573 A1 | 11/2008 |
| DE | 102007053752 A1 | 5/2009 |
| DE | 102008045422 A1 | 3/2010 |
| DE | 102009037917 A1 | 2/2011 |
| DE | 102010009816 A1 | 9/2011 |
| DE | 102010033241 A1 | 2/2012 |
| DE | 102010053903 A1 | 6/2012 |
| DE | 102011103325 A1 | 12/2012 |
| DE | 102012004673 A1 | 9/2013 |
| DE | 102012007412 A1 | 10/2013 |
| DE | 102013103223 A1 | 10/2014 |
| DE | 102013013414 | 1/2015 |
| DE | 102013013415 A1 | 2/2015 |
| DE | 102013016204 A1 | 4/2015 |
| DE | 102013018444 A1 | 5/2015 |
| DE | 102014201714 A1 | 8/2015 |
| DE | 102014004476 A1 | 10/2015 |
| DE | 102014013152 A1 | 3/2016 |
| DE | 102015010418 A1 | 2/2017 |
| EP | 0049673 A1 * | 4/1982 |
| EP | 100682 A1 | 2/1984 |
| EP | 0104460 A2 | 4/1984 |
| EP | 0112104 A2 | 6/1984 |
| EP | 0256640 A2 | 2/1988 |
| EP | 0265352 A1 | 4/1988 |
| EP | 0090093 B1 | 6/1988 |
| EP | 0367252 A2 | 5/1990 |
| EP | 0442310 A1 | 8/1991 |
| EP | 0611227 A1 | 8/1994 |
| EP | 0711569 A1 | 5/1996 |
| EP | 0763367 A1 | 3/1997 |
| EP | 0778033 A2 | 6/1997 |
| EP | 0813880 A1 | 12/1997 |
| EP | 1187642 A1 | 3/2002 |
| EP | 1314442 A1 | 5/2003 |
| EP | 0846470 B1 | 9/2003 |
| EP | 1346749 A2 | 9/2003 |
| EP | 1048316 B1 | 10/2003 |
| EP | 0971674 B1 | 12/2003 |
| EP | 0914093 B1 | 2/2004 |
| EP | 1438981 A2 | 7/2004 |
| EP | 1438982 A2 | 7/2004 |
| EP | 0970699 B1 | 9/2005 |
| EP | 0994739 B1 | 9/2005 |
| EP | 0958832 B1 | 1/2006 |
| EP | 1648536 A2 | 4/2006 |
| EP | 1066068 B1 | 7/2006 |
| EP | 1677900 A2 | 7/2006 |
| EP | 1351726 B1 | 2/2007 |
| EP | 1382359 B1 | 2/2007 |
| EP | 1110564 B1 | 5/2007 |
| EP | 1236685 B1 | 8/2007 |
| EP | 1867359 A2 | 12/2007 |
| EP | 1938849 A2 | 7/2008 |
| EP | 1191960 B1 | 9/2008 |
| EP | 1582227 B1 | 11/2008 |
| EP | 1218039 B1 | 2/2009 |
| EP | 1641473 B1 | 4/2010 |
| EP | 1357958 B1 | 8/2010 |
| EP | 2289577 A1 | 3/2011 |
| EP | 1432462 B1 | 5/2011 |
| EP | 2350897 A2 | 8/2011 |
| EP | 2402047 A1 | 1/2012 |
| EP | 1509231 B1 | 2/2012 |
| EP | 1465687 B2 | 5/2012 |
| EP | 2446910 A1 | 5/2012 |
| EP | 1195171 B1 | 8/2012 |
| EP | 2503150 A1 | 9/2012 |
| EP | 2510958 A1 | 10/2012 |
| EP | 2517742 A2 | 10/2012 |
| EP | 1735028 B1 | 7/2013 |
| EP | 2656785 A1 | 10/2013 |
| EP | 2689790 A1 | 1/2014 |
| EP | 2712648 B1 | 3/2015 |
| EP | 2688602 A2 | 10/2015 |
| EP | 1878430 B1 | 4/2016 |
| EP | 2114487 B1 | 4/2016 |
| EP | 2131891 B1 | 4/2016 |
| EP | 2173433 B1 | 5/2016 |
| EP | 3222305 A1 | 9/2017 |
| FR | 2594340 A1 | 8/1987 |
| GB | 2021418 A | 12/1979 |
| GB | 2312055 B | 7/2000 |

(56) References Cited

FOREIGN PATENT DOCUMENTS

| | | |
|---|---|---|
| JP | S59166156 A | 9/1984 |
| JP | 60155952 A | 8/1985 |
| JP | S61008057 A | 1/1986 |
| JP | H05502614 A | 5/1993 |
| JP | 2001511400 A | 8/2001 |
| JP | 2002539896 A | 11/2002 |
| JP | 2002355305 A | 12/2002 |
| JP | 2003024435 A | 1/2003 |
| JP | 2003509126 A | 3/2003 |
| JP | 2003205031 A | 7/2003 |
| JP | 2004518462 A | 6/2004 |
| JP | 2006181386 A | 7/2006 |
| JP | 2005533574 A | 8/2006 |
| JP | 2006218037 A | 8/2006 |
| JP | 2008119509 A | 5/2008 |
| JP | 03150035 U | 4/2009 |
| JP | 2009131573 A | 6/2009 |
| JP | 2009139091 A | 6/2009 |
| JP | 2009142436 A | 7/2009 |
| JP | 2009533092 A | 9/2009 |
| JP | 2009539522 A | 11/2009 |
| JP | 2009279110 A | 12/2009 |
| JP | 2009279532 A | 12/2009 |
| JP | 2010502405 A | 1/2010 |
| JP | 2010042312 A | 2/2010 |
| JP | 2010088759 A | 4/2010 |
| JP | 2010099631 A | 5/2010 |
| JP | 2010131495 A | 6/2010 |
| JP | 2010175285 A | 8/2010 |
| JP | 2010214132 A | 9/2010 |
| JP | 2010238013 A | 10/2010 |
| JP | 2010532217 A | 10/2010 |
| JP | 2010279423 A | 12/2010 |
| JP | 2011056395 A | 3/2011 |
| JP | 2011067535 A | 4/2011 |
| JP | 2011120713 A | 6/2011 |
| JP | 2011131209 A | 7/2011 |
| JP | 2011188996 A | 9/2011 |
| JP | 2011189190 A | 9/2011 |
| JP | 2011207867 A | 10/2011 |
| JP | 2011217965 A | 11/2011 |
| JP | 2011241174 A | 12/2011 |
| JP | 2012011260 A | 1/2012 |
| JP | 2012071287 A | 4/2012 |
| JP | 2012075572 A | 4/2012 |
| JP | 2012075573 A | 4/2012 |
| JP | 2012075574 A | 4/2012 |
| JP | 2012075575 A | 4/2012 |
| JP | 2012210382 A | 11/2012 |
| JP | 2012223248 A | 11/2012 |
| JP | 2012228285 A | 11/2012 |
| JP | 2013006128 A | 1/2013 |
| JP | 2013048894 A | 3/2013 |
| JP | 2013048895 A | 3/2013 |
| JP | 2013202231 A | 10/2013 |
| JP | 2014014645 A | 1/2014 |
| JP | 2014519345 A | 8/2014 |
| JP | 2014184380 A | 10/2014 |
| JP | 2014184384 A | 10/2014 |
| JP | 2014184410 A | 10/2014 |
| JP | 2014184411 A | 10/2014 |
| JP | 2015517834 A | 6/2015 |
| JP | 2017000802 A | 1/2017 |
| JP | 2017006538 A | 1/2017 |
| JP | 6080937 B1 | 2/2017 |
| JP | 2018027256 A | 2/2018 |
| JP | 2018050751 A | 4/2018 |
| KR | 20120118906 A | 10/2012 |
| TW | M411244 U | 9/2011 |
| WO | 1983002060 A1 | 6/1983 |
| WO | 1984000137 A1 | 1/1984 |
| WO | 1984000340 A1 | 2/1984 |
| WO | 1992003202 A2 | 3/1992 |
| WO | 1994020154 A1 | 9/1994 |
| WO | 1996025214 A1 | 8/1996 |
| WO | WO-9625214 A1 * | 8/1996 ............... A61L 2/04 |
| WO | 1997007837 A1 | 3/1997 |
| WO | 1998032480 A1 | 7/1998 |
| WO | 1999006082 A1 | 2/1999 |
| WO | 2000057833 A1 | 10/2000 |
| WO | 2000057935 A1 | 10/2000 |
| WO | 0119413 A1 | 3/2001 |
| WO | 2001032237 A1 | 5/2001 |
| WO | 2001058509 A1 | 8/2001 |
| WO | 0232476 A2 | 4/2002 |
| WO | 2002066099 A2 | 8/2002 |
| WO | 2004006992 A1 | 1/2004 |
| WO | 2004009156 A2 | 1/2004 |
| WO | 2004043566 A2 | 5/2004 |
| WO | 2005009511 A2 | 2/2005 |
| WO | 2005042139 A1 | 5/2005 |
| WO | 2005089832 A2 | 9/2005 |
| WO | 2007061368 A1 | 5/2007 |
| WO | 2007091217 A1 | 8/2007 |
| WO | 2007103411 A2 | 9/2007 |
| WO | 2007118235 A2 | 10/2007 |
| WO | 2007144427 A2 | 12/2007 |
| WO | 2007148443 A1 | 12/2007 |
| WO | 2008086619 A1 | 7/2008 |
| WO | 2008106440 A1 | 9/2008 |
| WO | 2008154435 A2 | 12/2008 |
| WO | 2009005900 A1 | 1/2009 |
| WO | 2009094182 A2 | 7/2009 |
| WO | 2009094183 A1 | 7/2009 |
| WO | 2009094186 A2 | 7/2009 |
| WO | 2009127683 A1 | 10/2009 |
| WO | 2009134881 A1 | 11/2009 |
| WO | 2010002830 A2 | 1/2010 |
| WO | 2010009867 A1 | 1/2010 |
| WO | 2010020380 A1 | 2/2010 |
| WO | 2010024963 A1 | 3/2010 |
| WO | 2010031424 A1 | 3/2010 |
| WO | 2010059959 A2 | 5/2010 |
| WO | 2010121751 A2 | 10/2010 |
| WO | 2010143693 A1 | 12/2010 |
| WO | 2011017215 A1 | 2/2011 |
| WO | 2011052348 A1 | 5/2011 |
| WO | 2011065222 A1 | 6/2011 |
| WO | 2011091998 A1 | 8/2011 |
| WO | 2011113615 A1 | 9/2011 |
| WO | 2011132165 A1 | 10/2011 |
| WO | 2012049261 A1 | 4/2012 |
| WO | 2012087798 A2 | 6/2012 |
| WO | 2012095829 A2 | 7/2012 |
| WO | 2012129501 A3 | 11/2012 |
| WO | 2012148781 A1 | 11/2012 |
| WO | 2012163537 A1 | 12/2012 |
| WO | 2012172818 A1 | 12/2012 |
| WO | 2012176135 A1 | 12/2012 |
| WO | 2013000569 A1 | 1/2013 |
| WO | 2013012744 A2 | 1/2013 |
| WO | 2013019179 A1 | 2/2013 |
| WO | 2013019994 A2 | 2/2013 |
| WO | 2013040420 A2 | 3/2013 |
| WO | 2013051927 A1 | 4/2013 |
| WO | 2013057109 A1 | 4/2013 |
| WO | 2013110919 A1 | 8/2013 |
| WO | 2013114063 A1 | 8/2013 |
| WO | 2013121162 A1 | 8/2013 |
| WO | 2013135386 A1 | 9/2013 |
| WO | 2013135388 A1 | 9/2013 |
| WO | 2013141896 A1 | 9/2013 |
| WO | 2013159935 A1 | 10/2013 |
| WO | 2013163949 A1 | 11/2013 |
| WO | 2013185080 A1 | 12/2013 |
| WO | 2013191344 A1 | 12/2013 |
| WO | 2014009179 A1 | 1/2014 |
| WO | 2014053858 A1 | 4/2014 |
| WO | 2014081367 A1 | 5/2014 |
| WO | 2014106010 A1 | 7/2014 |
| WO | 2014124186 A2 | 8/2014 |
| WO | 2014155120 A1 | 10/2014 |
| WO | 2014162489 A1 | 10/2014 |
| WO | 2015050752 A1 | 4/2015 |

(56) References Cited

FOREIGN PATENT DOCUMENTS

| | | | |
|---|---|---|---|
| WO | 2015177606 A1 | 11/2015 | |
| WO | 2015188154 A1 | 12/2015 | |
| WO | WO-2016049542 A2 * | 3/2016 | ........... A61K 31/191 |
| WO | 2016059634 A2 | 4/2016 | |
| WO | 2016080883 A1 | 5/2016 | |
| WO | 2016088072 A1 | 6/2016 | |
| WO | 2016091366 A1 | 6/2016 | |
| WO | 2016095026 A1 | 6/2016 | |
| WO | 2016193930 A1 | 12/2016 | |
| WO | 2016206949 A1 | 12/2016 | |
| WO | 2017193065 A1 | 11/2017 | |
| WO | 2018041760 A1 | 3/2018 | |
| WO | 2018115028 A1 | 6/2018 | |

OTHER PUBLICATIONS

Office Action (Communication Pursuant to Article 94(3) EPC) dated Jun. 24, 2020 for European Patent Application No. 19173274.2.
English language abstract for Swedish application publication No. SE 198300739 A, published Aug. 13, 1983.
Examination Report for United Kingdom Patent Application No. 1316544.4 dated Nov. 1, 2017.
Extended European Search Report dated Apr. 2, 2019 for European Patent Application No. 18215332.0.
Extended European Search Report dated Oct. 22, 2019 for European Patent Application No. 19167042.1.
Extended European Search Report for European Application No. 17170146 dated Jul. 25, 2017.
Extended European Search Report for European Application No. 17170151.9 dated Aug. 22, 2017.
Extended European Search Report for European Patent Application No. 12760085.6 dated Sep. 25, 2015.
Extended European Search Report for European Patent Application No. 12871735.2 dated Oct. 15, 2015.
Extended European Search Report for European Patent Application No. 19166992.8 dated Aug. 2, 2019.
Extended European Search Report issued in EP Application 19173274.2 and dated Jul. 29, 2019.
International Search Report and Written Opinion dated Sep. 6, 2019 and issued in International Application No. PCT/US2019/019967.
International Search Report and Written Opinion for International Application No. PCT/US2012/30350 dated Sep. 13, 2012.
International Search Report and Written Opinion for International Application No. PCT/US2012/56781 dated Apr. 4, 2013.
Notice of Reasons for Refusal dated Nov. 15, 2018 for Japanese Patent Application No. 2018-071806.
Office Action for Chinese Patent Application No. 201280015466.8 dated Apr. 20, 2015 (with translation).
Office Action for Japanese Patent Application No. 2014-501276 dated Mar. 1, 2016 (with translation).
Office Action for Japanese Patent Application No. 2015-503186 dated Oct. 3, 2017 (with machine translation).
Office Action for Japanese Patent Application No. 2015-503186 dated Jun. 6, 2017 (with translation).
Office Action for U.S. Appl. No. 14/006,763 dated Dec. 15, 2016.
Office Action for U.S. Appl. No. 14/006,763 dated May 16, 2016.
Office Action for U.S. Appl. No. 14/006,763 dated Jul. 12, 2017.
Office Action for U.S. Appl. No. 14/348,533 dated Feb. 22, 2017.
Office Action for U.S. Appl. No. 15/400,978 dated Sep. 21, 2017.
Office Action in Japanese Patent Application No. 2015-503186 dated Aug. 2, 2016 (with translation).
Partial European Search Report issued in application 19167042.1 and dated Jul. 15, 2019.
Partial Supplementary European Search Report for European Patent Application No. 12760085.6 dated Jun. 1, 2015.
Agar, "An Obituary For Baxter's Vivia Home HD Machine," Home Dialysis Central, 2016, pp. 1-11, Home Dialysis Central, Madison, Wisconsin.
Agar, "Technology: What's Coming," Nocturnal Haemodialysis Program, Barwon Health, 2012, pp. 1-8, www.nocturnaldialysis.org/technology_whats_coming.html.
Fassbinder, "Experience with the Genius hemodialysis system," Kidney Blood Press Res., 2003, vol. 26(2), pp. 96-99 (Abstract only), Karger, Basel, Switzerland.
Heroux, "Aksys—Dialysis Technologists," Dialysis Technologists, 2005, pp. 1-5, https://www.tapatalk.com/groups/dialysistechnologists39151/aksys-t607.html.
Kjellstrand et al., "The Aksys personal hemodialysis system," Seminars in Dialysis, 2004, vol. 17(2), Abstract only, Wiley, Hoboken, New Jersey.
Office Action (Communication Pursuant to Article 94(3) EPC) dated May 10, 2021, issued in European Application No. 18215332.0.
Office Action (Examination Report No. 1) dated Jun. 1, 2021 for Australian Patent Application No. 2019228526.
Office Action (Examination Report No. 1) dated Jun. 1, 2021 for Australian Patent Application No. 2020244565.
Office Action (Examination Report No. 1) dated Jun. 1, 2021 for Australian Patent Application No. 2020244566.
Office Action (Examination Report No. 1) dated Jun. 1, 2021 for Australian Patent Application No. 2020244567.
Office Action (Notice of Reasons for Refusal) dated Mar. 1, 2022 for Japanese Patent Application No. 2020-200127.
Office Action (Notice of Reasons for Refusal) dated Mar. 22, 2022 for Japanese Patent Application No. 2020-545472.
Office Action (Notification of Examination) issued in German Application No. 112012001381.6 dated Mar. 30, 2022.
Office Action (Pre-Appeal Examination Report) dated Feb. 9, 2021 for Japanese Patent Application No. 2019-063926.
Schlaeper et al., "The Fresenius Medical Care Home Hemodialysis System," Seminars in Dialysis, 2004, vol. 17 (2), pp. 159-161, Wiley, Hoboken, New Jersey.
Unknown, "4008 H—Hemodialysis Machine Operating Instructions," Fresenius Medical Care AG, Software Version 4.3, May 1, 2005, pp. 1-365.
Unknown, "4008 S—Hemodialysis Machine Operating Instructions," Fresenius Medical Care, Software Version 4.5, Oct. 1, 2011, pp. 1-368.
Unknown, "4400HX Hot Water Disinfection Water Treatment Solutions for Hemodialysis," Mar Car Purification—A Cantel Medical Company, 2006, 4 pages.
Unknown, "Aquaboss EcoRO Dia 70—Portable water treatment for hemodialysis," Lauer Membran Wassertechnik, 2008, Rev. 4.53, Software version 4.00_12, pp. 1-144.
Unknown, "AquaUNO Single Station Reverse Osmosis Unit—Operation Instructions," Fresenius Medical Care, Jul. 1, 2006, Software Version: V2.05, pp. 1-116.
Unknown, "Baxter nixes Vivia home hemodialysis machine," Nephrology News & Issues, 2016, p. 1, Healio, https://www.healio.com/news/nephrology/20180227/baxter-nixes-vivia-home-hemodialysis-machine.
Unknown, "Conversion/Retrofit Kit—No. M37525—Connection of an AguaUNO or AquaC UNO H to a 4008" Fresenius Medical Care, 2012, pp. 1-8.
Unknown, "User and service manual—Single place reverse osmosis system—RO 4008," DWA GmbH & Co. KG, Oct. 1, 2008, pp. 1-39.
Unknown, "User Interface Design—PHD Personal Hemodialysis System for Aksys," Brochure, Stream Product Development, Inc., 2020, North Chelmsford, Massachusetts.
Unknown, "Xcorporeal, Inc Announces The XCR-6 Dialysis Platform For Self-Directed Kidney Hemodialysis," Med Device Online, 2008, pp. 1-2, Business Wire, San Francisco, California, https://www.meddeviceonline.com/doc/xcorporeal-inc-announces-the-xcr-6-dialysis-0001.
Extended European Search Report dated Feb. 17, 2021 for European Patent Application No. 18821268.2.
Office Action dated Mar. 24, 2020 issued in JP Patent App. No. 2019-063926.
International Preliminary Report on Patentability dated Sep. 10, 2020, issued in International Application No. PCT/US2019/019967.
Office Action dated Aug. 4, 2020, issued in Japanese Application No. 2019-063926.

(56) References Cited

OTHER PUBLICATIONS

Extended European Search Report dated Oct. 18, 2021, issued in European Application No. 19760761.7.
International Search Report and Written Opinion dated Oct. 24, 2018 issued in International Patent Application No. PCT/US2018/039188.
Office Action (Communication Pursuant to Article 94(3) EPC) dated Aug. 11, 2022 for European Patent Application No. 19167042.1.
Office Action for Japanese Patent Application No. 2014-501276 dated Aug. 9, 2022 (includes English translation).
Office Action for Japanese Patent Application No. 2020-200127, dated Apr. 11, 2023.
Office Action for Japanese Patent Application No. 2023-063941 issued on Feb. 27, 2024 (includes English language translation).

\* cited by examiner

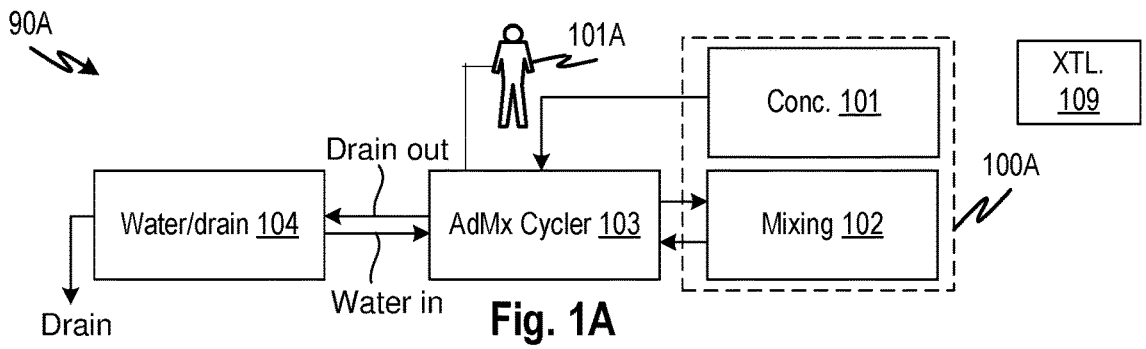

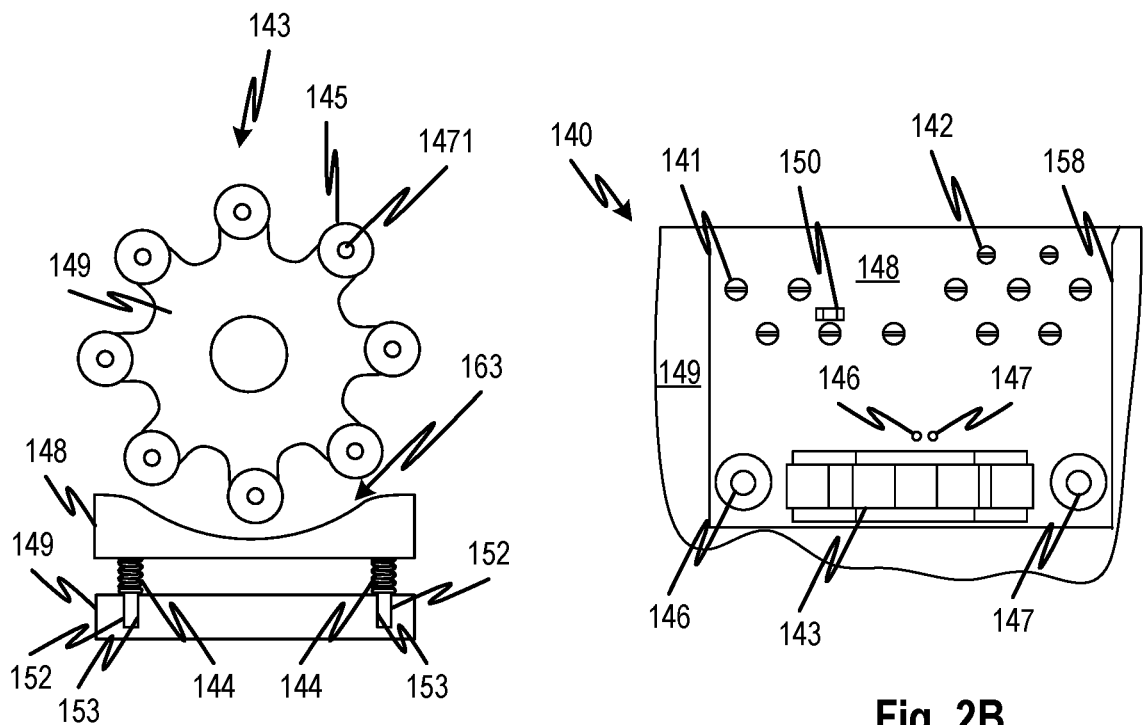
Fig. 2D
Fig. 2B
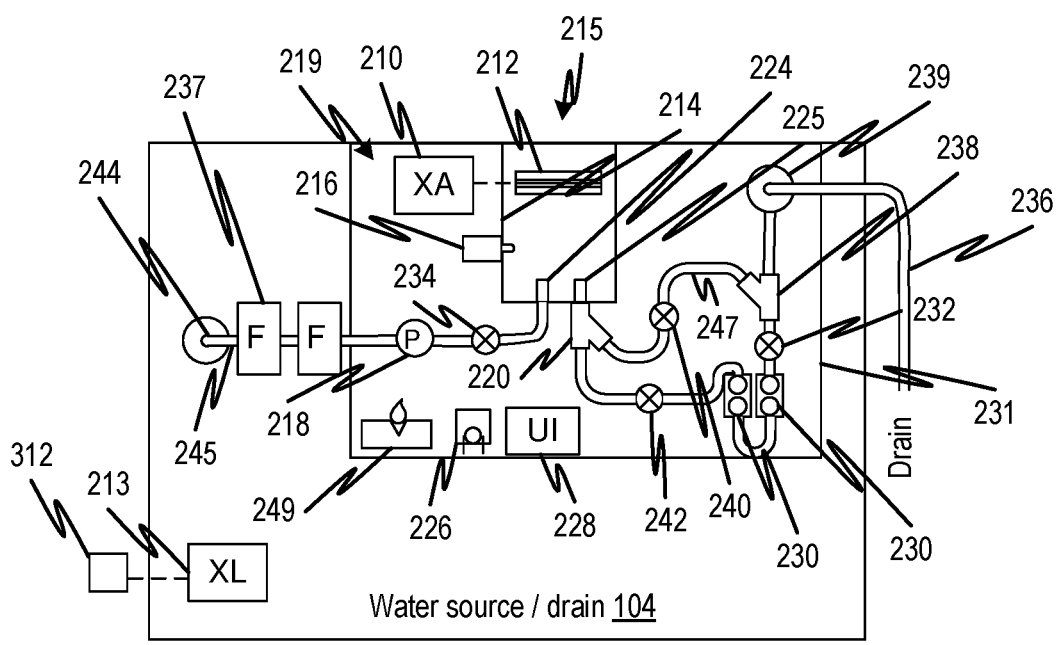
Fig. 2C

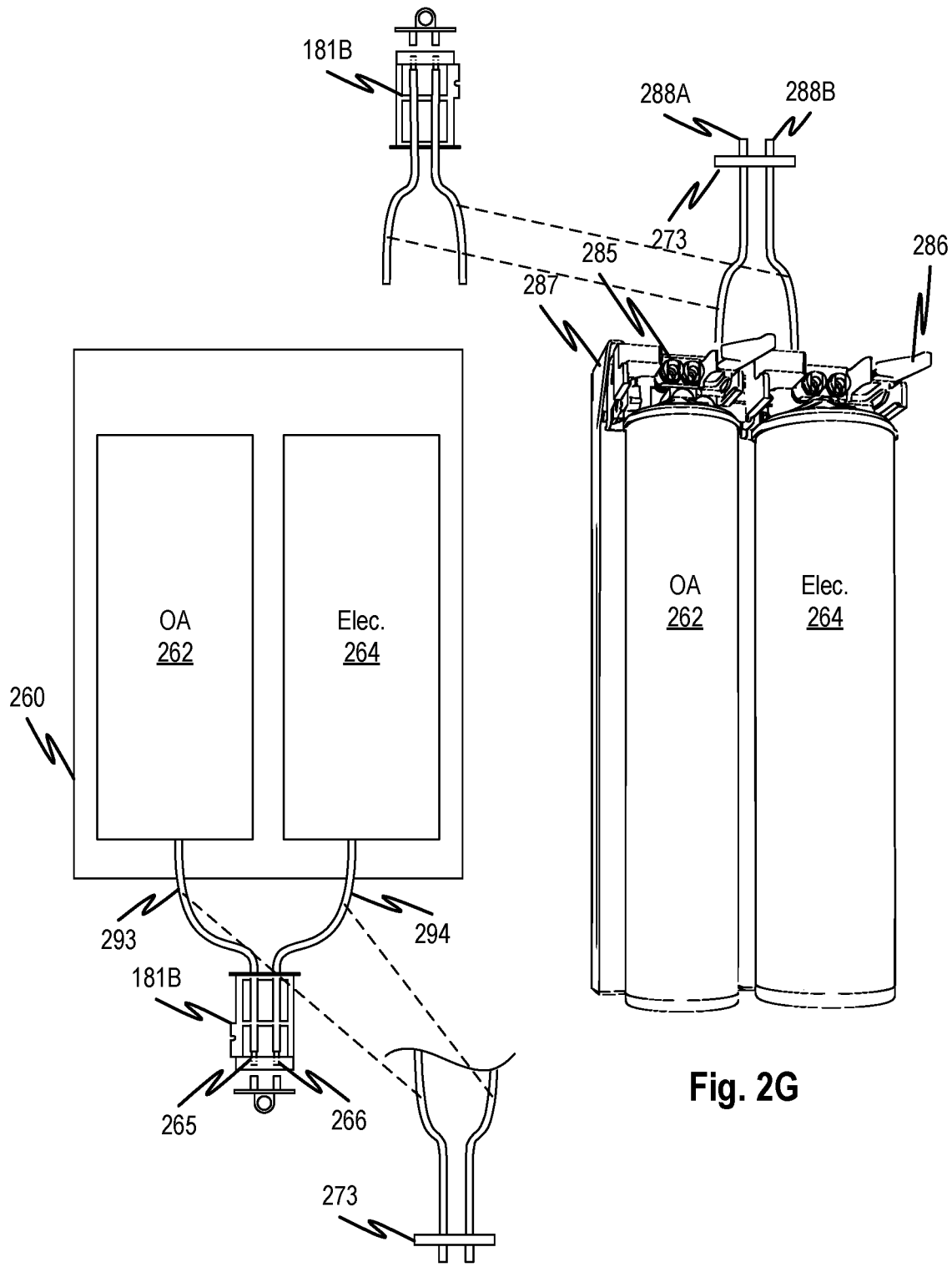

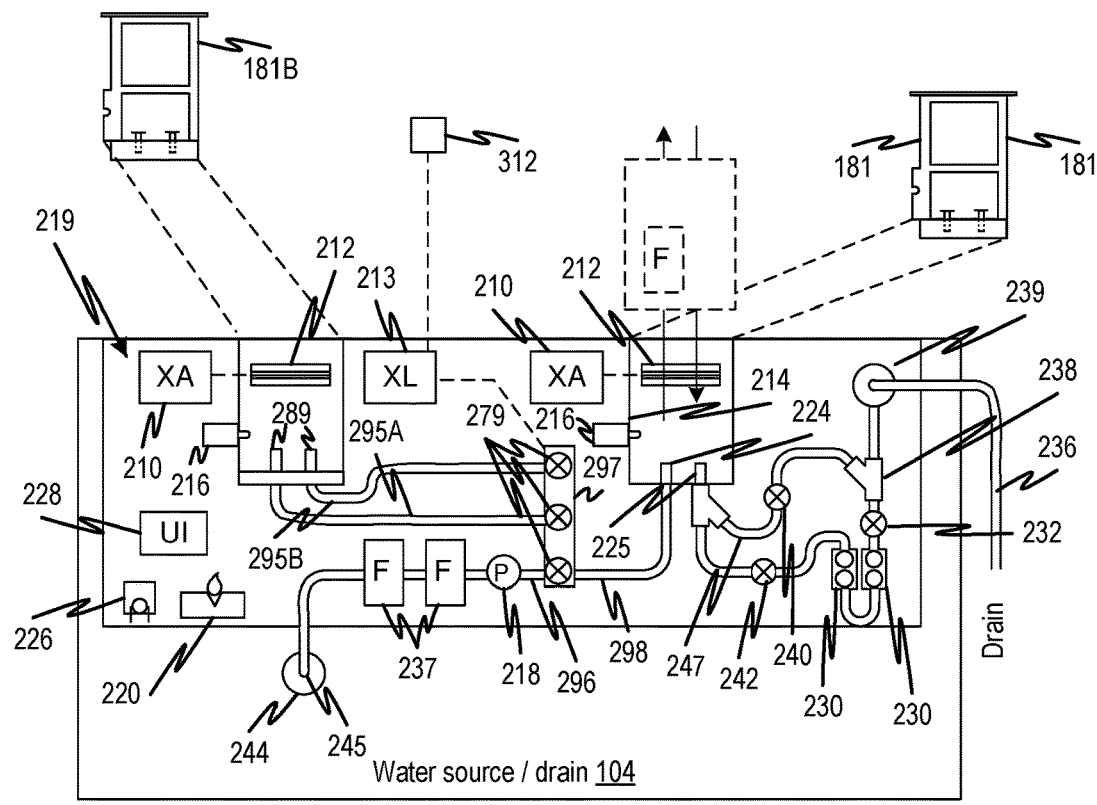
Fig. 2K
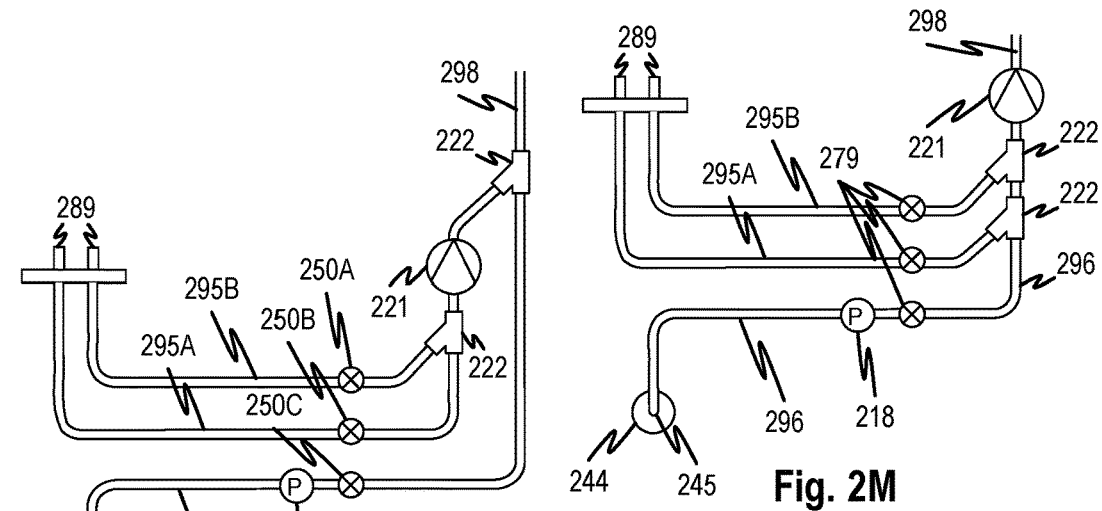
Fig. 2L
Fig. 2M
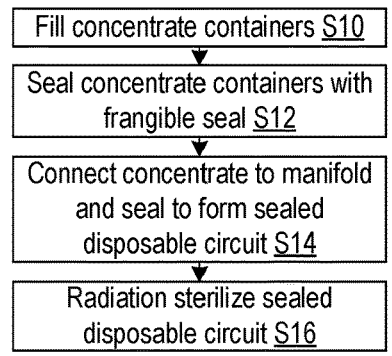
Fig. 3

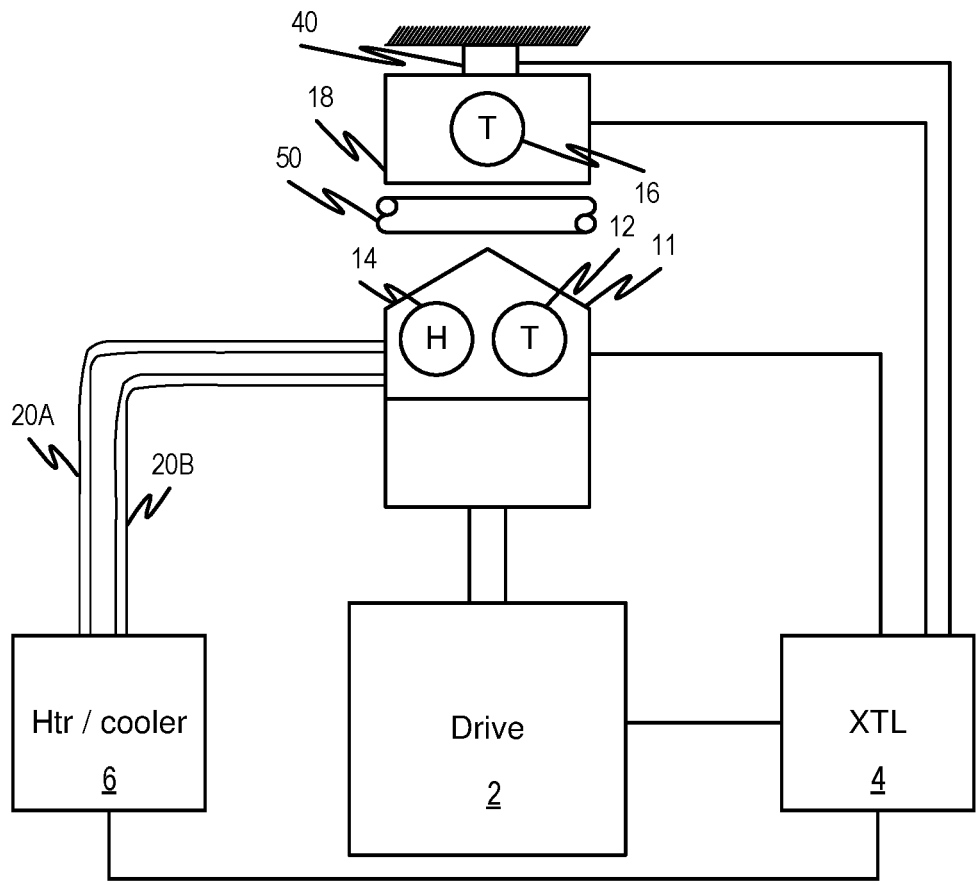
Fig. 6A
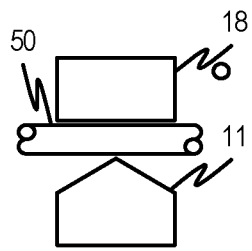 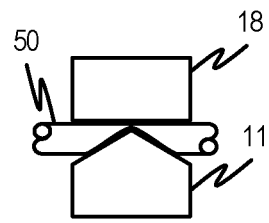 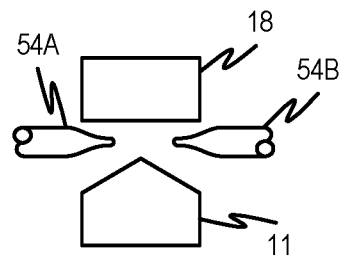
Fig. 6B  Fig. 6C  Fig. 6D

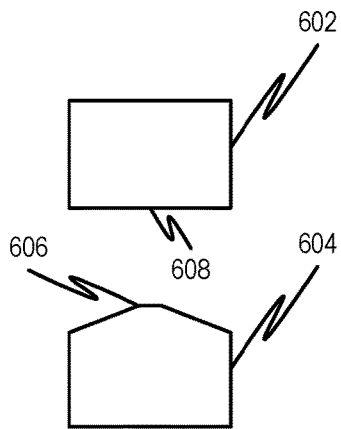
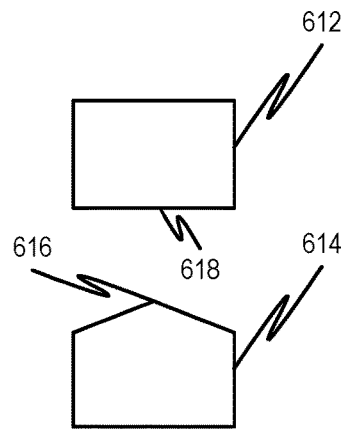
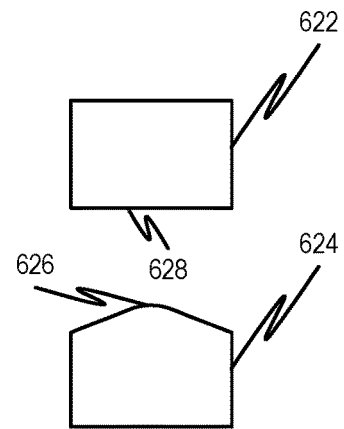
Fig. 7A    Fig. 7B    Fig. 7C
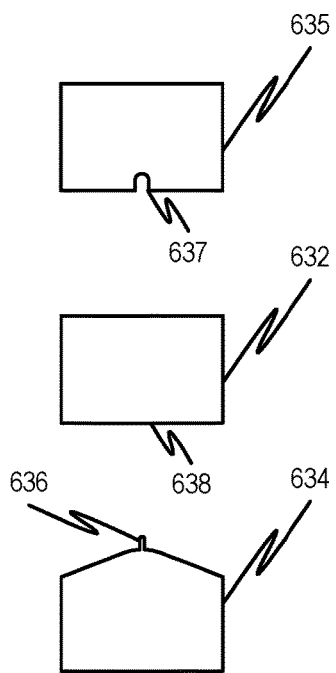
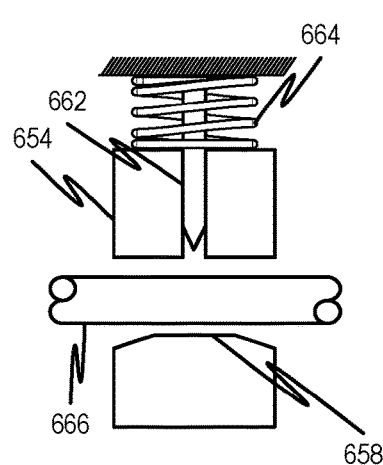
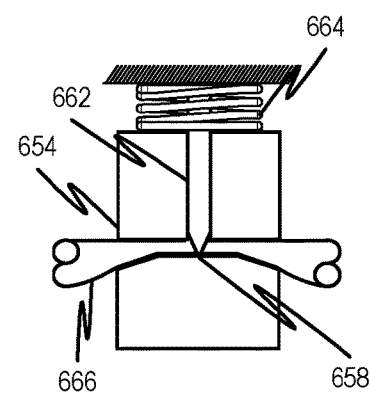
Fig. 7D    Fig 6E    Fig 6F
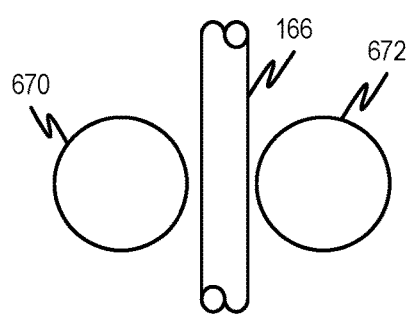
Fig 6G

PERITONEAL DIALYSIS FLUID PREPARATION AND/OR TREATMENT DEVICES METHODS AND SYSTEMS

CROSS REFERENCE TO RELATED APPLICATIONS

This Application is a U.S. national stage filing under 35 U.S.C. § 371 of International Application No. PCT/US2018/039188, filed Jun. 24, 2018 and published as International Publication Number WO2018237375A1 on Dec. 27, 2018, which claims the benefit of U.S. Provisional Application No. 62/524,492 filed Jun. 24, 2017, each of which are incorporated herein by reference in their entireties.

BACKGROUND

The disclosed subject matter relates generally to the peritoneal dialysis treatment of end stage renal failure and more specifically to devices, methods, systems, improvements, and components for preparing peritoneal dialysis solution and according to certain embodiments, also performing peritoneal dialysis. As used herein, the term "peritoneal dialysis solution admixer/cycler" refers to a system that generates peritoneal dialysis solution by admixing and, optionally, also performs a peritoneal dialysis treatment. Thus, peritoneal dialysis solution admixer/cyclers generate peritoneal dialysis, but may not perform a peritoneal dialysis treatment.

Peritoneal dialysis is a mature technology that has been in use for many years. It is one of two common forms of dialysis, the other being hemodialysis, which uses an artificial membrane to directly cleanse the blood of a renal patient. Peritoneal dialysis employs the natural membrane of the peritoneum to permit the removal of excess water and toxins from the blood.

In peritoneal dialysis, sterile peritoneal dialysis solution is infused into a patient's peritoneal cavity using a catheter that has been inserted through the abdominal wall. The solution remains in the peritoneal cavity for a dwell period. Osmotic exchange with the patient's blood occurs across the peritoneal membrane, removing urea and other toxins and excess water from the blood. Ions that need to be regulated are also exchanged across the membrane. The removal of excess water results in a higher volume of fluid being removed from the patient than is infused. The net excess is called ultrafiltrate, and the process of removal is called ultrafiltration. After the dwell time, the dialysis solution is removed from the body cavity through the catheter.

Peritoneal dialysis requires the maintenance of strict sterility because of the high risk of peritoneal infection.

In one form of peritoneal dialysis, which is sometimes referred to as cycler-assisted peritoneal dialysis, an automated cycler is used to infuse and drain dialysis solution. This form of peritoneal dialysis treatment can be done automatically at night while the patient sleeps. One of the safety mechanisms for such a peritoneal dialysis treatment is the monitoring by the cycler of the quantity of ultrafiltrate. The cycler performs this monitoring function by measuring the amount of fluid infused and the amount removed to compute the net fluid removal.

The peritoneal dialysis treatment sequence usually begins with an initial drain cycle to empty the peritoneal cavity of spent dialysis solution, except on so-called "dry days" when the patient begins automated peritoneal dialysis treatment without their peritoneal cavity filled with dialysis solution. The cycler then performs a series of fill, dwell, and drain cycles, typically finishing with a fill cycle.

The fill cycle presents a risk of over-pressurizing the peritoneal cavity, which has a low tolerance for excess pressure. In traditional peritoneal dialysis, a dialysis solution container is elevated to certain level above the patient's abdomen so that the fill pressure is determined by the height difference. Automated systems sometimes employ pumps that cannot generate a pressure beyond a certain level, but this system is not foolproof since a fluid column height can arise due to a patient-cycler level difference and cause an overpressure. A reverse height difference can also introduce an error in the fluid balance calculation because of incomplete draining.

Modern cyclers may fill by regulating fill volume during each cycle. The volume may be entered a controller based on a prescription. The prescription, which also determines the composition of the dialysis solution, may be based upon the patient's size, weight, and other criteria. Due to errors, prescriptions may be incorrect or imperfectly implemented resulting in a detriment to patient well-being and health.

SUMMARY

Peritoneal dialysis admixing and/or treatment devices, methods, and systems are disclosed. The systems, methods, and devices provide high-level guarantees of sterility and employs relatively inexpensive disposable components to provide pumping. Disclosed systems, methods, and devices and features thereof are adapted for point of use generation of medicament. In particular admixing systems that employ independently-replaceable long term concentrate are disclosed. Features are directed to assurance of sterility and accurate admixing of water and concentrate to generate ready-to-use medicaments and other benefits.

Objects and advantages of embodiments of the disclosed subject matter will become apparent from the following description when considered in conjunction with the accompanying drawings.

BRIEF DESCRIPTION OF THE DRAWINGS

Objects and advantages of embodiments of the disclosed subject matter will become apparent from the following description when considered in conjunction with the accompanying drawings.

FIGS. 1A-1D show peritoneal dialysis solution admixer/cyclers according to respective embodiments of the disclosed subject matter.

FIG. 1E shows a series testable filter arrangement that may be substituted for the filters employed in the embodiments of FIGS. 1A-1D.

FIG. 2B shows an actuator portion of a peritoneal dialysis solution admixer/cycler, according to embodiments of the disclosed subject matter.

FIG. 2C shows a connection platform between a pure water source and the peritoneal dialysis solution admixer/cycler, according to embodiments of the disclosed subject matter.

FIG. 2D shows an eight-roller peristaltic pumping actuator that permits the use of a straight pumping tube segment in a generally planar cartridge, employed as a feature of embodiments disclosed herein.

FIGS. 2F and 2G show a concentrate disposable component for use with embodiments of the disclosed subject matter.

FIGS. 2I, 2J, and 2K show respective embodiments of connection platforms between a pure water source and a separate concentrate source and the peritoneal dialysis solution admixer/cycler embodiments disclosed herein, according to embodiments of the disclosed subject matter.

FIGS. 2L and 2M show details of variations of the embodiments described with reference to FIG. 2K.

FIG. 3 shows a method of manufacturing a disposable circuit such as is disclosed in FIG. 2A.

FIG. 6A shows mechanical aspects and a control and sensor system for the cut-and-seal devices with actuation, temperature, and force control features, according to embodiments of the disclosed subject matter.

FIGS. 6B through 6G show various embodiments of cut-and-seal devices.

FIGS. 7A through 7D show various jaw arrangements for cut-and-seal devices according to different embodiments of the disclosed subject matter.

Figure 1F:
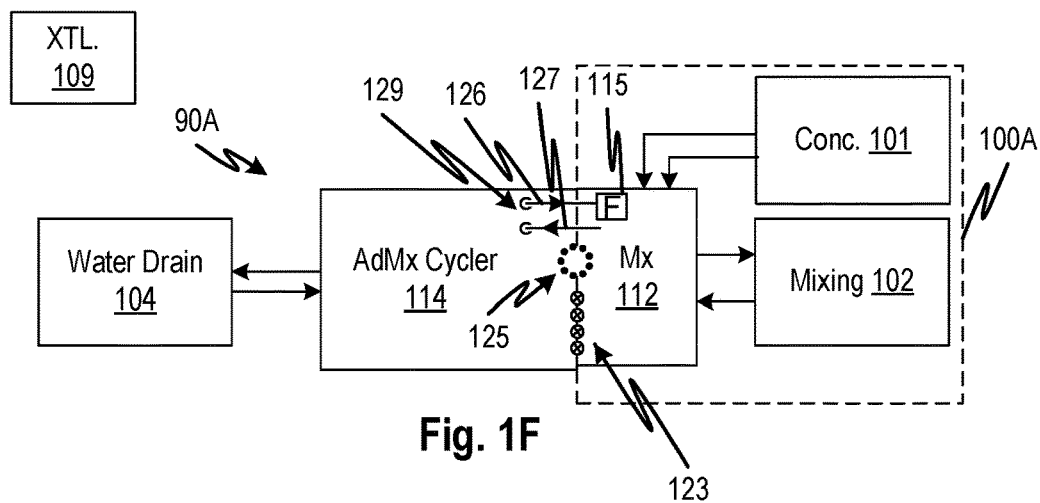
FIGS. 1F-1H show embodiments similar to those of FIGS. 1A-1D and elaborating further details thereof.

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

FIGS. 1A-1D show peritoneal dialysis solution admixer/cyclers according to respective embodiments of the disclosed subject matter. Referring now to FIG. 1A, medical fluid preparation and peritoneal dialysis solution admixer/cycler 90A includes a purified water source 104 that provides water suitable for peritoneal dialysis to a peritoneal dialysis solution admixer/cycler 103 which is connected to a disposable component 100A. The purified water source 104 also provides a connection to a drain (shown in FIG. 1A only, but similar in FIGS. 1B-1D). The peritoneal dialysis solution admixer/cycler 103 meters concentrate from one or more concentrate containers 101 (one container is shown but multiple containers may be present) and adds them to, and dilutes them with purified water in a mixing container 102. The concentrate containers 101 and mixing container 102 form parts of a single disposable which may also contain a switchable fluid circuit (not shown) that forms part of the disposable component 100A. Mixed dialysis solution (or other medicament) is pumped by the peritoneal dialysis solution admixer/cycler 103 through a connected line to a peritoneal dialysis treatment device such as a dialyzer or to a patient 101A, for example for peritoneal dialysis. The configuration of FIG. 1A allows the sterile concentrate and the fluid circuit and containers used for preparation, as well as short term storage, to be provided as a single sealed sterile disposable with a small predefined number of connections to external devices. These may include connections to the purified water source 104 and connections to the external medicament consumer. The small number of connections minimizes the risk of contamination. By diluting and mixing concentrate at the point of use, the volume of fluid that has to be stored at a peritoneal dialysis treatment location is also minimized. In a peritoneal dialysis embodiment, the disposable component 100A may be configured with sufficient concentrate to perform multiple fill/drain cycles of a single peritoneal dialysis treatment. For example, the disposable component 100A may have sufficient concentrate for multiple fill cycles of a daily automated peritoneal dialysis treatment (APD).

Referring now to FIG. 1B, a medical preparation and peritoneal dialysis solution admixer/cycler 90B is similar to the medical fluid preparation and peritoneal dialysis solution admixer/cycler 90A except that the disposable component 100B that has a fluid circuit for proportioning and diluting as well as delivering the product medicament does not contain the concentrate. This allows the size of the disposable component 100B, which is handled frequently, for example, daily, to be reduced in mass and easier for a patient and/or user to handle and store. It also can make the disposable component 100B more economical by reducing waste and providing packaging and manufacturing economies. To provide the concentrate, a separate disposable component 100E is provided which contains one or more concentrate containers 101. The disposable component 100E may have a large capacity and may be changed on a schedule that is much less frequent than the frequency of the replacement of the disposable component 100B. For example, the disposable component 100B may be replaced each time a daily peritoneal dialysis treatment is performed. It may be called a "daily disposable component." For example, the disposable component 100E may be replaced once every month so it may be called a "monthly disposable." The disposable component 100B may also have, as part of the fluid circuit included therein, a sterilizing filter 115 of a type that has an air-line 118 to permit the pressure testing of a membrane thereof. The latter type of filter test may be performed automatically by a controller of the peritoneal dialysis solution admixer/cycler 103 on a schedule that is more frequent than the replacement schedule for the disposable component 100E. In embodiments, the sterilizing filter 115 may be integrated, and therefore, replaced with, the disposable component 100B. This allows the sterilizing filter 115 to be sealed and sterilized with the disposable component 100B and mixing container 102 as a single unit along with the switchable fluid circuit (not shown). Note details of a suitable configuration for a switchable fluid circuit may be found in International Patent Application Publication WO2013141896 to Burbank, et al.

A function provided by the sterilizing filter 115 is to provide safety given that a new sterile disposable component 100B is attached to the concentrate 101 for each peritoneal dialysis treatment. A similar filter may be employed in all the embodiments for the line indicated at 107 conveying the purified water to the peritoneal dialysis solution admixer/cycler 103. Since a new connection is required each time the disposable component 100B is replaced, there is a risk of contamination from the new connection. The sterilizing filter 115 (and others) can be provided as a sterile barrier to protect the sterile interior of the disposable component 100B, thereby ensuring that any contamination resulting from the newly-made connection does not enter the disposable component 100B interior. In addition, the automatic testing of the filter provides assurance that the sterilizing filter 115 integrity has provided the expected sterile fluid. Thus, the testability functions as a guarantee of the filter's sterilizing function. Testing of sterilizing filters using pressurized air testing can be done in various ways, for example, a bubble point test can be performed. Alternatively, a pressure decay test can be done where fluid is pumped across the membrane and the pressure drop measured and compared with a pressure drop representative of an intact filter or pressure is increased on one side, pumping stopped, and the rate of decay of pressure compared to a predefined curve representative of an intact filter. Other means of testing filter integrity may be used, for example, concentrates can include a large-molecule excipient whose presence can be detected using automatic chip-based analyte detection (e.g., attachment of fluid samples to selective fluorophore after flowing through the filter and optical detection after concentration). A feature of the embodiments that use a filter to provide the guarantee, as mentioned, is that the filter forms part of a sterilized unit that is otherwise hermetically sealed or protected by one or more additional sterilizing filters. Thus, in embodiments, the entire sealed and sterilized circuit may have sterilizing filters (1) at all openings to its interior or at least (2) at all openings to which fluid is admitted from the external environment.

Referring now to FIG. 1C, a medical preparation and peritoneal dialysis solution admixer/cycler 90C is similar to the medical fluid preparation and peritoneal dialysis solution admixer/cycler 90B in that the disposable component 100C that has a fluid circuit for proportioning and diluting as well as delivering the product medicament does not contain the concentrate. As in peritoneal dialysis solution admixer/cycler 90B, a separate disposable component 100F is provided which contains one or more concentrate containers 101, in this example, a first concentrate container 105A and a second concentrate container 105B are shown. These may be in the form of canisters held by a single packaging wrapper 105C or they may be replaced separately when they expire. As in the peritoneal dialysis solution admixer/cycler 90B, the disposable component 100C may have a large capacity and may be changed on a schedule that is much less frequent than the frequency of the replacement of the disposable component 100B. For example, the first concentrate container 105A and/or second concentrate container 105B may be sized to be replaced on a monthly basis. In the medical fluid preparation and peritoneal dialysis solution admixer/cycler 90C, the disposable component 100C may also have, as part of the fluid circuit included therein, two sterilizing filters (collectively indicated as the sterilizing filter 115), each of the type that has an air-line 118 to permit the pressure-testing of a membrane thereof. Each of the concentrates from first concentrate container 105A and second concentrate container 105B may thereby be sterilizing filtered and the filter tested for each separately. As in the peritoneal dialysis solution admixer/cycler 90B, this configuration allows the sterilizing filters 115 to be sealed and sterilized with the disposable component 100C and mixing container 102 as a single unit along with the switchable fluid circuit (not shown). As in any of the embodiments a sterilizing filter may be used in the water line as indicated at 107.

Referring now to FIG. 1D, a medical preparation and peritoneal dialysis solution admixer/cycler 90D is similar to the medical fluid preparation and peritoneal dialysis solution admixer/cycler 90C in that the disposable component 100C that has a fluid circuit for proportioning and diluting as well as delivering the product medicament does not contain the concentrate. As in peritoneal dialysis solution admixer/cycler 90C, a separate disposable component 100G is provided which contains a first concentrate container 105A and a second concentrate container 105B. As in any of the embodiments, the number of concentrates may be greater or fewer. The concentrates may be held in the canisters which may have a single packaging wrapper 105C or they may be replaced separately when they expire. As in the peritoneal dialysis solution admixer/cycler 90C, the disposable component 100G may have a large capacity such that it can be replaced on a schedule that is much less frequent than the frequency of the replacement of the disposable component 100D. For example, the first concentrate container 105A and/or second concentrate container 105B may be sized to be replaced on a monthly basis. In the medical fluid preparation and peritoneal dialysis solution admixer/cycler 90D, the disposable component 100D may also have, as part of the fluid circuit included therein, the sterilizing filter 115, also of the type that has an air-line 118 to permit the pressure testing of a membrane thereof. To sterile-filter each of the concentrates from first concentrate container 105A and second concentrate container 105B, a connection platform allows the peritoneal dialysis solution admixer/cycler 103 to draw purified water, first concentrate container 105A or second concentrate container 105B selectively by closing a valve on all but one of these at a time by the connection platform 106 under control of the peritoneal dialysis solution admixer/cycler 103. As in the peritoneal dialysis solution admixer/cycler 90B, this configuration allows the sterilizing filter 115 to be sealed and sterilized with the disposable component 100D and mixing container 102 as a single unit along with the switchable fluid circuit (not shown). The switching fluid circuit of the connection platform 106 may be part of a disposable that is replaced with the first concentrate container 105A and second concentrate container 105B.

In the present and any of the embodiments, the long-term concentrate containers (e.g., monthly disposable) may be replaced on separate schedules so they need not be packaged as a single disposable. This may provide further economy when one concentrate is used at a lower rate by some patients than others, thus allowing the concentrate to be consumed fully before replacing.

It should be evident that there is the potential for the reduction of waste of concentrate by structuring the batch preparation components to permit the changing of concentrates independently of each other and at intervals that cover multiple peritoneal dialysis treatment sessions. Each concentrate container can be used until exhaustion. For embodiments, exhaustion may be defined to be a condition where insufficient concentrate remains in a single container to permit the preparation of a full batch of peritoneal dialysis fluid, a full batch, in embodiments being a quantity of concentrate component sufficient for a single fill cycle. For additional embodiments, Exhaustion may be defined to be a condition where insufficient concentrate remains in a single container to permit the preparation of a full batch of peritoneal dialysis fluid, a number of full batches, in embodiments being a quantity of concentrate component sufficient for full peritoneal dialysis treatment. If two concentrates are mixed to form a batch, each component concentrate may be changed out when the prescription's required contribution of that concentrate to a single batch beyond the remaining volume in the particular container. The residual volume threshold associated with this insufficiency is a fixed volume, so that its percentage of the total volume available from a full container is smaller for a large container than for a smaller container. Thus, in embodiments where the concentrate container is replaced only when the threshold is reached, which container holds large total volume, for example, enough for multiple fill cycles, or better, enough for multiple peritoneal dialysis treatments each including multiple fill cycles, the total waste is much smaller than a disposable component containing concentrate for a single peritoneal dialysis treatment. An example of the latter is discussed below with reference to FIGS. 8A and 8B. In addition, since each concentrate container can be replaced separately, the fixed residual thresholds of the multiple concentrate containers are independent of each other because each container can be replaced independently of the other. In contrast, in the embodiments of FIGS. 8A and 8B, if one container reaches the minimum volume before the other, the contents of neither concentrate container can be used further.

In embodiments, the concentrate containers are sized to permit a single peritoneal dialysis treatment. For convenience and convention, a single peritoneal dialysis treatment would be considered a single day's worth of peritoneal dialysis treatment, for example, a series of nocturnal PD cycles ending with a fill. So, a single day's peritoneal dialysis treatment is equal to a sufficient quantity of fluid to perform multiple fill drain cycles. Embodiments in which the concentrate containers are sized for a single day's peritoneal dialysis treatment differ from those described with reference to the embodiments of FIGS. 8A and 8B in that the concentrates can be changed independently thereby achieving a potential savings of a first concentrate that is used at a rate such that a residual volume of the first concentrate can be used more fully as described above. More specifically, if the concentrate containers are sized such that batches of at least predefined prescriptions require more of a first concentrate component than of a second concentrate component and such that at least one batch, or at least one day's worth of batches can be completed while leaving sufficient residual concentrate of the second component to make at least one additional batch, or one additional day's worth of batches, after replacing the first concentrate component, then a savings of the second concentrate may be enjoyed. In embodiments, the total concentrate of the most heavily used container of a multiple-component concentrate system is at least sufficient for:

1. Multiple batches, a batch being sufficient for a single peritoneal cycle (fill volume of a peritoneum of a predefined class of patient (e.g., child, adult, adult of a certain size, etc.);
2. Same as 1, but where the multiple batches are sufficient for a single peritoneal dialysis treatment of multiple fill-drain cycles;
3. Same as 2, but the most heavily used concentrate container is sufficient for making enough dialysis solution for multiple peritoneal dialysis treatments;
4. Same as 2, but the most heavily used concentrate container is sufficient for making enough dialysis solution for multiple days' worth of peritoneal dialysis treatments if a single day's worth is not identical to a single peritoneal dialysis treatment's worth;
5. A full week's worth of peritoneal dialysis treatments; or
6. A full month's worth of peritoneal dialysis treatments or some other interval on the order of a month or multiple months.

Figure 1G:
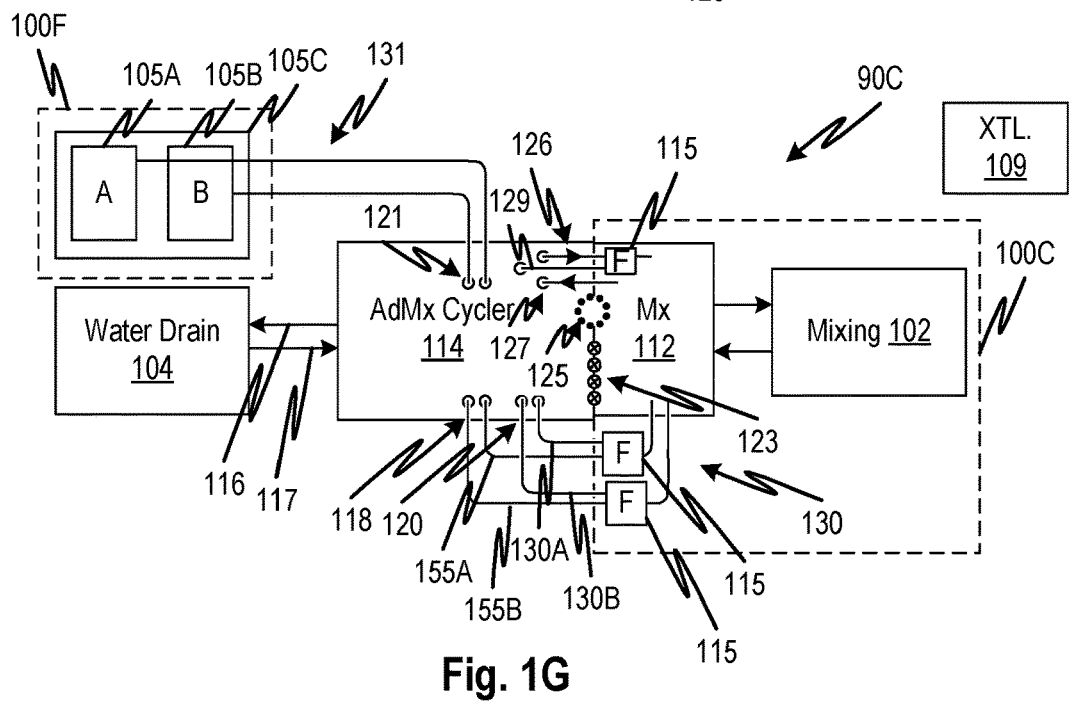
Figure 1H:
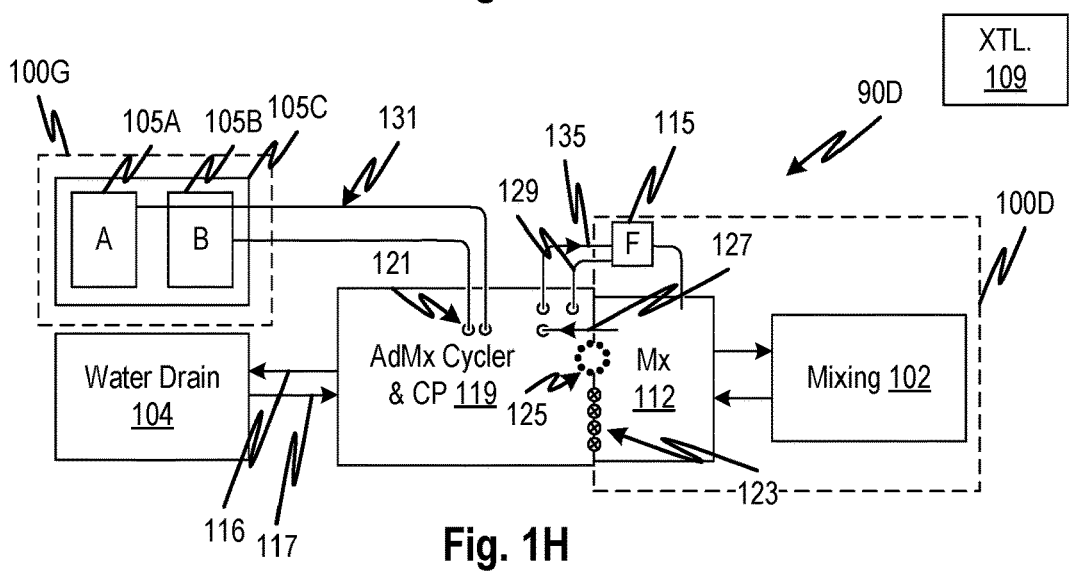

FIGS. 1F-1H show embodiments similar to those of FIGS. 1A-1D and elaborating further details thereof. Referring now to FIG. 1F, a fluid circuit is indicated at 112. The fluid circuit engages with the peritoneal dialysis solution admixer/cycler 114 by means of valve actuators 123 and one or more pumping actuators 125 which engage the fluid circuit elements of the fluid circuit 112 without wetting the actuator components. For example, a type of valve actuator such as a linear-motor driven pinch clamp may close and open tubing for flow therethrough and peristaltic pump rollers may engage pumping tube segments. The configuration is not limited to such examples, and many are known in the art, any of which may be used in the present embodiment. The fluid circuit 112 has water suitable for peritoneal dialysis and drain lines 126, 127. The water suitable for peritoneal dialysis flowing through a line with a sterilizing filter 115 according to any of the disclosed embodiments including a testable filter and two sterilizing filters in series. The only connections that need to be made for supplying fluid or draining fluid are connections indicated at 129. The water suitable for peritoneal dialysis and drain lines 126, 127 may be formed as part of the fluid circuit 112. In embodiments, the fluid circuit 112, concentrate container(s) 101, and mixing container 102 may be pre-connected to form a complete disposable fluid circuit 100A including concentrate.

Referring now to FIG. 1G, further details of the peritoneal dialysis solution admixer/cycler 90C are shown. The separate disposable component 100F contains concentrate containers 105A and 105B and connects to the peritoneal dialysis solution admixer/cycler 114 by connectors 121, which may include a double connector as described in embodiments described herein or other types. The peritoneal dialysis solution admixer/cycler 114 has pumping actuators 125 and valve actuators 123 that engage the fluid circuit 112. Here the peritoneal dialysis solution admixer/cycler 114 provides a pass-through connection for the concentrate while the sterilizing filters 115 on the concentrate lines 130 form part of the disposable component 100C, which includes the fluid circuit 112 and mixing container 102. That is, the peritoneal dialysis solution admixer/cycler 114 connects the concentrate lines 131 respectively to the concentrate lines 155A and 155B of the fluid circuit 112. Here also, connectors for air-lines 130A and 130B are provided to the peritoneal dialysis solution admixer/cycler 114 where an air pump (not shown) can generate a positive pressure and a pressure sensor can measure the positive pressure. A filter integrity test may be done after flowing fluid into the fluid circuit. During set-up, the disposable component 100C may be connected by connecting water suitable for peritoneal dialysis and drain lines 126, 127, concentrate lines 155A and 155B and air-lines 130A and 130B, while the connectors 121 can remain in place through the entire long-term disposable cycle, that is, until the separate disposable component 100F is expired. Since the latter is replaced much less frequently, the connectors 121 can remain in place for a relatively long period, and frequent changes can be limited to changing connectors 122, 120, and connectors for water suitable for peritoneal dialysis and drain lines 126, 127 as well as the air-lines 130A and 130B. In embodiments, for convenience, all of these connections can be provided in the form of ganged connectors to make and unmake multiple connections at once. The concentrate containers 105A and 105B may connect to a connection platform (not shown as a unit but may include the connectors and a support for the concentrate containers 105A and 105B) and a holder for the by the dialysis solution admixer/cycler 114. See further connection platform embodiments for details.

Referring to FIG. 1H, a simplified arrangement becomes possible if the disposable component 100G is connected to the peritoneal dialysis solution admixer/cycler 114 by connectors 121, but all concentrates and water flow into the fluid circuit 112 via the fluid line 135 and all of these fluids are filtered by sterilizing filter 115. To provide this, a connection platform may be provided. The connection platform may have its own controller. The connection platform and peritoneal dialysis solution admixer/cycler are collectively indicated at 119. The connection platform portion of admixer/cycler and connection platform 119 may be as described with reference to FIGS. 2K through 2M, for example. The connection platform portion of admixer/cycler and connection platform 119 selects one of the fluids at a given time by closing off the others and opening a fluid path to the selected one of water, concentrate A, and concentrate B. As indicated, here and in any embodiments, further or fewer concentrates may be used. A drain line 135 is present. A communications interface may be provided to allow commands to be sent from the fluid circuit 112 to the peritoneal dialysis solution admixer/cycler and connection platform 119.

Figure 2A:
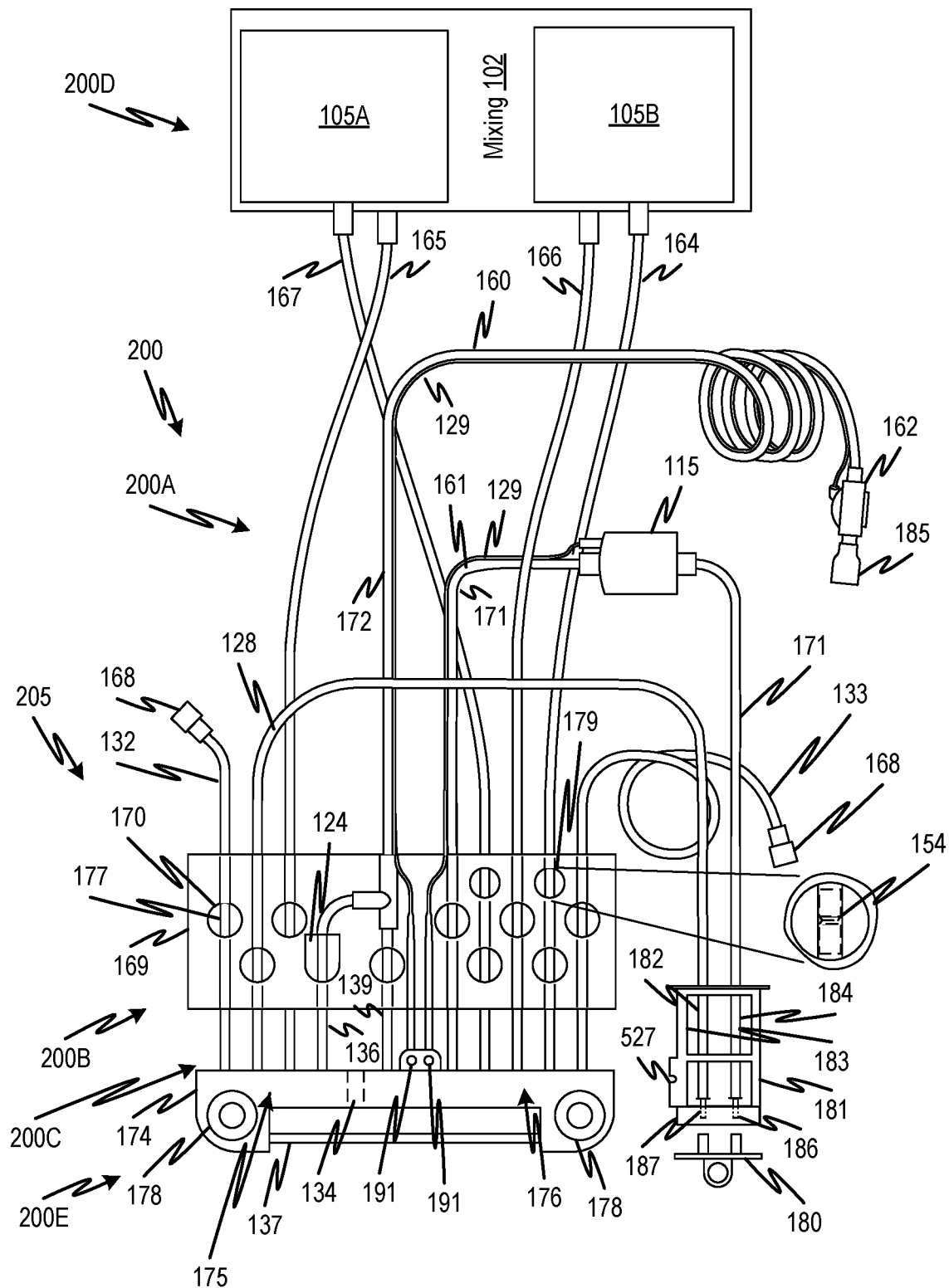
FIG. 2A shows a disposable fluid circuit for use with peritoneal dialysis solution admixer/cyclers of certain embodiments disclosed herein.

FIG. 2A shows a disposable fluid circuit 200 with fluid lines and components 200A and a cartridge portion 205 containing a fluid flow director portion 200B and a manifold portion 200E. The disposable fluid circuit 200 is used as a replaceable disposable component with a peritoneal dialysis solution admixer/cycler according to embodiments disclosed herein. The present disposable fluid circuit 200 may be used with the peritoneal dialysis solution admixer/cycler 90A, for example. Two concentrate containers 105A and 105B and a mixing container 102 are connected as a pre-connected unit with other parts of the fluid circuit. The two concentrate containers 105A and 105B and mixing container 102 may be provided as a welded double panel sheet with welded seams that define the respective chambers. The mixing container 102 has two lines, an inflow line 165 and an outflow line 166. A first concentrate container 105A container has 167, which may be pre-connected and a second concentrate container 105B line 164, which may be pre-connected. The present embodiment is for a peritoneal dialysis solution admixer/cycler and has a pre-connected fill-drain line 160 with a dialysis solution line 172 attached to an air-line 129. The latter may be formed as a single unit by co-extrusion. The air-line 129 attaches to a pressure-sensing pod 162 located at a distal end of the pre-connected fill-drain line 160. A connector 185 at the distal end of the pre-connected fill-drain line 160 is sealed. Another double line 161 has an air-line 129 and a fluid line 171. The fluid line 171 receives fluid from peritoneal dialysis solution admixer/cycler 114 and the air-line is used for testing the membrane of the filter. The two air-lines 129 connect to respective ports 191 that automatically connect in the actuator portion 140 of any of the suitable peritoneal dialysis solution admixer/cycler embodiments. The actuator portion 140 may be is described with reference to FIG. 2B. Sample ports are provided at 168 at the ends of sample fluid lines 132 and 133 for extracting fluid from respective chambers 175 and 176 of a manifold 174. The two chambers 175 and 176 are separated by a barrier 134 and connected by a pumping tube segment 137. Pressure pods 178 are installed in each of the two chambers 175 and 176 to measure pressure on the suction and pressure sides of the pumping tube segment 137. The dialysis solution line 172 has two branches 136 and 139. A waste line 128 and the fluid line 171 connect via a double connector 181. Lines 132, 128, 165, and branch 136 connect to chamber 175. Lines 133, 164, 166, 167, 171 and branch 139 connect to chamber 176.

The double connector 181 supports lines 171 and 128 and provides a pair of connectors 186 and 187 to permit connection of lines 171 and 128 to fill and drain line ports on the peritoneal dialysis solution admixer/cycler 114. The connectors 186 and 187 are sealed by a cap 180. A recess 527 (See FIGS. 5A, 5B) to engage a détente pin (not shown, but may be a spring-biased pin in the opening that receives the double connector 181) provides tactile confirmation of full engagement of the double connector 181. The double connector 181 has a window 183 that provides access to a cut and seal actuator (not shown in this drawing but indicated at 212 in FIGS. 2I through 2K). When the segments 182 and 184 of lines 171 and 128 are cut, the double connector can remain in place sealing the fill and drain line ports until it is removed immediately prior to connecting a fresh double connector 181. This provides a barrier to prevent contaminants from entering the fill and drain line ports, which in turn protects the sterile fluid path used by the peritoneal dialysis solution admixer/cycler or connection platform.

The first concentrate container 105A and concentrate container 105B are both sealed by a frangible seal 154 in each of the lines 164 and 167. The seal is fractured automatically by an actuator after the manifold cartridge 205 is loaded into a receiver that engages it with the interface shown in FIG. 2B. Holes 170 are provided in a cartridge support 169 that holds the lines in predefined positions. Holes 170 provide access to pinch actuators that selectively close and open the lines 177. Certain lines such as lines 177 engage with valve actuators so that they function as valve segments. Holes 179 provide access to actuators that fracture the frangible seals 154. Note that the cartridge support 169 is bridged to the manifold 174 by a battery of tubes indicated collectively at 200C. Even though the polymer of the tubes is flexible, their lengths, number, are such that the overall structure including the cartridge support 169 and the manifold 174 is sufficiently stiff may be readily inserted in a receiving slot.

FIG. 2B shows an actuator portion 140 of a peritoneal dialysis solution admixer/cycler, according to embodiments of the disclosed subject matter. Referring to FIG. 2B, a receiving slot 158 receives the cartridge portion 205 and aligns it with the various actuators and sensors now identified. The various actuators and sensors include pinch clamp actuators 141 that selectively press against selected tubes to provide a valve function. The actuators and sensors further include frangible seal actuators 142 that fracture frangible seals 154 in the concentrate lines that contain them. The frangible seal actuators 142 may be activated simultaneously to open the lines between the pump and the concentrate containers once the pump (e.g., eight-roller peristaltic pump 143) is engaged with the pumping tube segment 137. The actuators and sensors further include an air sensor 150, for example an optical air sensor, that wraps partly around the tube segment of branch 136 in the upper portion of the hole indicated at 124. Ports 146 and 147 connect a vacuum or pressure pump to the respective ports 191.

FIG. 2C shows connection platform 219 that serves as an interface between a pure water source and the peritoneal dialysis solution admixer/cycler, according to embodiments of the disclosed subject matter. Connection platform 219 is an embodiment that may provide for connection to water and drain lines 116 and 117 of embodiments of FIGS. 1G and 1H as well as connectors for the concentrate containers 105A and 105B for interfacing with the peritoneal dialysis solution admixer/cycler 114. The connection platform 219 permits the purified water source 104 to be connected to different devices, such as different peritoneal dialysis treatment devices. Shown here is a configuration adapted for peritoneal dialysis medicament preparation, and optionally peritoneal dialysis treatment also.

Water from the purified water source 104 is received in water line 245 via connection 244 and flows through ultrafilters 237. Pressure of the water suitable for peritoneal dialysis supply is monitored by a pressure sensor 218. A valve 234 selectively controls the flow of water suitable for peritoneal dialysis to a double connector 215. The purified water source terminates at a purified water connector 224 of the double connector 215. The double connector 215 also has a drain terminal connector 225 which splits at a junction 220 into a path that flows to a pair of conductivity sensors 230 and then merges at junction 238 to proceed to a drain 236 and a path that flows directly to the drain 236. The selected path is controlled by valves 232, 240, and 242 which are controlled by a controller 210. The double connector 181 previously described is received in a slot 214 where connections are made to the purified water connector 224 and drain terminal connector 225. A détente mechanism 216 provides tactile and audible feedback to the operator when a home (fully connected) position of the double connector 181 is made by inserting into the receiving slot 214. The receiving slot 214A has a cutting and sealing actuator 212 driven by a controller 210 that cuts the tubes through the window of double connector 181. A connector 239 serves as an adapter to permit connection to various types of drains. The connection platform 219 is also provided with sensors including a moisture sensor 249 located to detect leaking fluid in the connection platform 219, a tilt sensor 226 to indicate the proper orientation of the connection platform 219, and a user interface 228 to interact with the controller 210. The connection platform 219 may be received in a receiving slot 231 and may be formed as a unitary replaceable component. If sterility or leakage problems arise, the connection platform 219 can be replaced easily.

FIG. 2D shows an eight-roller peristaltic pumping actuator 143 that permits the use of a straight pumping tube segment in a generally planar cartridge, employed as a feature of embodiments disclosed herein. The rollers 145 are attached to a rotor that has recesses to permit clearance for the bulge of an adjacent pumping tube segment positioned between a race 148 and the rollers 145. The rollers 145 are unsprung, unlike other peristaltic pump rollers, and rotate on fixed bearings 147I. Instead, the race 148 is sprung by springs 144 which urge the race against a pumping tube segment pinched by the rollers 145. This is a particular embodiment of a pump and at least some of the embodiments are not limited based on whether the rollers or race are sprung. Either the rotor 149 can be moved toward the race 148 to engage a pumping tube segment, or the race 148 can be moved toward the rotor 149. A sufficient gap at 149 during loading allows a cartridge, such as cartridge portion 205 with a pumping tube segment to be slid in with no interference. The race 148 is constrained to tilt (in the plane of the drawing) and translate up and down in the plane of the drawing by pins 152 received in guides 153.

Figure 2E:
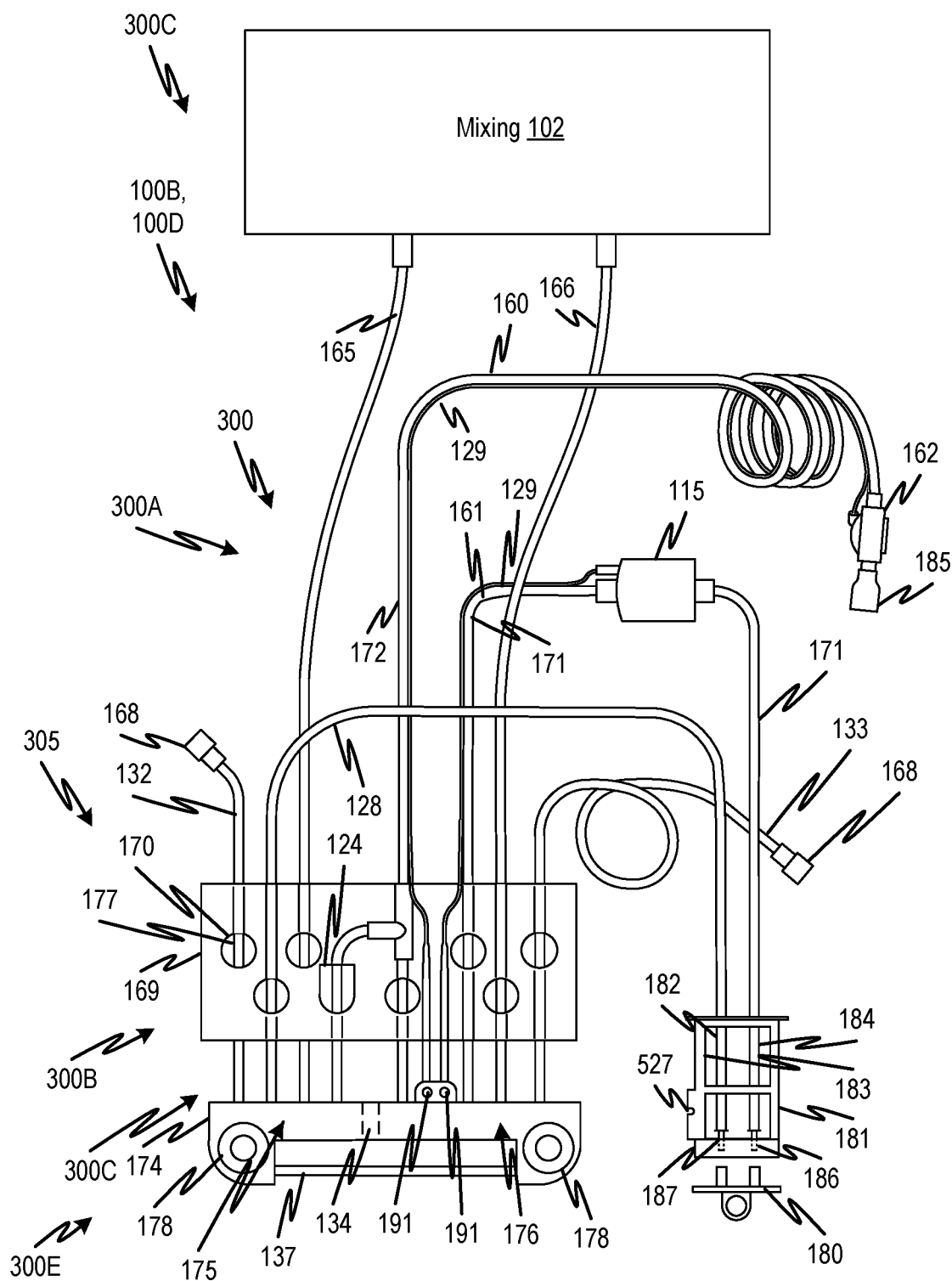
FIG. 2E shows a disposable fluid circuit for a peritoneal dialysis solution admixer/cycler according to embodiment of the disclosed subject matter in which concentrates are extracted from a disposable component that is separate from the cycler/preparation fluid circuit.

FIG. 2E shows a disposable fluid circuit for a peritoneal dialysis solution admixer/cycler according to an embodiment of the disclosed subject matter in which concentrates are extracted from a disposable component that is separate from the cycler/preparation fluid circuit. A disposable fluid circuit 300 has fluid lines and components 300A and a cartridge portion 305 containing a fluid flow director portion 300B and a manifold portion 300E. The disposable fluid circuit 300 is for use with peritoneal dialysis solution admixer/cyclers of certain embodiments disclosed herein. The present disposable is an embodiment that may be used with the peritoneal dialysis solution admixer/cycler 90B or 90D, for example, where two concentrate containers 105A and 105B (not shown in this drawing but shown in FIGS. 1B and 1H—again, only as examples so other features of the peritoneal dialysis solution admixer/cycler are not limiting of the disposable fluid circuit 300) are provided as a separate unit from disposable fluid circuit 300, which has a mixing container 102 and no concentrate containers. The mixing container 102 may be provided as a welded double panel sheet with welded seams that define the chambers. The mixing container 102 may have two lines, an inflow line 165 and an outflow line 166. In alternative embodiments, the mixing container 102 may have only a single line for both inflow and outflow.

The present embodiment is for a peritoneal dialysis solution admixer/cycler and has a pre-connected fill-drain line 160 with a dialysis solution line 172 attached to an air-line 129. The latter may be formed as a single unit by co-extrusion. In alternative embodiments, the fill-drain line may be separate and connectable with a separate connector. In the present embodiment, the air-line 129 attaches to a pressure-sensing pod 162 located at a distal end of the pre-connected fill-drain line 160. A connector 185 at the distal end of the pre-connected fill-drain line 160 is sealed. Another double line 161 has an air-line 129 and a fluid line 171. The fluid line 171 receives fluid from peritoneal dialysis solution admixer/cycler 114 and the air-line is used for testing the membrane of the filter. The two air-lines 129 connect to respective ports 191 that automatically connect in an actuator portion 140 as described with reference to FIG. 2B. Sample ports are provided at 168 at the ends of sample fluid lines 132 and 133 for extracting fluid from respective chambers 175 and 176 of a manifold 174. The two chambers 175 and 176 are separated by a barrier 134 and connected by a pumping tube segment 137. Pressure pods 178 are installed in each of the two chambers 175 and 176 to measure pressure on the suction and pressure sides of the pumping tube segment 137. The dialysis solution line 172 has two branches 136 and 139. A waste line 128 and the fluid line 171 connect via a double connector 181. Lines 132, 128, 165, and branch 136 connect to chamber 175. Lines 133, 164, 166, 167, 171 and branch 139 connect to chamber 176.

The double connector 181 supports lines 171 and 128 and provides a pair of connectors 186 and 187 to permit connection of lines 171 and 128 to fill and drain line ports on the peritoneal dialysis solution admixer/cycler 114. The connectors 186 and 187 are sealed by a cap 180. A recess to engage a détente pin provides tactile confirmation of full engagement of the double connector 181. The double connector 181 has a window 183 that provides access to a cut and seal actuator (not shown in this drawing). When the segments 182 and 184 of lines 171 and 128 are cut, the double connector can remain in place sealing the fill and drain line ports on the peritoneal dialysis solution admixer/cycler 114 until it is removed immediately prior to connecting a fresh double connector 181. This provides a barrier to prevent contaminants from entering the connection platform 219 fluid path, which in turn protects the sterile fluid path used by the peritoneal dialysis solution admixer/cycler 114. The connection platform 219 selects the fluid to be delivered to the fluid line 171. Holes 170 are provided in cartridge support 169 that holds the lines in predefined positions. Holes 170 provide access to pinch actuators that selectively close and open the lines 177. Holes 179 provide access to actuators that fracture the frangible seals 154. Note that the cartridge support 169 is bridged to the manifold 174 by a battery of tubes indicated collectively at 300C. Even though the polymer of the tubes is flexible, however, the cartridge support 169 and the manifold 174 may be readily inserted in a receiving slot.

FIGS. 2F and 2G show a concentrate disposable component for use with embodiments of the disclosed subject matter. Referring to FIG. 2F, a concentrate package 260, for example a cardboard box, contains a pair of concentrate containers 262 and 264. Each of the concentrate containers 262 and 264 may be connected to a respective port 265, 266 of a double connector 181B, the double connector 181B may be as the one described above or another, for example, a simple two-port connector 273. Separate connectors may also be used to permit the containers to be replaced independently of each other. In embodiments, the double port may be connected to a receiving device 287 as shown in FIG. 2G so that each concentrate can be installed in the receiving device 287 independently of the other while the double connector remains connected to the 219 the receiving device 287. The receiving device 287 has fluid connectors 285 for connecting to corresponding connectors on the concentrate containers 262 and 264 such that once the containers are installed, fluid can be drawn through the ports 288A and 288B of the two-port connector 273. The latter may be connected to the to the to the connection platform 219, for example as shown in FIG. 2I.

Figure 2H:
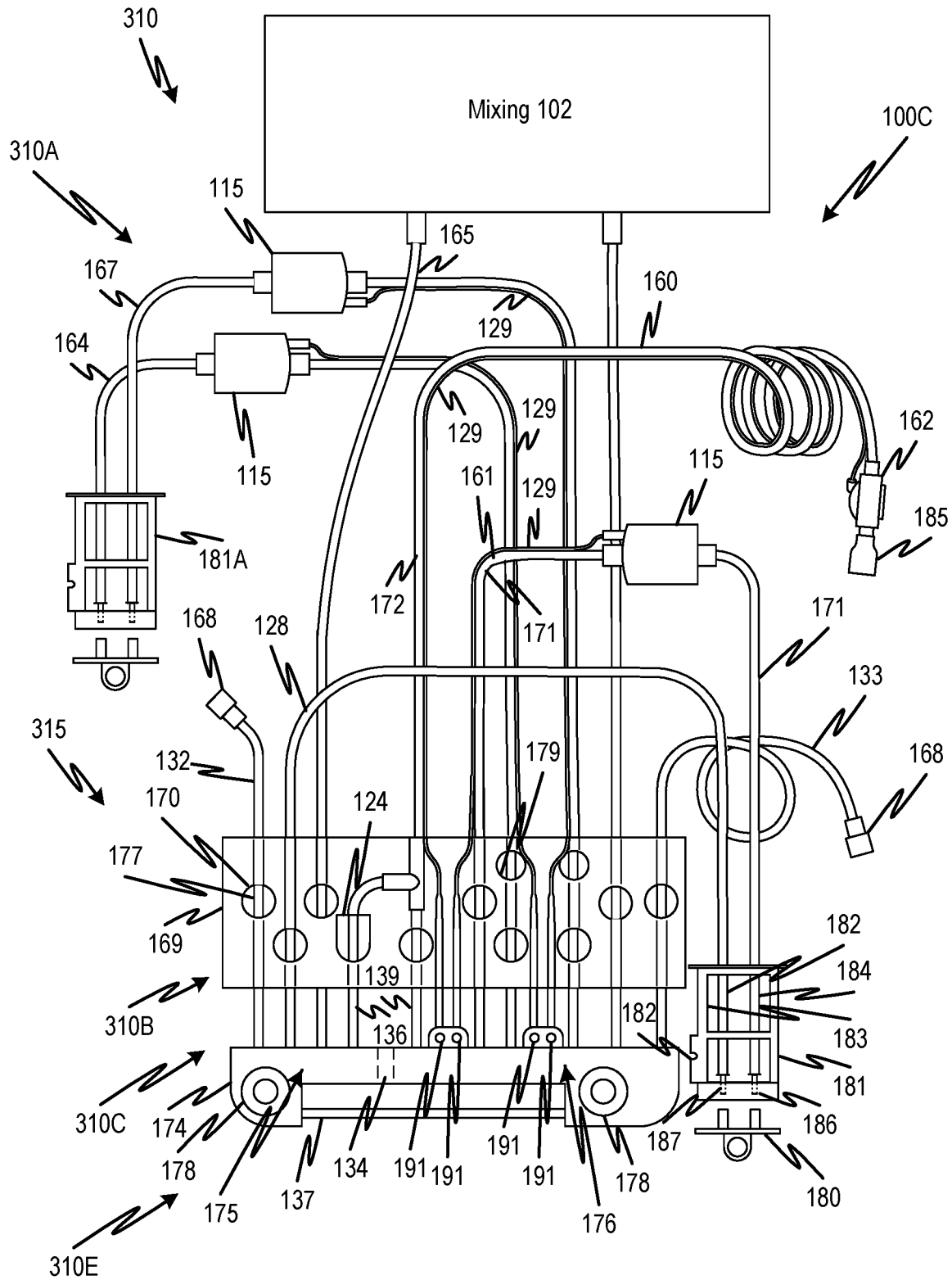
FIG. 2H shows a disposable fluid circuit for a peritoneal dialysis solution admixer/cycler according to embodiments of the disclosed subject matter in which concentrates are extracted from a disposable component that is separate from the cycler/preparation fluid circuit through respective filtered lines.

FIG. 2H shows a disposable fluid circuit for a peritoneal dialysis solution admixer/cycler according to embodiment of the disclosed subject matter in which concentrates are extracted from a disposable component that is separate from the cycler/preparation fluid circuit through respective filtered lines. A disposable fluid circuit 310 has fluid lines and components 310A and a cartridge portion 315 containing a fluid flow director portion 300B and a manifold portion 300E. The disposable fluid circuit 310 is for use with peritoneal dialysis solution admixer/cyclers of certain embodiments disclosed herein. The present disposable is an embodiment that may be used with the peritoneal dialysis solution admixer/cycler 90C where two concentrate containers 105A and 105B are provided as a separate disposable from one 100C with a mixing container 102, only. The mixing container 102 may be provided as a welded double panel sheet with welded seams that define the chambers. The mixing container 102 has two lines, an inflow line 165 and an outflow line 166. The present embodiment is for a peritoneal dialysis solution admixer/cycler and has a pre-connected fill-drain line 160 with a dialysis solution line 172 attached to an air-line 129. The latter may be formed as a single unit by co-extrusion. The air-line 129 attaches to a pressure-sensing pod 162 located at a distal and of the pre-connected fill-drain line 160. A connector 185 at the distal end of the pre-connected fill-drain line 160 is sealed. Another double line 161 has an air-line 129 and a fluid line 171. The fluid line 171 receives fluid from peritoneal dialysis solution admixer/cycler 114 and the air-line is used for testing the membrane of the filter. The two air-lines 129 connect to respective ports 191 that automatically connect in an actuator portion such as 140 as described with reference to FIG. 2B. Sample ports are provided at 168 at the ends of sample fluid lines 132 and 133 for extracting fluid from respective chambers 175 and 176 of a manifold 174. The two chambers 175 and 176 are separated by a barrier 134 and connected by a pumping tube segment 137. Pressure pods 178 are installed in each of the two chambers 175 and 176 to measure pressure on the suction and pressure sides of the pumping tube segment 137. The dialysis solution line 172 has two branches 136 and 139. A waste line 128 and the fluid line 171 connect via a double connector 181. Lines 132, 128, 165, and branch 136 connect to chamber 175. Lines 133, 164, 166, 167, 171 and branch 139 connect to chamber 176. The fluid line 171 connects to a water source.

The double connector 181 supports lines 171 and 128 and provides a pair of connectors 186 and 187 to permit connection of lines 171 and 128 to fill and drain line ports on the peritoneal dialysis solution admixer/cycler 114. The connectors 186 and 187 are sealed by a cap 180. A recess to engage a détente pin provides tactile confirmation of full engagement of the double connector 181. The double connector 181 has a window 183 that provides access to a cut and seal actuator (not shown in this drawing). When the segments 182 and 184 of lines 171 and 128 are cut, the double connector can remain in place sealing the fill and drain line ports on the peritoneal dialysis solution admixer/cycler 114 until it is removed immediately prior to connecting a fresh double connector 181. This provides a barrier to prevent contaminants from entering the connection platform fluid path, which in turn protects the sterile fluid path used by the peritoneal dialysis solution admixer/cycler 114. The connection platform 219 selects the fluid to be delivered to the fluid line 171. Holes 170 are provided in a cartridge support 169 (which may be vacuum-formed) that holds the lines in predefined positions. Holes 170 provide access to pinch actuators that selectively close and open the lines 177. Holes 179 provide access to actuators that fracture the frangible seals 154. Note that the cartridge support 169 is bridged to the manifold 174 by a battery of tubes indicated collectively at 310C. Even though the polymer of the tubes is flexible, however, the cartridge support 169 and the manifold 174 may be readily inserted in a receiving slot. Two concentrates are received through lines 164 and 167, respectively. Each of the lines is filtered by a filter 115 as described with reference to FIG. 1G. Respective holes 170 are provided to control the flow of concentrate through each of the lines 164 and 167. FIGS. 2I and 2J show examples of connection platforms 219 for connecting to a double connector 181A to permit concentrate to be drawn through the lines 164 and 167.

Figure 2I:
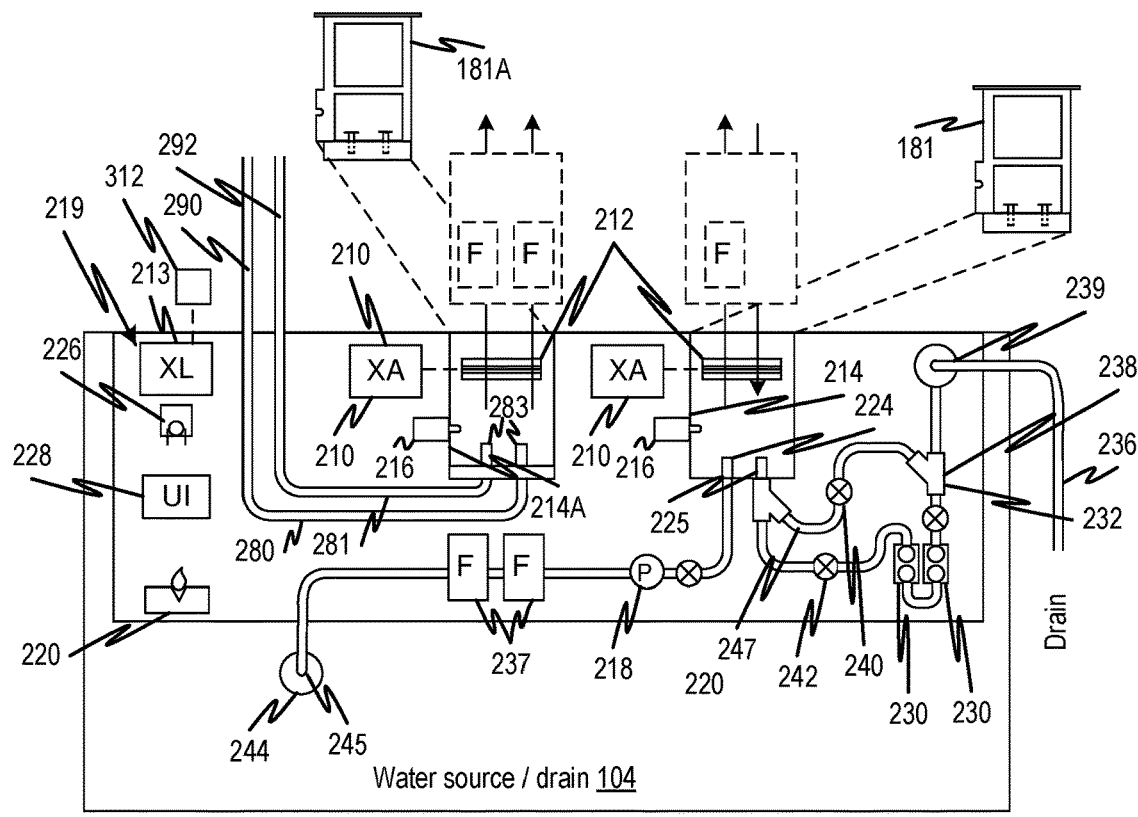
Figure 2J:
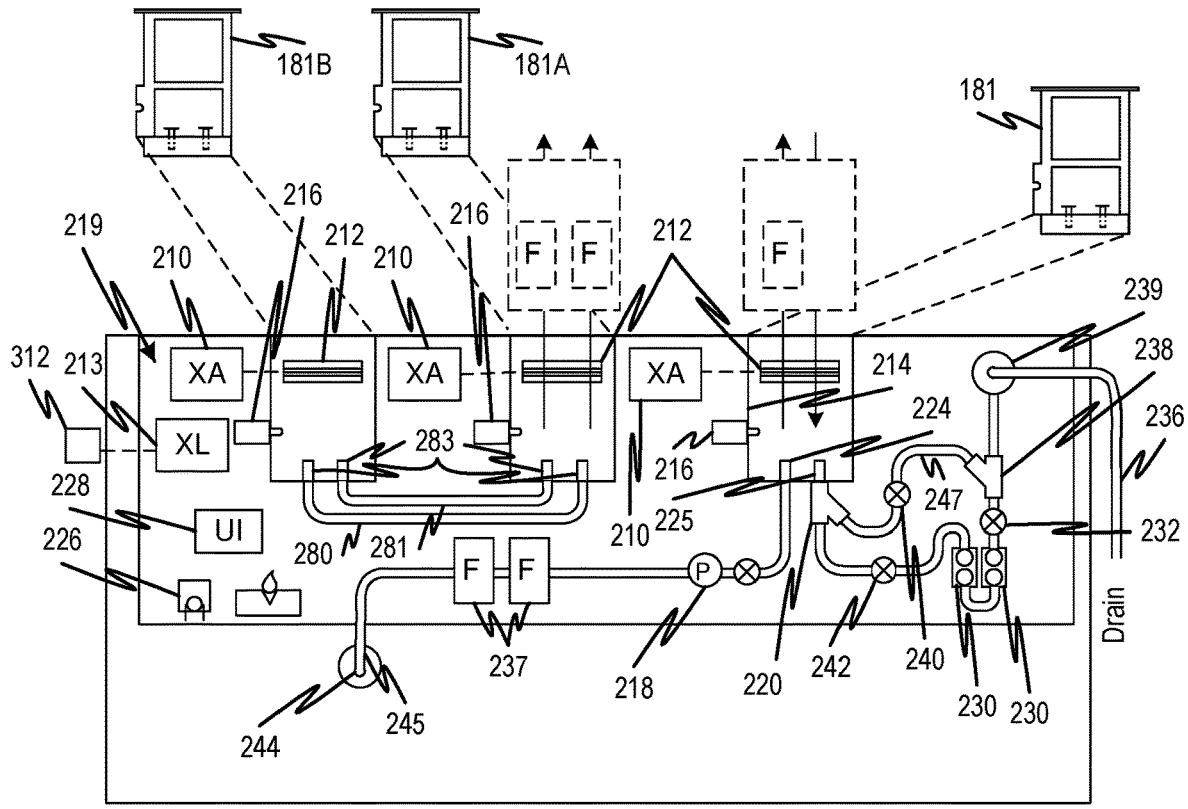

Note that the actuators and sensors of the embodiments of FIGS. 2I, 2J, 2K, 2L, and 2M may be controlled by a single controller, for example, FIGS. 2I, 2J, and 2K show respective embodiments of connection platforms that interface between a pure water source and a separate concentrate source and the peritoneal dialysis solution admixer/cycler embodiments disclosed herein, according to embodiments of the disclosed subject matter. Referring now to FIG. 2I and connection platform 219 is an embodiment of the interface providing the water supply and drain connections (116, 117) between the purified water source 104 and the peritoneal dialysis solution admixer/cycler 114. The connection platform 219 permits the purified water source 104 to be connected to different devices, such as different peritoneal dialysis treatment devices. Shown here is a configuration adapted for peritoneal dialysis medicament preparation, and optionally peritoneal dialysis treatment also. The present configuration differs from that of FIG. 2C in that the present arrangement includes a mechanism for connecting a circuit such as disposable fluid circuit 310 of FIG. 2H which draws concentrate from a double connector 181A which fits in slot 214A to receive concentrate through ports 283. The double connector 181A previously described also has a détente mechanism 216 to provide feedback to the operator when a home (fully connected) position of the double connector 181A is made by inserting into the receiving slot 214A. The receiving slot 214A has a cutting and sealing actuator 212, driven by controller 210, that cuts the tubes through the window of double connector 181, 181A. The ports 283 may be supported on a replaceable double connector 273 as described in FIG. 2F so that these ports are provided by a replaceable connector as part of a concentrate package 260 that includes concentrate containers 262 and 264 or fitted to the receiving device 287 described above with reference to FIG. 2G. In alternative embodiments, the ports 283 may be part of the connection platform 219. In that case, the tubes 290 and 292 may be part of the connection platform 219 and provided with separate connectors for connecting the tubes 293 and 294 of the concentrate containers 262 and 264 (FIG. 2F) or similarly to connect the receiving device 287.

As in the FIG. 2C embodiment, water from the purified water source 104 is received in water line 245 via connection 244 and flows through ultrafilters 237. Pressure of the water suitable for peritoneal dialysis supply is monitored by a pressure sensor 218. A valve 234 selectively controls the flow of water suitable for peritoneal dialysis to a double connector 215. The purified water source terminates at a purified water connector 224 of the double connector 215. The double connector 215 also has a drain terminal connector 225, which splits at a junction 220 into a path that flows to a pair of conductivity sensors 230, and then merges at junction 238 to proceed to a drain 236 and a path that flows directly to the drain 236. The selected path 247 is controlled by valves 232, 240, and 242 which are controlled by a controller 210. The double connector 181 previously described is received in a slot 214 where connections are made to the purified water connector 224 and drain terminal connector 225. A détente mechanism 216 provides tactile and audible feedback to the operator when a home (fully connected) position of the double connector 181 is made by inserting into the receiving slot 214. A connector 239 serves as an adapter to permit connection to various types of drains. The connection platform 219 is also provided with sensors including a moisture sensor 249 located to detect leaking fluid in the connection platform 219, a tilt sensor 226 to indicate the proper orientation of the connection platform 219, and a user interface to interact with the controller 210. The connection platform 219 may be received in a receiving slot 231 and may be formed as a unitary replaceable component. If sterility or leakage problems arise, the connection platform 219 can be replaced easily.

Note that the configuration of FIG. 2I provides a simple and clean connection between the large concentrate containers and the disposable such as 310. However, there is no reason a direct connection could not be provided. That is, the long-term concentrate disposable may be provided with its own connector to connect to a double connector 181A or similar connector or pair of connectors. In another variation, shown in FIG. 2J, the connection platform 219 provides a receiving connector for the concentrate connector 181B, which may be attached to the receiving device 287 of the concentrate containers as shown in FIGS. 2F and 2G. In the connection platform 219 of FIG. 2J, a pair of lines 280 and 281 connect the double connectors 181A and 181B so that concentrate can be drawn by the peritoneal dialysis solution admixer/cycler 114 according to any of the various embodiments. Effectively, the connection platform 219 in this case functions as a pass-through. The connection with double 181B can be made on a low frequency basis according to the size of the concentrate containers and the connection with double connector 181A can be made on a per-peritoneal dialysis treatment (or other schedule) each time the mixing container 102 and associated fluid circuit (e.g. 310) is replaced. FIG. 2K shows another mechanism for connecting and controlling flow of concentrate to the peritoneal dialysis solution admixer/cycler 114. Here connectors 289 connect to a manifold 297 with controllable valves 279 which open and close under the control of a controller 213 to permit only a selected one of the water suitable for peritoneal dialysis from a water line 296, the first concentrate from a first concentrate line 295A, and the second concentrate from a second concentrate line 295B. Each of these may be drawn through common fluid line 298 through connector 224. Thus, the pumping actuator 125 peritoneal dialysis solution admixer/cycler 114 is able to draw each of the fluids. The controller of the peritoneal dialysis solution admixer/cycler 114 can be made to control the valves 279 by communicating with the controller 213 through a user interface 312. The function of the controller 213 and user interface 312 (optional) may be the same except as otherwise indicated across FIGS. 2I, 2J, and 2K. Note that a single controller of the peritoneal dialysis solution admixer/cycler 103 (410, 109) or an independent controller common to both (indicated also by 109) may be employed for controlling the described functions of the peritoneal dialysis solution admixer/cycler 90A through 90D.

FIGS. 2L and 2M show modifications of the connection platform of FIG. 2K to provide for water and concentrate to be supplied through the common fluid line 298. Referring to FIG. 2L, instead of a single manifold as in manifold 297, a pair of junctions 222 are used, one to join the first concentrate line 295A and the second concentrate line 295B. The concentrates are pumped respectively, according to the selection of valves 250A and 250B which are controlled automatically by a controller of the peritoneal dialysis solution admixer/cycler 103 or through a separate controller 109 or through an interface by a dedicated controller 213 of the connection platform 219 (or variations as illustrated in FIGS. 2L and 2M). If the fluid circuit 100B, 100D is used which has a testable type of filter as the filter 115 having an air side and a fluid side separated by a membrane, then the fluid may advantageously be pumped by a pump 221 in a push configuration with respect to the filter 115 rather than relying solely on a suction force provided by the pumping actuator through pumping tube segment 137. A particular concentrate is selected by valves 250A and 250B. A control valve 250C is also operated by the controller to control flow in the water line 296. In any of the embodiments, water may be advantageously pumped by a push pump 246 if water is supplied through a filtration plant 223. For example, water may be filtered through reverse osmosis, deionization, activated carbon, and other types of filters to generate water suitable for peritoneal dialysis from potable water. The pumps 221, and 246 may be controlled as indicated above with respect to the valves 250A and 250B to operate in tandem with the pumping actuators of the peritoneal dialysis solution admixer/cycler (e.g., 103). Thus, in the present variant of the connection platform of FIG. 2K, functions to select one of multiple fluids among water and one or more concentrates thereby allowing all fluids to pass into the fluid circuit through a single inlet line (as in the fluid circuit of FIG. 2E, for example). This allows a single filter to be used for the sterile guarantee. The embodiment of FIG. 2M, another variant of the connection platform 219 of FIG. 2K, may be employed advantageously where a push pump such as push pump 246 is not required to draw water, for example, if instead of using the cycler to prepare dialysis solution, a premixed dialysis solution is connected to one of the inlets instead with suitable programming of the controller to permit flow only from one of the premixed containers at a time. Here control valves 279 select the fluid to be drawn at each time and the pump 221 draws the selected fluid pushing it through the filter. Note that in the embodiment of FIG. 2L, the pressure sensor 218 may be used for feedback control of the push pump 246.

FIG. 3 shows a method of manufacturing a disposable circuit such as disclosed in FIG. 2A. First, the concentrate containers are filled at S10. The concentrate containers are then sealed with frangible elements that form a hermetic seal at S12. This isolates the contents of the concentrate containers from the outside environment and causes them to be protected from intrusion of contaminants. Then at S14, the concentrate containers are connected to a remainder of the fluid circuit, for example the disposable fluid circuit 200. The remaining portions of the fluid circuit are sealed by ensuring that end caps are placed on any line terminations that are not interconnected within the circuit. For example, caps on connector 185, sample ports 168 and connectors 186 and 187. Finally, optionally at S16, the entire circuit assembly with the concentrates, may be radiation sterilized.

Figure 4A:
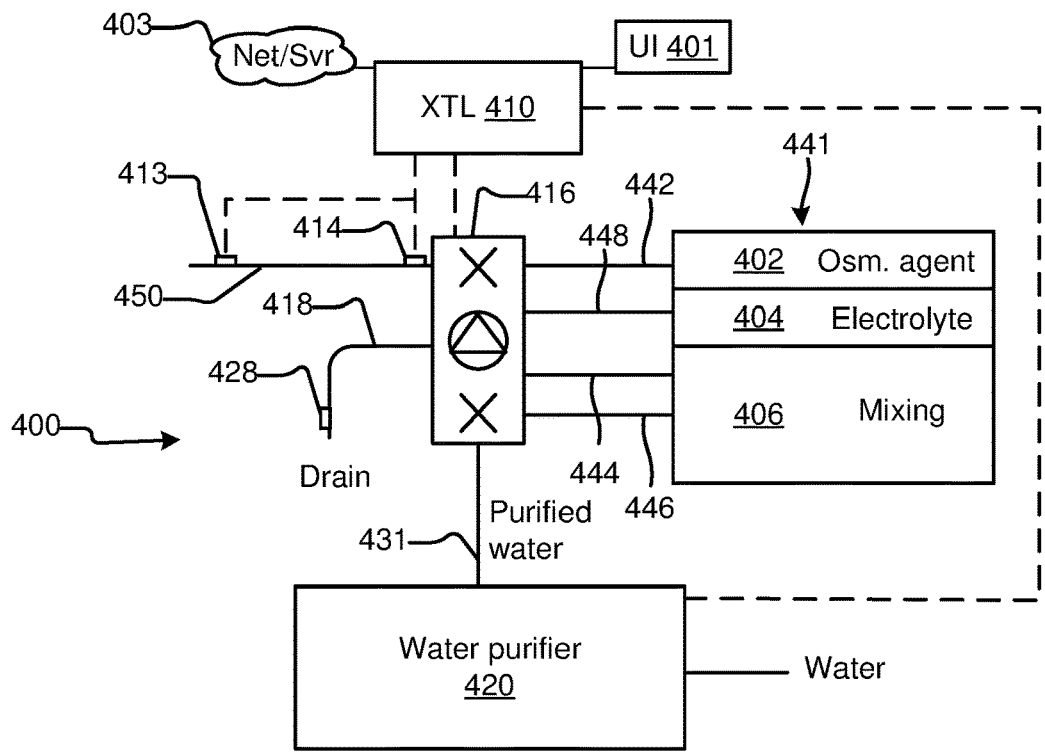
FIG. 4A shows a peritoneal dialysis solution admixer/cycler according to embodiments of the disclosed subject matter.

FIG. 4A shows a peritoneal dialysis solution admixer/cycler according to embodiments of the disclosed subject matter. The present FIGS. 4A through 4K are abstractions of the various embodiments disclosed above for purposes of explaining the operational use thereof for preparing peritoneal dialysis solution and for treating a patient using the structures described above. Referring now to FIG. 4A, a peritoneal dialysis solution admixer/cycler 400 may correspond to any of the foregoing embodiments described for generating dialysis solution by mixing concentrates and water. For example, note embodiments 90A-90D. Here, the peritoneal dialysis solution admixer/cycler 400 generates custom peritoneal dialysis solution according to a prescription stored in a controller 410 (corresponding to controllers described above). The prescription may be entered in the controller via a user interface 401, via a remote terminal and/or server 403, or by other means such as a smart card or bar code reader (not shown). The controller applies control signals to a fluid conveyer and circuit switch 416 and a water purifier 420 and receives signals from distal and proximal pressure sensors 413 and 414, respectively, on a fill/drain line 450 which may be in accord with foregoing embodiments.

The fluid circuit with pump and valve network 416 is a fluid circuit element with one or more sensors, actuators, and/or pumps which is effective to convey fluid between selected lines 442, 444, 446, 448, 450 and 418 responsively to control signals from the controller 410. Example embodiments are described herein, but many details are known from the prior art for making such a device so they are not elaborated here.

A multiple-container unit 441 includes a pre-filled, pre-sterilized osmotic agent concentrate container 402 for osmotic agent concentrate and another electrolyte concentrate container 404 with electrolyte. The multiple-container unit 441 also contains the mixing container 406 (which is empty) which is large enough to hold a sufficient volume of dialysis solution for the completion of at least one fill cycle of an automated peritoneal dialysis treatment. The containers 402, 404, and 406 may be flexible bag-type containers that collapse when fluid is drawn from them and therefore, do not require any means to vent air into them when drained.

Osmotic agent concentrate container 402, electrolyte concentrate container 404, and mixing container 406 are all connected by respective lines 442, 448, 444, and 446 to the fluid circuit with pump and valve network 416. The fill/drain line (or multiple lines) 450 and a drain line 418 for spent fluid (and other fluids) with a conductivity sensor 428 may also be connected to the fluid circuit with pump and valve network 416. The fluid circuit with pump and valve network 416 also has a fill purified water line 431 for receiving water. The water purifier 420 may be a purifier or any source of sterile and pure water including a pre-sterilized container of water or multiple containers. In a preferred configuration, water purifier 420 may be configured as described in WO2007/118235 (PCT/US2007/066251) and US20150005699, which are hereby incorporated by reference in their entireties. For example, the water purifier 420 may include the flow circuit components of FIG. 22A of WO2007/118235 including the water purification stages and conform generally to the mechanical packaging design shown in FIG. 24 of WO2007/118235.

It should be evident that 416 is an abstraction of the peritoneal dialysis solution admixer/cycler 114 as well as elements of a fluid circuit such as fluid circuit 112 and connection platform 219. It should also be evident that 402 and 404 represent concentrate containers according to any of the disclosed embodiments including the concentrate containers 101, 262 and 264, 105A and 105B. The mixing container 406 corresponds to any of the mixing container embodiments (102) described above. Other elements will be evident from their description with the understanding that the figures represent abstractions thereof for purposes of describing the function. It should also be understood that the number and type of concentrates may differ from the present which is disclosed as an example, only. It should also be evident that the examples of concentrates discussed herein are glucose and electrolyte concentrates but they could be one or other multiples or other concentrates in other embodiments. Also, the osmotic agent concentrate or glucose concentrate is presumed here to include an electrolyte concentrate marker to permit the concentration of osmotic agent to be inferred from a measurement of conductivity of diluted agent with a priori knowledge (stored in a memory used by the controller) of the ratio of osmotic agent concentrate to electrolyte concentrate in the osmotic agent concentrate. See US20150005699. In alternative embodiments, the osmotic agent is not provided with electrolyte and the peritoneal dialysis solution admixer/cycler 400 relies on volumetric proportioning for the transfer of osmotic agent. Note also that the order of concentrate addition may be reversed, with electrolyte being added first.

Figure 4B:
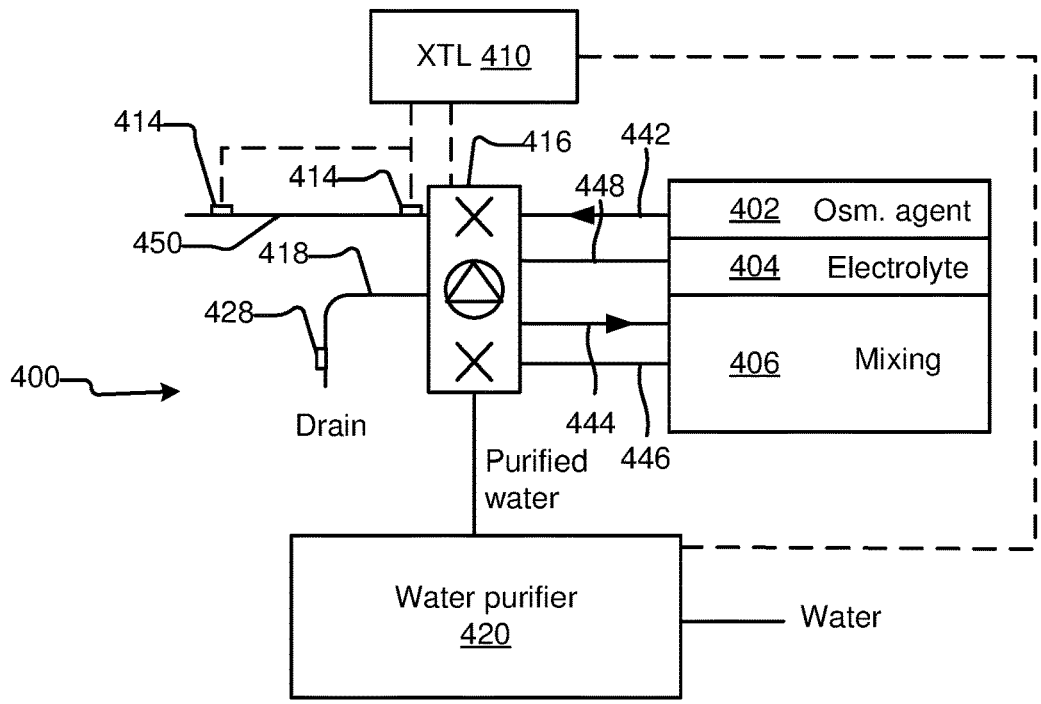
FIG. 4B shows the peritoneal dialysis solution admixer/cycler of FIG. 4A in a first phase of fluid preparation in which osmotic agent concentrate is added to a mixing container, according to embodiments of the disclosed subject matter.

FIG. 4B shows a preliminary stage of fluid preparation prior to peritoneal dialysis treatment according to an embodiment of the disclosed subject matter. The controller 410 reads a prescription and generates a command, responsive to a peritoneal dialysis treatment preparation initiation command, to flow osmotic agent concentrate from osmotic agent concentrate container 402 to the mixing container 406. The command is applied to the fluid circuit with pump and valve network 416 to connect the osmotic agent concentrate line 442 to the batch fill line 444 and also to convey the osmotic agent concentrate into the mixing container 406. This may be done by one or more valve actuators and one or more pumps that form the fluid circuit with pump and valve network 416. The fluid circuit with pump and valve network 416 may be configured to meter the quantity of osmotic agent concentrate precisely according to a predicted amount of dilution by electrolyte concentrate and water to achieve the prescription. The metering may be performed by a positive displacement pump internal to the fluid circuit with pump and valve network 416 or other means such as a measurement of the weight of the osmotic agent concentrate container 402 or the mixing container or a volumetric flow measurement device.

In an alternative embodiment, part of the water (less than the total used for dilution as discussed below with reference to FIG. 4C) is added to the mixing container first, before the osmotic agent concentrate and electrolyte concentrates (if needed) are pumped into the mixing container.

Figure 4C:
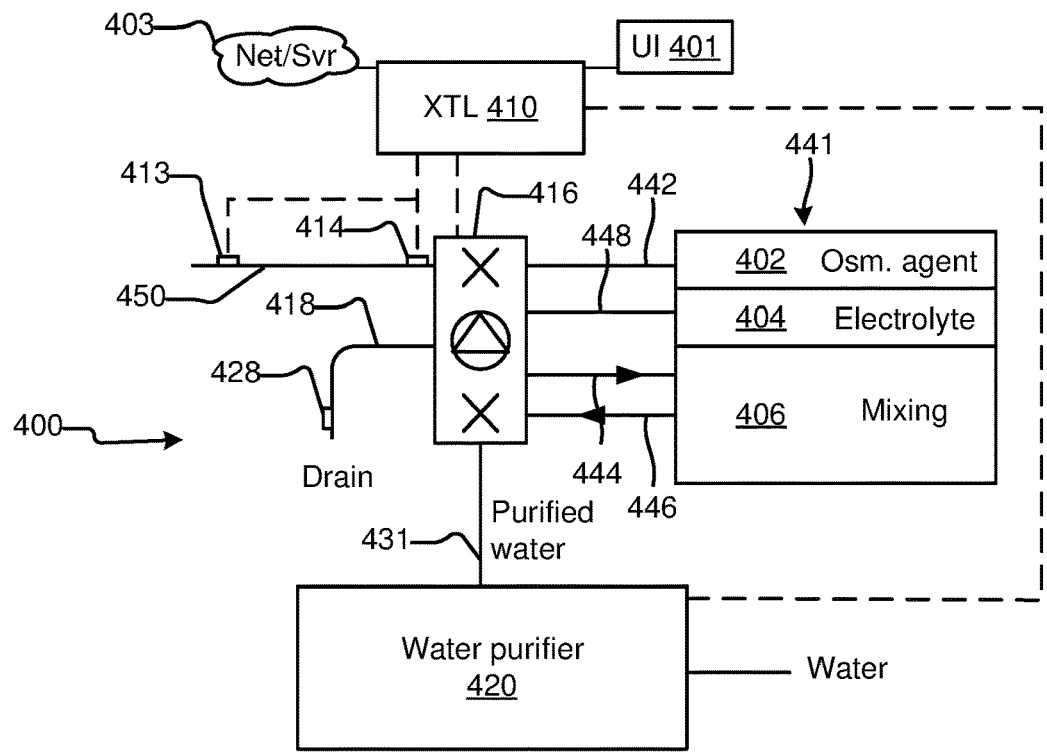
FIG. 4C shows the peritoneal dialysis solution admixer/cycler of FIG. 4A in a second phase of fluid preparation in which a dialysis solution precursor is obtained by diluting and mixing the contents of the mixing container, according to embodiments of the disclosed subject matter.

Referring now to FIG. 4C, a dilution stage is performed using the peritoneal dialysis solution admixer/cycler 400. The controller 410, in response to the prescription, generates a command, to flow purified water from the water purifier 420 to the mixing container 406. The command is applied to the fluid circuit with pump and valve network 416 to connect the purified water line 431 to the mixing container 406 to add a measured quantity of water to dilute the osmotic agent concentrate in the mixing container 406. The controller may control the fluid circuit with pump and valve network 416 to ensure the correct amount of water is conveyed. Alternatively, the water purifier may incorporate a flow measurement device or metering pump or other suitable mechanism to convey the correct amount of water. The controller 410 may be connected to the water purifier 420 to effectuate the dilution result. The fluid circuit with pump and valve network 416 may also be configured to circulate diluted osmotic agent concentrate solution through lines 444 and 446 either simultaneously with the dilution or after the diluting water has been transferred to the mixing container according to alternative embodiments.

The relative amounts of water, osmotic agent concentrate, and electrolyte concentrate may be defined based on the ratiometric proportioning properties of the pump. Since a single pump tube is used to convey all the liquids into the mixing container, most sources of offset from predicted pumping rate (based on shaft rotations, for example) to actual pumping rate affect all the fluids roughly equally.

Figure 4D:
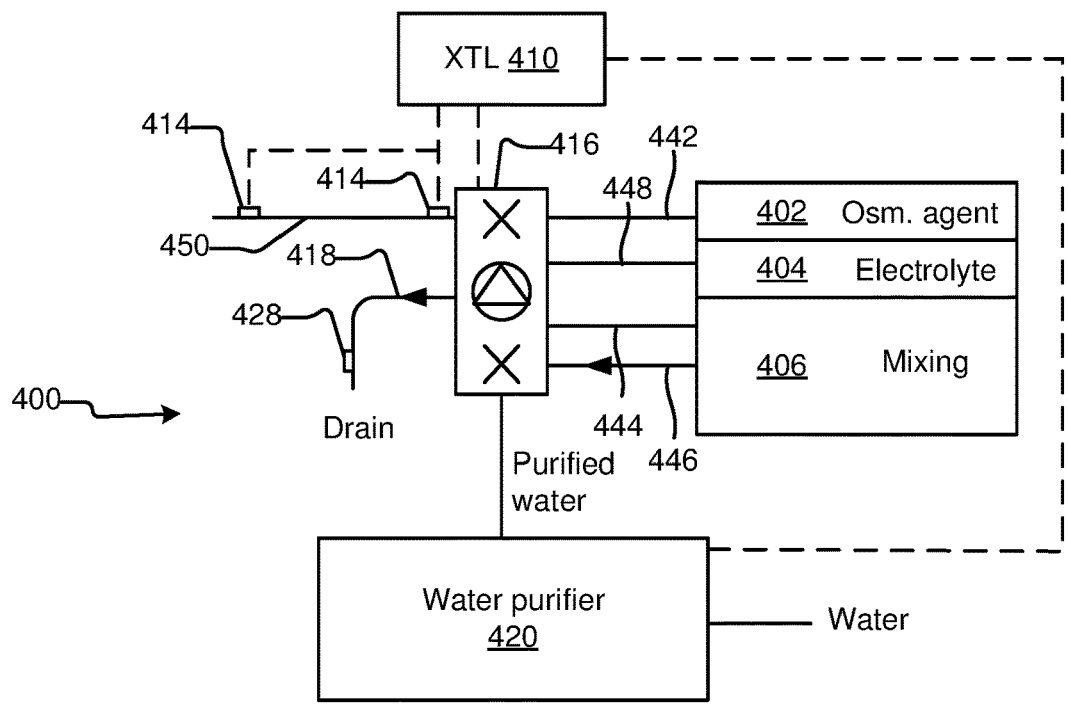
FIG. 4D shows the peritoneal dialysis solution admixer/cycler of FIG. 4A in a third phase of fluid preparation in which the peritoneal dialysis solution precursor properties are verified, according to embodiments of the disclosed subject matter.

Referring now to FIG. 4D, the diluted osmotic agent concentrate solution in the mixing container 406 is tested to ensure that the correct concentration of osmotic agent is achieved. In an embodiment, the osmotic agent concentrate 402 has an amount of electrolyte concentrate to generate a conductivity signal using the conductivity sensor 428 when fluid from the mixing container 406 is conveyed by the fluid circuit with pump and valve network 416 to the drain line 418 past the conductivity sensor. The amount of electrolyte concentrate pre-mixed with the osmotic agent concentrate may be the lowest ratio of electrolyte concentrate to osmotic agent concentrate that a possible prescription may require. The fluid circuit with pump and valve network 416 may perform the function using one or more valve actuators and one or more pumps that form the fluid circuit with pump and valve network 416. The fluid circuit with pump and valve network 416 may be configured to meter the quantity of water precisely or the function may be provided by the water purifier 420. The controller may add additional water or osmotic agent concentrate and test the conductivity again if the measured concentration of osmotic agent and/or electrolytes, if applicable, is incorrect. In addition to using a combined osmotic agent and electrolyte concentrate in osmotic agent concentrate container 402, in an alternative embodiment, the osmotic agent concentrate container 402 holds osmotic agent concentrate with no electrolyte concentrate and osmotic agent concentration is optionally measured directly by other means such as specific gravity (hydrometer), refractive index (refractometer), polarization, infrared absorption or other spectrographic technique.

Figure 4E:
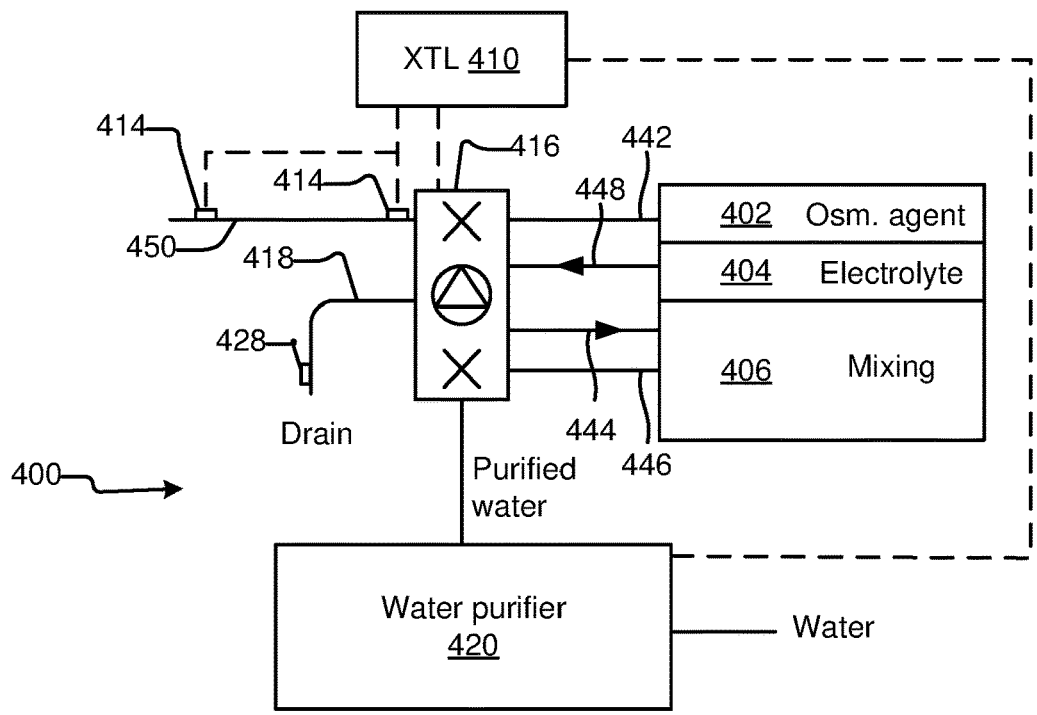
FIG. 4E shows the peritoneal dialysis solution admixer/cycler of FIG. 4A in a fourth phase of fluid preparation in which dialysis solution precursor is further prepared by addition of electrolyte concentrate to the mixing container, according to embodiments of the disclosed subject matter.

FIG. 4E shows an electrolyte concentrate addition stage of fluid preparation prior to peritoneal dialysis treatment according to an embodiment of the disclosed subject matter. The controller 410 reads a prescription and generates a command to flow electrolyte concentrate from container 404 to the mixing container 406. The command is applied to the fluid circuit with pump and valve network 416 to connect the electrolyte concentrate line 448 to the batch fill line 444 and also to convey the electrolyte concentrate into the mixing container 406. This may be done by one or more valve actuators and one or more pumps that form the fluid circuit with pump and valve network 416. The fluid circuit with pump and valve network 416 may be configured to meter the quantity of electrolyte concentrate precisely according to a predicted amount of dilution by osmotic agent concentrate and water that has been previously determined to be in the mixing container 406, to achieve the prescription. The metering may be performed by a positive displacement pump internal to the fluid circuit with pump and valve network 416 or other means such as a measurement of the weight of the electrolyte concentrate container 404 or the mixing container 406 or a volumetric flow measurement device.

Figure 4F:
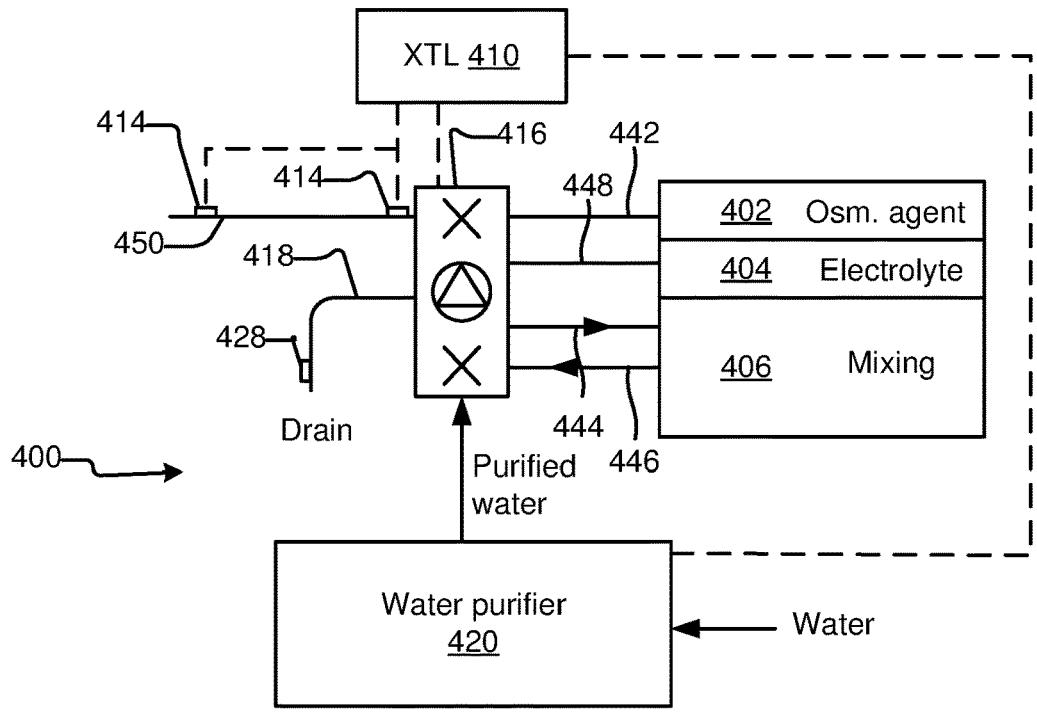
FIG. 4F shows the peritoneal dialysis solution admixer/cycler of FIG. 4A in a fifth phase of fluid preparation in which end-use dialysis solution is prepared by adjustment of the dilution of the mixing container contents, according to embodiments of the disclosed subject matter.
Figure 4G:
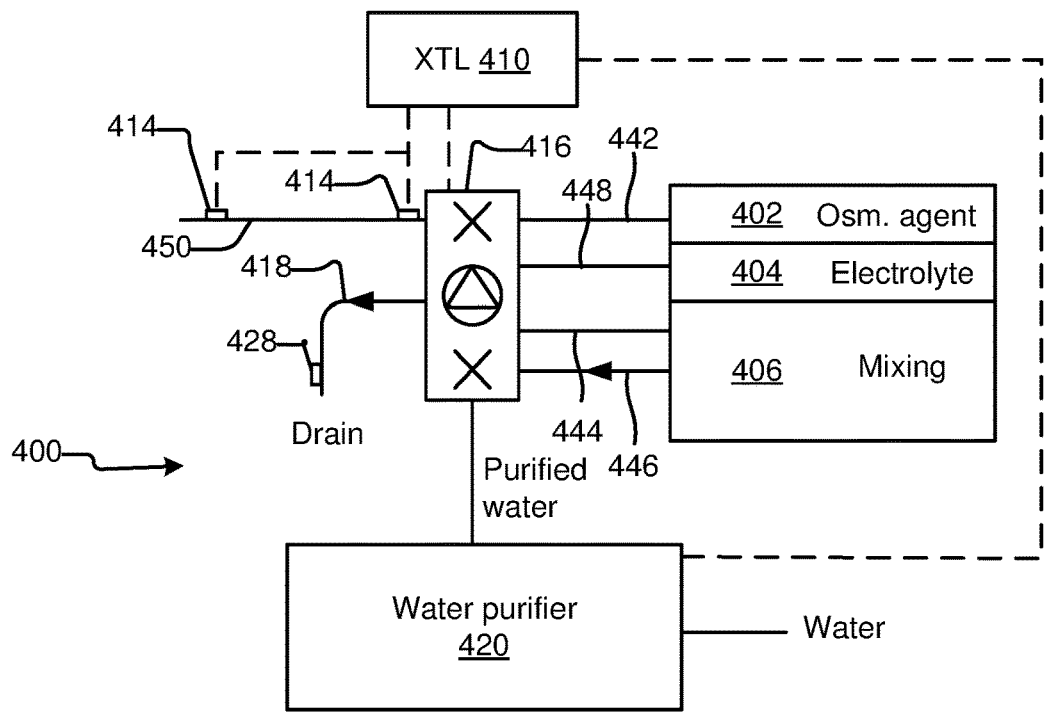
FIG. 4G shows the peritoneal dialysis solution admixer/cycler of FIG. 4A in a sixth phase of fluid preparation in which dialysis solution in the mixing container is verified, according to embodiments of the disclosed subject matter.

Referring now to FIG. 4F, the electrolyte concentrate may be mixed using the batch fill and drain lines 446 and 444 in a closed loop. If necessary, depending on how much dilution was performed during the osmotic agent concentrate dilution process, further dilution may be performed as described above. The final formulation may be achieved by the process illustrated in FIG. 4F. Then, as illustrated in FIG. 4G, the final electrolyte concentration of the mixture in mixing container 406 may be determined with a conductivity sensor 428 by flowing a sample therethrough.

Although gravimetric and tracer/conductance sensing were described as devices for ensuring proper proportioning and dilution rates for achieving target prescriptions, it should be clear that any embodiments of a peritoneal dialysis solution admixer/cycler disclosed herein may employ ratiometric proportioning as well, particularly where positive displacement pumping is employed. Ratiometric proportioning takes advantage of the volumetric repeatability and predictability of certain pumps. For example, a particular pump can deliver a highly repeatable volume of fluid for a given number of pumping cycles (pump rotations for a peristaltic pump or cycles for a diaphragm pump, for example). If all dialysis solution components (water, osmotic agent concentrate, and electrolyte concentrate, for example) are delivered to the mixing container using the same pump, including, for example, the pumping tube segment of a peristaltic pump, then the volume ratios of the components will, after adjustment for potential flow path and/or viscosity differences as described below, be fully determined by the number of pump cycles used to convey each component.

Rationmetric proportioning may supplement or substitute for measurement of the fluid conductance or density or other measurements. To convert the number of pump cycles to actual displaced mass or volume, a calibration may be performed and/or flow path (including fluid properties) compensation parameters may be employed. The flow path compensation parameters may be respective to each particular fluid flow path and/or fluid type, or may be identical for all fluid paths and fluid types. To provide enhanced accuracy, one or more pump calibration and/or flow path compensation parameters may be generated through a calibration procedure. Typically, flow path compensation factors will be established and stored in non-volatile memory. Typically, one or more flow path calibration procedures will be performed when the peritoneal dialysis solution admixer/cycler is used by a patient. The calibration procedure may be performed after each new fluid set is installed, or before each batch preparation cycle, or even multiple times during the preparation of a single batch. A disposable fluid set may be installed every day. The calibration procedure may be done using water. The calibration may sequentially pump fluid through one or more of the stages provided in Table 1.

TABLE 1

Example stages for sequentially pumping fluid during calibration

| From | To |
| --- | --- |
| Water source | Drain |
| Mixing container | Drain |
| Osmotic agent concentrate container | Drain |
| Electrolyte concentrate container | Drain |
| Patient access | Drain |
| Osmotic agent concentrate container | Mixing container |
| Electrolyte concentrate container | Mixing container |
| Water source | Mixing container |

In the calibration procedure, fluid is pumped between any or all of the paths identified above. A separate calibration coefficient may be generated for each of the paths. The calibration coefficient may be stored in a memory or non-volatile data store, for example, as a parameter representing the number of ml/per pump rotation (or diaphragm pump cycle), or as a proportionality ratio relative to a particular reference flow path. The actual fluid quantity transported during the calibration step may be measured by any suitable device (flow sensor) including volume or mass measurement devices or direct flow rate measurement with integration, for example, using laser Doppler velocimetry, thermal transit time, magnetohydrodynamics, propeller hydrometer, positive displacement flow measurement, differential pressure through a resistance such as a venturi, nozzle, orifice plate, or other flow obstruction, variable area or rotameter, pitot or impact tube, vortex shedding frequency counting, ultrasonic, or other device. A particularly advantageous device for flow calibration is to measure the transit time of a fluid property perturbation between spaced fluid property sensors as described below with reference to FIG. 22A. Any of the disclosed embodiments may employ a flow sensor in which at least the portion of which that carries fluid is disposable so that the flow rate (or total displaced fluid quantity) can be input to a controller while allowing the use of a disposable fluid circuit. Examples include an ultrasonic soft tube flowmeter made by Strain Measurement Devices SMD that non-invasively measure flow in soft tubing by means of slotted transducers in which a length of tubing can be inserted during fluid circuit installation. For cartridge embodiments, the PD cycler can employ a moving transducer stage that engages an exposed tube length of the cartridge after passive insertion of the cartridge.

The pumping system may also be sufficiently repeatable in a way that allows precise ratios to be established without calibration, depending on the predefined tolerances. If the manufacturing tolerances, including materials, are sufficiently controlled, a desired level of control over ratios may be achieved without in situ (point of care) calibration. A particularly sensitive component in terms of guaranteeing repeatability is the pumping tube segment of a peristaltic pump. In a first embodiment, the peristaltic pump tube segment is made from a material whose mechanical and material tolerances are controlled within predefined limits. The lengths of the tubing circuit elements and mechanical parameters are also controlled within respective predefined limits. A calibration may then be done outside the peritoneal dialysis treatment context, e.g., in the laboratory, to calculate precise values to convert pump cycles to fluid quantity transferred for a single lot of replaceable fluid circuits. The calibration may be done for multiple lots. The calibration may also be done for each fluid circuit. The calibration may also be done by the peritoneal dialysis solution admixer/cycler for each fluid circuit. The calibration may also be done for each batch of peritoneal dialysis fluid prepared by the fluid circuit.

Figure 4H:
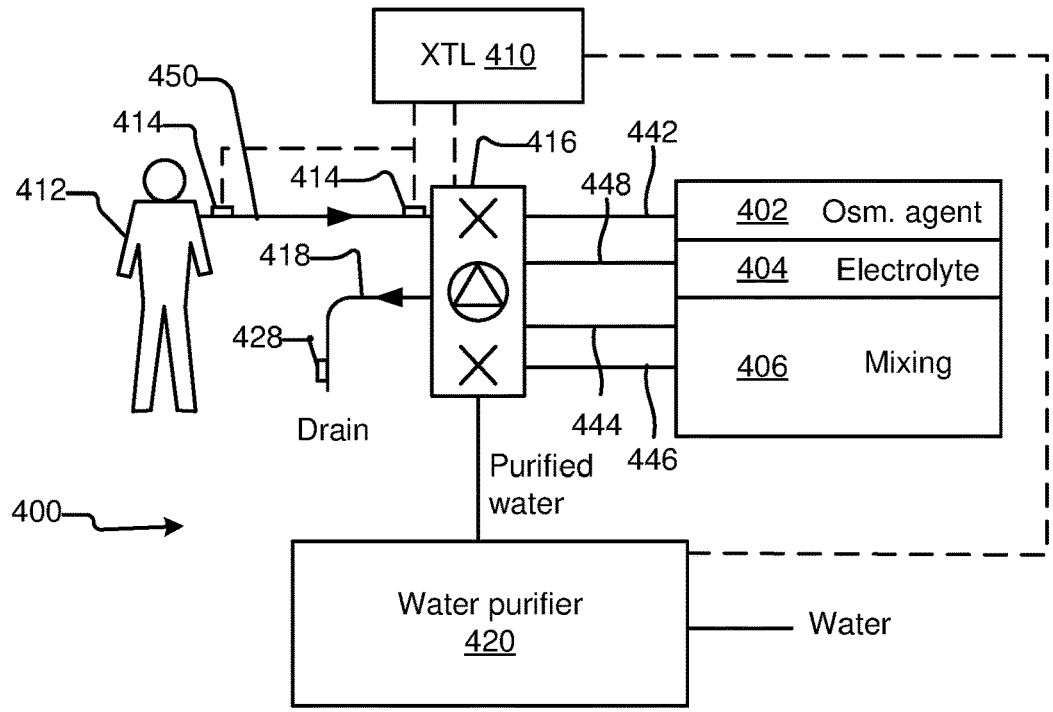
FIG. 4H and FIG. 4K show the peritoneal dialysis solution admixer/cycler of FIG. 4A in various peritoneal dialysis treatment modes, according to embodiments of the disclosed subject matter.
Figure 4K:
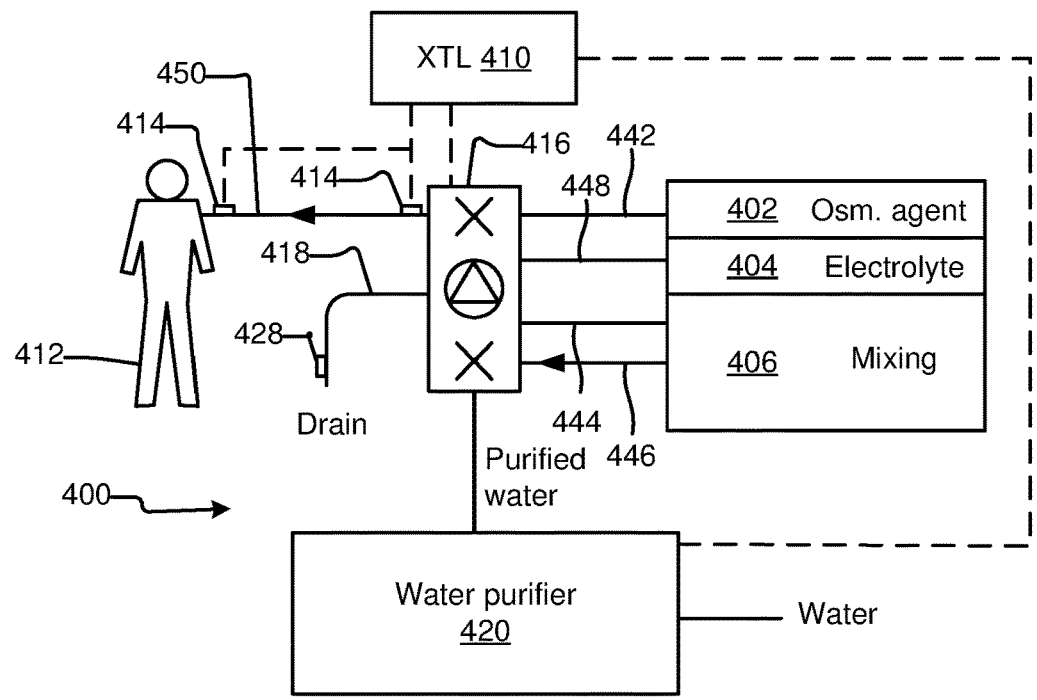

Referring to FIG. 4H, subsequent to the preparation of the contents of the mixing container 406 as described above, the fluid circuit with pump and valve network 416 may be configured to drain the patient 412 depending on the patient's prior status. Spent dialysis solution fluid may be withdrawn by the fluid circuit with pump and valve network 416 and conveyed through the drain line 418. Then, the contents of the mixing container 406 may be conveyed as illustrated in FIG. 4K to the patient. Here the controller 410 has configured the fluid circuit with pump and valve network 416 to flow fluid to a patient 412.

Double Connectors

Figures 5A, 5B:
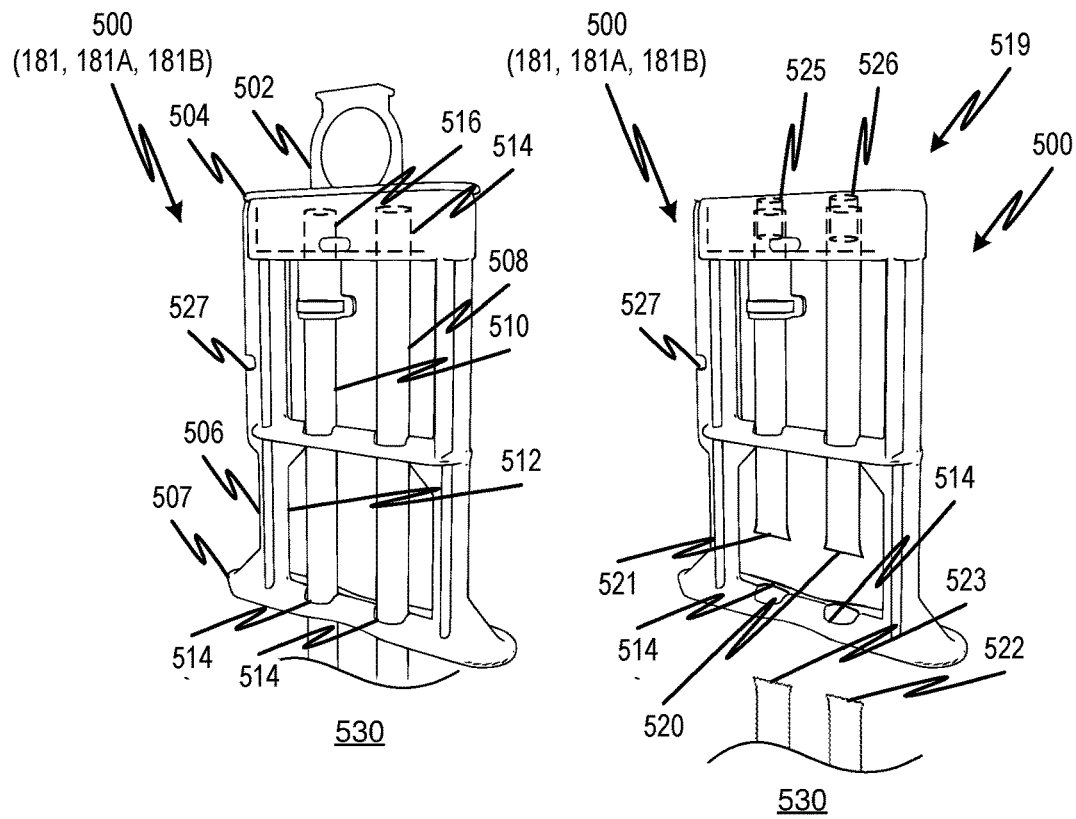
FIGS. 5A-5D illustrate the structure and use of a multi-function connector according to embodiments of the disclosed subject matter.

Referring now to FIG. 5A, the double connector of 181, 181A, 181B is shown as a detailed embodiment of the connector 500. A single monolithic member has a shape with at least one window, where two windows are shown one of which is indicated as window 512. The body 504 has a ridge 507 that overhangs the frame 506 to permit the frame 506 overall to be grasped easily by a user for pushing or pulling to connect ports 514, 516 to ports of a device (e.g., 219) to which lines 508 and 510 of a fluid circuit 530 are to be connected. A releasable port cover 502 (see also cap 180) seals ports 525 and 526 to prevent contamination thereof. The window 512 provides access to cut and seal elements that seal and cut the lines 508, 510 when the double connector 500 is to be replaced. FIG. 5B shows the double connector 500 after cutting and sealing, the sealed ends of one end of cut tubes forming stubs indicated at 520 and 521 and the opposing ends at 522, 523. The ends 522, 523 remain attached to a fluid circuit 530 which is to be replaced. The stubs 520, 521 remain attached to a resulting stub connector 519 which can remain attached to a connected device after use so as to act as a cover and seal against environmental contamination of a connected device, such as connection platform 219 connectors 224 and 225. Here, the protected ports of the connected device are indicated at 525 and 526. Although two channels are shown, it should be evident that the configuration may be modified to provide connections for any number of channels including one or more than two.

Figure 5C:
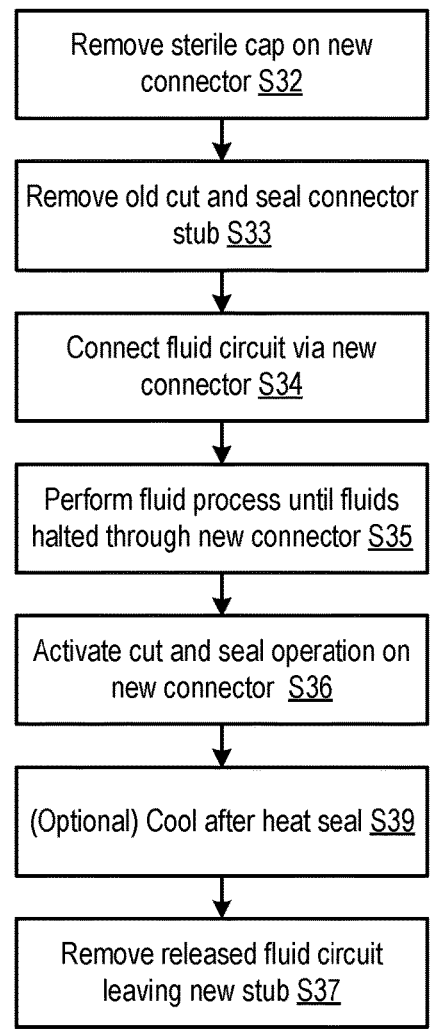
Figure 5D:
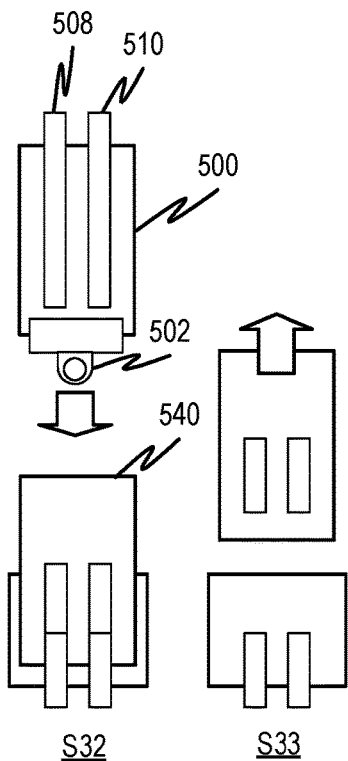
Figure 5D:
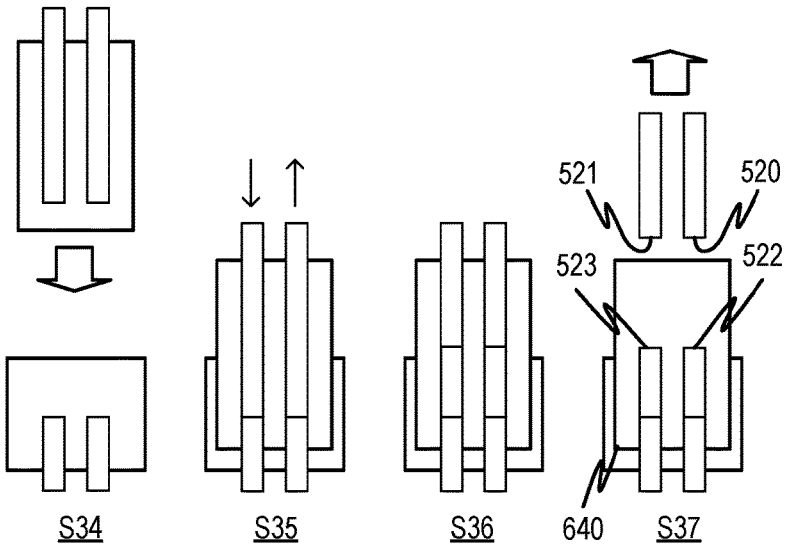

Referring to FIGS. 5C and 5D, the use of a connector 500 (which may be a double connector) including a cut and seal operation in which a portion 540 of a connector (e.g., double connector 181) is left in place to act as a sterile barrier begins with the removal of a sterile barrier-type cap from the end of the connector S32. For example, the sterile barrier may take the form of the double releasable port cover 502. Next, as S33, sterile barrier formed by a previous connector (which was cut and sealed See FIGS. 6A-7D and elsewhere in the present disclosure) is removed and a new replacement connector of the same form as the connector 500 attached S34. Then the circuit connected by means of the new connector is used until it is expired S35. A cut and seal operation is initiated at S36 resulting the separation of the fluid circuit (cut and sealed forming the stubs 520, 521 and ends 522, 523) and a new portion 540 of the new connector to be left in place to act as a sterile barrier. The cut and seal operation may include cooling the cut ends of the tube to speed the operation so that a delay for sufficient passive cooling is not required. The latter may also permit the cutting heads to act as mechanism for gripping the stubs 520 and 521 to prevent them being removed before cooling. See, for example, the embodiment of FIGS. 6E and 6F which have a broad flat interface for gripping the ends of the cut tube 666.

Figure 5E:
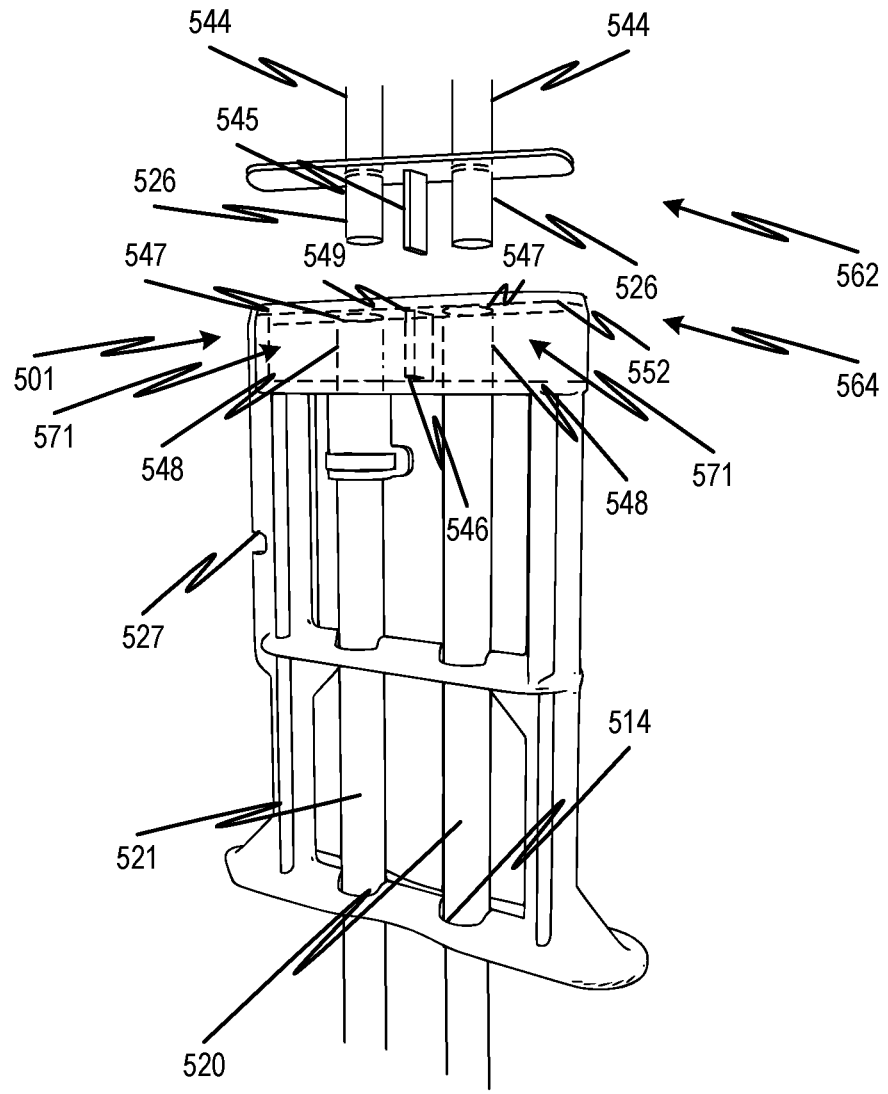
FIG. 5E shows features for a variation of a double connector 500 that protect against contamination.

FIG. 5E shows features for a variation of a double connector 501 that protect against contamination. A male connector portion 562 mates with a female connector portion 564. Ports 526 (male) pass through openings 547 of female ports 548. A pin 545 is provided on the male connector portion 562 that is received within a recess 546. The female ports 548 open in a wall 552 as does an access 549 of the recess 546. Lines 544 connect to the male connector portion 562. The remainder of the double connector 501 is as described with reference to connector 500 shown in FIGS. 5C and 5D. The pin 545 may be sized to prevent the ports 526 from contacting a flat surface inadvertently and thereby prevent contact contamination. The pin 545 may also be shaped asymmetrically to prevent incorrect orientation of the connectors. In variations, the double connector 501 may be modified such that it has a greater or lesser number of tubes 508, 510 and openings 547. Also, the number of pins 545 and recesses 546 may differ from what is shown. For example two pins and recesses may be provided at the edges 571 with or without the illustrated pin and recess. Note that in variations of the embodiments, the male and female connectors may be swapped or mixed on a given side of the male connector portion 562 and the female connector portion 564. One or more pins 545 may be provided on either side or mixed as may openings 547.

FIG. 6A shows mechanical aspects and a control and sensor system for the cut-and-seal devices with actuation, temperature, and force control features, according to embodiments of the disclosed subject matter. FIGS. 6B through 6D show a sealing and cutting operation provided by the embodiment of FIG. 6A. A pair of jaws 11 and 18 close on opposite sides of a tube 50 to cut and seal the tube 50 such that the tube 50 is divided into two parts with ends 54A and 54B sealed. The jaw 11 receives heating or cooling through a conveyance 20A or multiple conveyances 20B which may be electrical conductors for resistive heating element 14 or a combination of heating and cooling heat transfer fluids such as molten salt and refrigerant. The source of heat/cool or current supply is provided by a source 6. Either jaw 11 or 18 may be heated to achieve the described effect in alternative embodiments. A drive 2 under control of a controller 4 moves at least one of the jaws 11 and 18 toward the other or together. Temperature sensors 16 and 12 may be provided to regulate the temperature and provide feedback control for a cutting and sealing operation. The controller 4 may receive the temperature signals and control the drive 2. A force sensor 40 may indicate to the controller the magnitude of force applied through the tube 50 for feedback control of a cutting operation or for error detection (out of bounds force). The cutting heads can have various shapes as shown in FIGS. 7A-7D. FIG. 7A illustrates opposing jaw shapes with jaw 604 having a flattened tip 606 and jaw 602 having a flat surface 608. FIG. 7B illustrates opposing jaw shapes with jaw 614 having a sharp tip 616 and jaw 612 having a flat surface 618. FIG. 7C illustrates opposing jaw shapes with jaw 624 having a rounded tip 626 and jaw 622 having a flat surface 628. In FIG. 7D, a sharp ridge 636 is provided on jaw 634 and a recess 637 on jaw 635. An alternative jaw 632 that may be used with the jaw 634 has a flat surface 638.

FIGS. 6E and 6F show a cut and seal arrangement in which the cutting and sealing portions move partially independently. A cutting knife 662 cuts a tube 666 when a jaw 658 pushes up against it. The jaw 658 or the jaw 654 (or both) may be heated to melt the tube 666 such that tube is cut and sealed in a single operation. A spring 664 ensures that a predefined amount of force is maintained for heating the tube 666 during the closing of the jaws. FIG. 6G shows a configuration in which the jaws are rounded elements 670 and 672 which may cut and seal the tube 666 where either or both jaws may be heated. Cooling in the above embodiments may be provided to cool the jaws and the tubing cut ends for safety or speed of completion. The arrangements of FIGS. 6A through 6F are details that may apply to the cutting and sealing actuator 212.

Figure 8A:
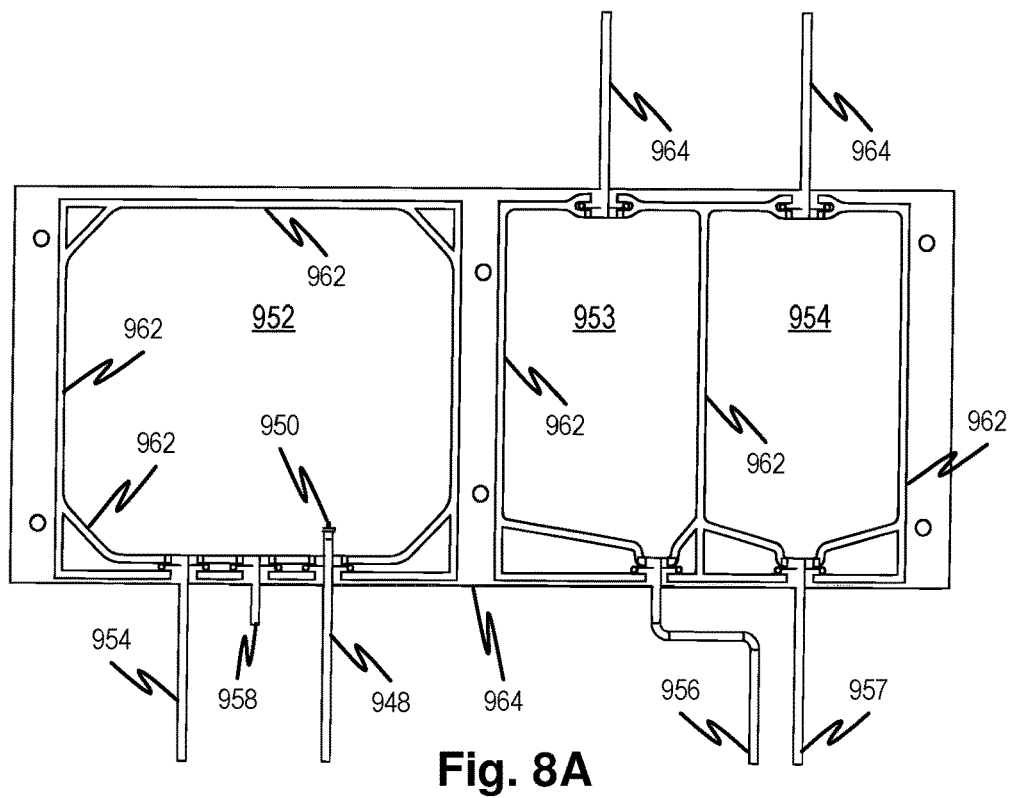
FIGS. 8A and 8B show details of chamber portions of fluid circuits according to embodiments of the disclosed subject matter.
Figure 8B:
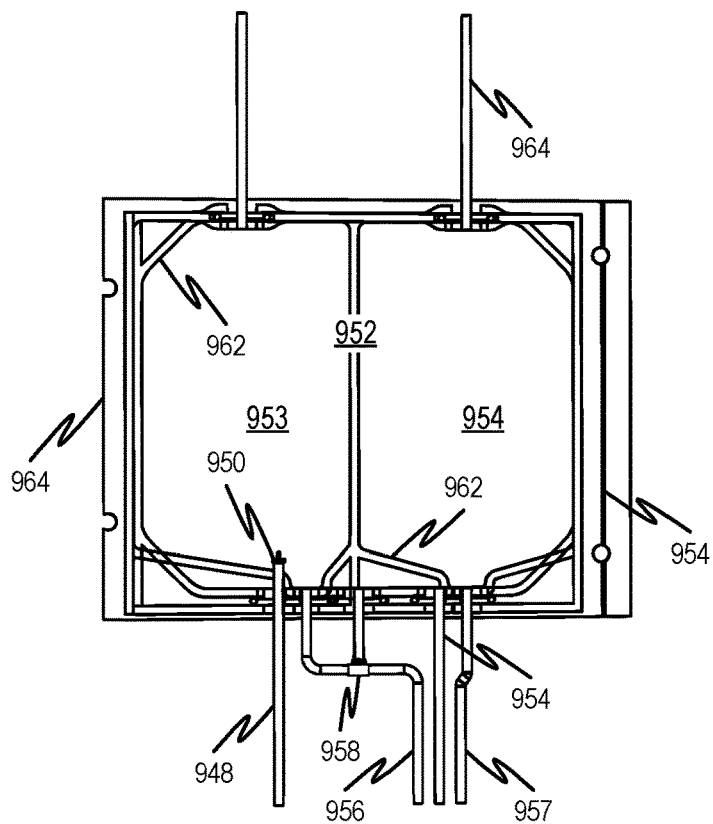

Referring to FIGS. 8A and 8B, a multiple chamber portion 200D of disposable fluid circuit 200 is shown in greater detail. Features of the present embodiment may be applied to other fluid circuit portions as well including the single mixing container 300C (FIG. 2E). Concentrate containers 953 and 954 and mixing container 952 are formed from a single pair of sheets by welding seals 962, shown as a pair of lines all around the depicted structure. Concentrate fill tubes 964, concentrate outlet tubes 956 and 957, mixing container inlet 948 and outlet line 954, as well as a mixing container sample tube 958 are all welded as the seals 962 are closed by solvent bonding, thermal welding, polymer fill-bonding, ultrasonic welding, or other means. The entire structure may then be folded as shown in FIG. 8B to form a compact structure before or after a predefined quantity of concentrate is conveyed through the concentrate fill tubes 964 and the latter sealed.

A nozzle 950 may terminate the mixing container inlet 948 tube which extends into the chamber. This causes the extended part of the tube to whip around to inject incoming fluid around the mixing container 952 to agitate the contents and promote effective mixing of the contents. The mixing container sample tube 958 may be terminated by a septum to permit the insertion of a hypodermic needle. The length of the extended part may be at least 3 diameters into the container. The length may be five, 7.5, 10, or 15 diameters. The length may be between 3 diameters and 25 diameters. The length may be at least 5 diameters. Here, the term diameter refers to the tube outer diameter. Note that another alternative is for the inlet line to have a nozzle but no extended part, that is, the nozzle may be located at the wall of the mixing container and be aimed toward the center of the mixing container.

Figure 8C:
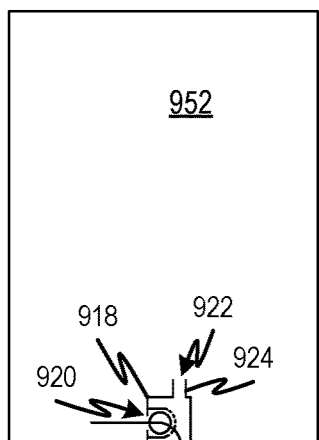
FIGS. 8C through 8G show various features to promote mixing of fluids in a mixing container according to embodiments of the disclosed subject matter.
Figure 8D:
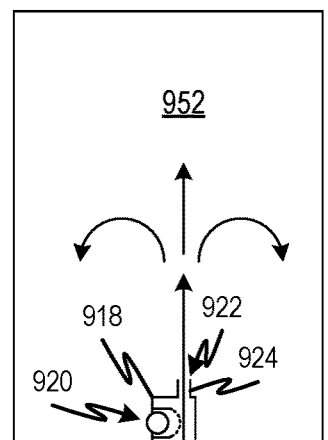
Figure 8G:
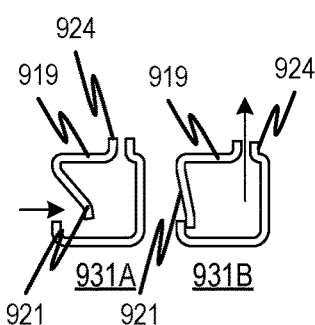
Figure 8E:
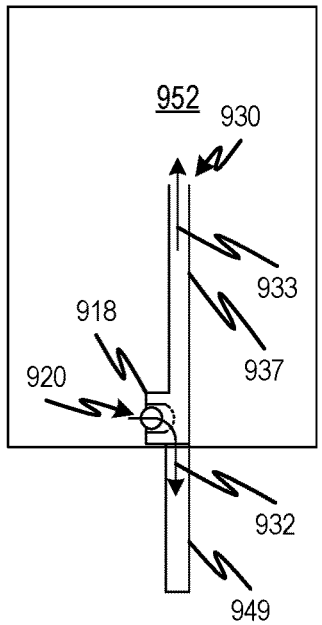
Figure 8F:
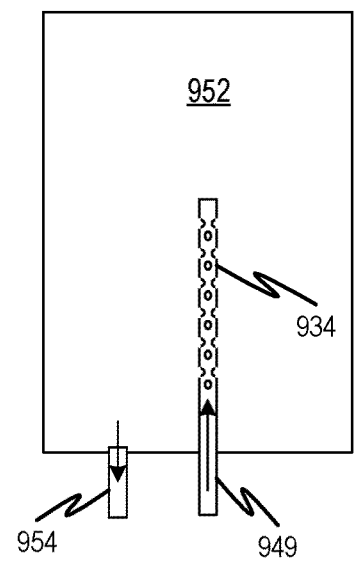

FIGS. 8C through 8F show various features to promote mixing of fluids in a mixing container according to embodiments of the disclosed subject matter. A mixing container 952 uses a single mixing container inlet and outlet line 949 that functions as a mixing container inlet and outlet line 949. FIG. 8C shows a fluid outgoing from the mixing container 952 and FIG. 8D shows fluid incoming into the mixing container 952. A two way header 924 has a check valve 918 that allows outgoing fluid to be drawn through an opening 920 into the mixing container inlet and outlet line 949 but blocks flow out of the opening 920. When flow fluid is pumped into the mixing container 952, the check valve 918 closes and all of the flow is forced through a nozzle 924 so that it emerges at high velocity from a nozzle opening 922 as illustrated in FIG. 8D. As result, mixing is promoted and a substantial convective flow or jet is generated to transport the incoming flow to locations remote from the opening 920, thereby promoting mixing. A similar effect is obtained in the embodiment of FIG. 8E in which incoming flow is released from a tube 937 inside the mixing container 952 from an opening 930 remote from the opening 920. In this embodiment, also, a check valve 918 causes the incoming flow 933 and outgoing flow 932 to take different paths. Note that a check valve, although not shown, may be incorporated in the flow path of the tube 937 or the nozzle 924 to block flow through opening 922 or 930 when fluid is pumped out of the mixing container 952 to enhance the separation effect between the ingoing and outgoing flows. FIG. 8F shows an embodiment in which the container inlet and outlet line 949 attaches to a header tube 934 that is similar in structure to a peritoneal catheter in that it has openings distributed along a portion of its length such that ingoing flows are distributed. Such a header tube 934 may be used as a single container inlet and outlet line as for 949 or, in combination with a dedicated outline line 954, as an inlet line. In the foregoing embodiments, instead of a check valve, a flexible member such as a reed or flap valve as indicated in FIG. 8G, which creates greater resistance for flow in one direction than another, may be employed. So flow does not necessarily need to be halted altogether in a selected direction to achieve substantially the above effect. In FIG. 8G, a single part that may be formed, for example, by 3D printing, assembled from parts, or molded directly has a flap 921 that bends in response to both suction and pressure resulting from pumping fluid from and to the mixing container 952 causing flow out of the mixing container to be drawn through the inlet covered by the flap 921 and to be projected by the nozzle 924 when fluid is pumped into the mixing container as described with reference to FIGS. 8C and 8D. Here the flap 921 need not fully close or open but may, in embodiments, merely create a differential resistance to ingoing and outgoing flows (931A and 931B, respectively) such that fluid pumped into the mixing container is projected away from the location where it is drawn in, thereby facilitating the mixing process.

Figure 4L:
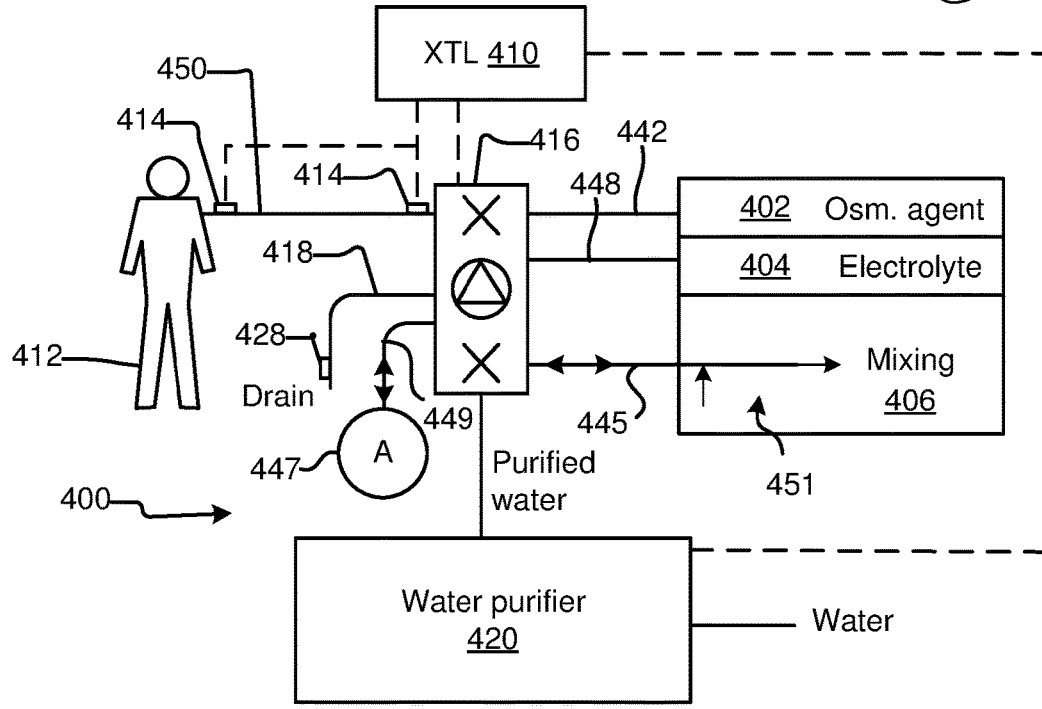
FIG. 4L shows a peritoneal dialysis solution admixer/cycler similar to that of FIG. 4A in which a single mixing container line connects a valve network to the mixing container.

FIG. 4L illustrates schematically a variation of the peritoneal dialysis solution admixer/cycler 400 of FIG. 4A with the addition of an accumulator 447 connected by an accumulator line 449 to allow a pump such as a peristaltic pump according to any of the disclosed embodiments, to allow mixing with a single mixing container line 445 connecting the mixing container 406. The controller 410 pumps fluid from the mixing container 406 to the accumulator 447 back and forth multiple times to mix the contents of the mixing container 406. This is in contrast to the disclosed embodiments in which two lines connect the mixing container 406 to the fluid circuit with pump and valve network 416. As indicated, use of a pump that has the ability to accumulate fluid, such as a diaphragm pump, may allow fluid to be pumped into an out of the mixing container 406 without a separate accumulator 447 by pumping fluid into the mixing container 406 from the diaphragm pump internal volume. Reference numeral 451 points to the arrows indicating spaced ingoing and outgoing flows to/from the mixing container that may be provided by the foregoing embodiments of devices for separating (at least partially) the ingoing and outgoing flows.

Figure 9A:
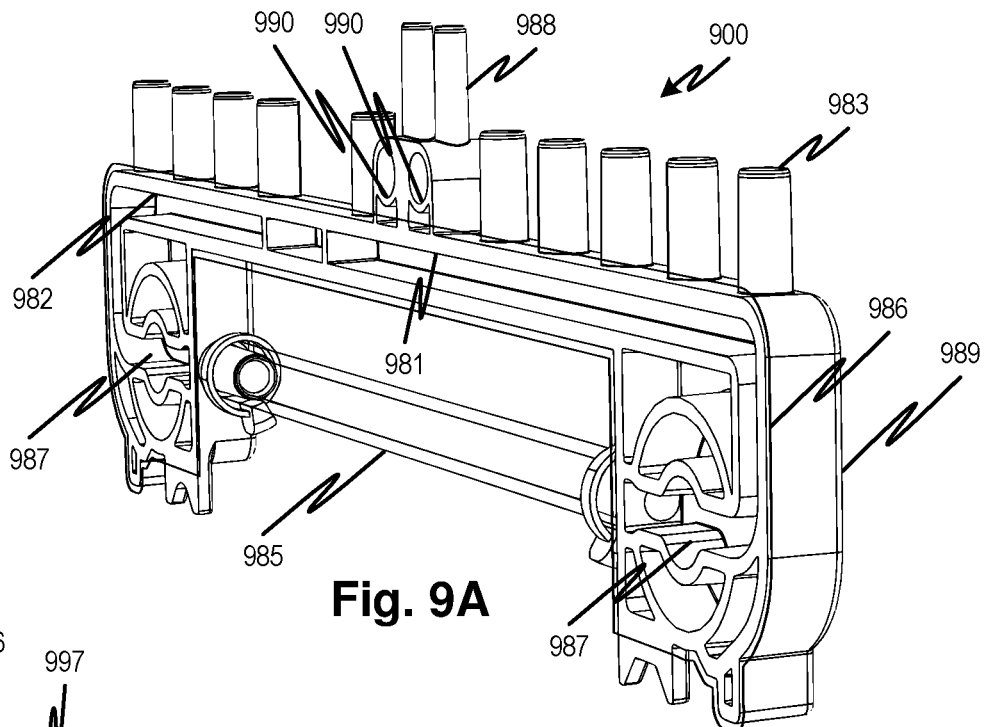
FIG. 9A shows a manifold according to embodiments of the disclosed subject matter.

Referring to FIG. 9A, a manifold 900, which functions as manifold 174, has two chambers 982 and 981 defined by the shape of a rigid housing 989 that is sealed by a welded or bonded film 986. Rigid house 989 may be formed by casting and an internal volume sealed by the bonded film. The film has regions 987 overlying the housing for pressure detection. Pressure transducers (not shown) contacts the regions 987 and detects a force applied by pressure within the chambers 982 and 981 at either end of a pumping tube segment 985 which connects the two chambers 982 and 981. Respective ones of ports 983, for the various fluids described herein according to the different embodiments, convey fluid to respective ones of the chambers 982 and 981. Tubes may be friction fitted or bonded to the ports 983. The ports 988 have air-lines attached to them and these are respectively fluidly coupled to air ports 990 which sealingly engage pressure transducers (See 146 and 147 of FIG. 2B). In other embodiments, the rigid housing 989 is replaced with a fully enclosed housing (not shown) with pod type pressure sensors embedded in them and there is no film required for sealing the structure closed.

Figure 9B:
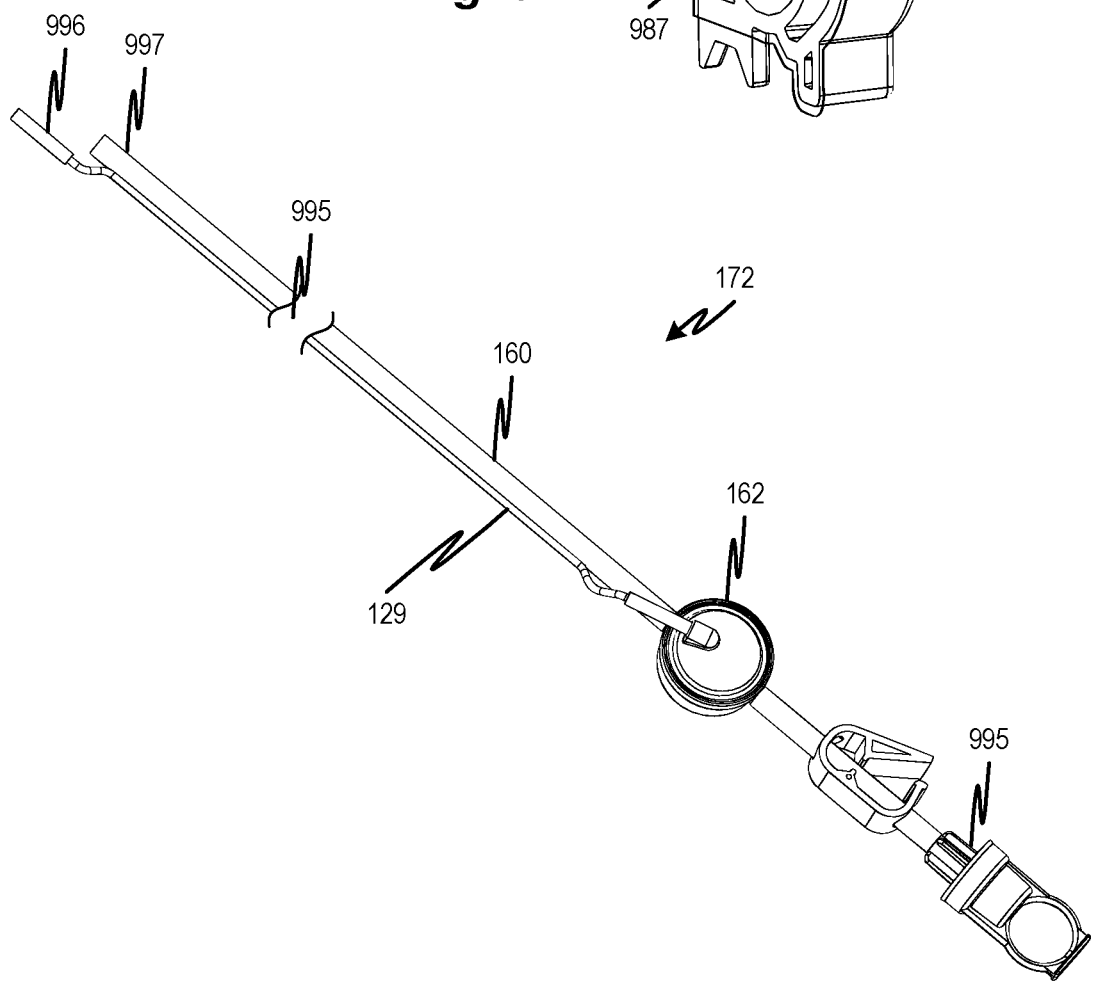
FIG. 9B shows a peritoneal dialysis fill/drain line according to embodiments of the disclosed subject matter.

Referring to FIG. 9B, a dialysis solution line 172 has a pre-connected fill-drain line 160 and an air-line 129 as well as a pressure-sensing pod 162 which has an internal diaphragm which is displaced responsively to pressure changes in the pre-connected fill-drain line 160 near the patient connector 995. Movement of the internal diaphragm compresses or expands an air volume in the air-line 129 which is conveyed to a connector 996. The patient connector 995 connects to a peritoneal catheter. The proximal end 997 of the pre-connected fill-drain line 160 is attached or bonded to a respective one of the ports 983.

Figure 10A:
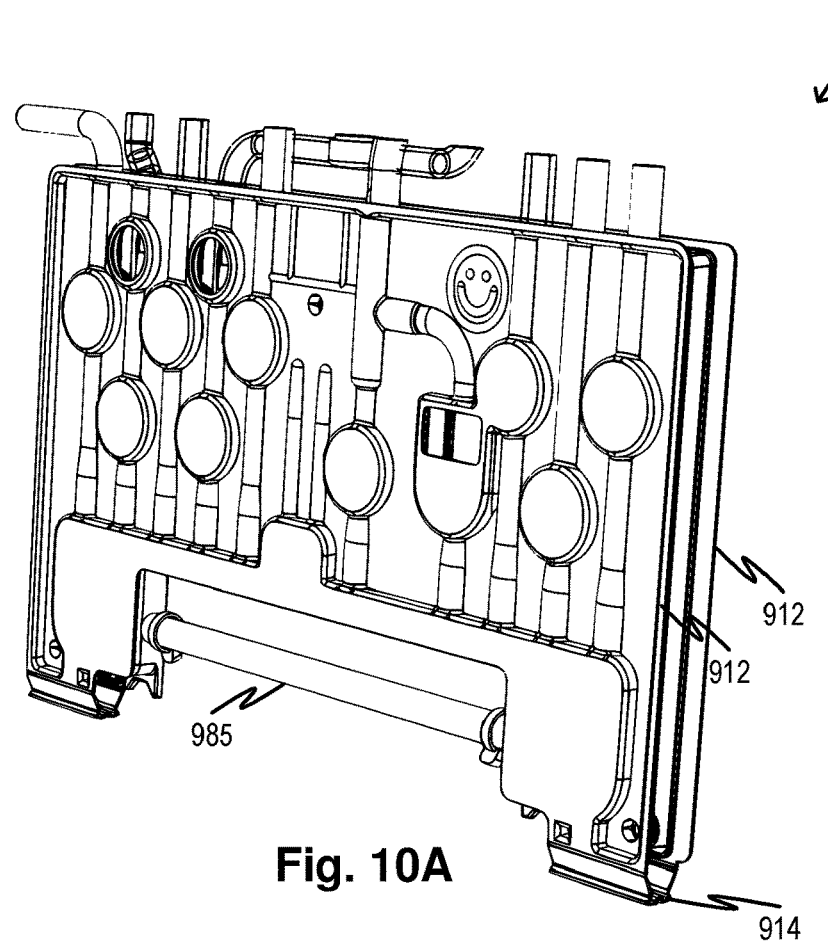
FIGS. 10A and 10B show the structure of a valve network portion of a fluid circuit according to embodiments of the disclosed subject matter.
Figure 10B:
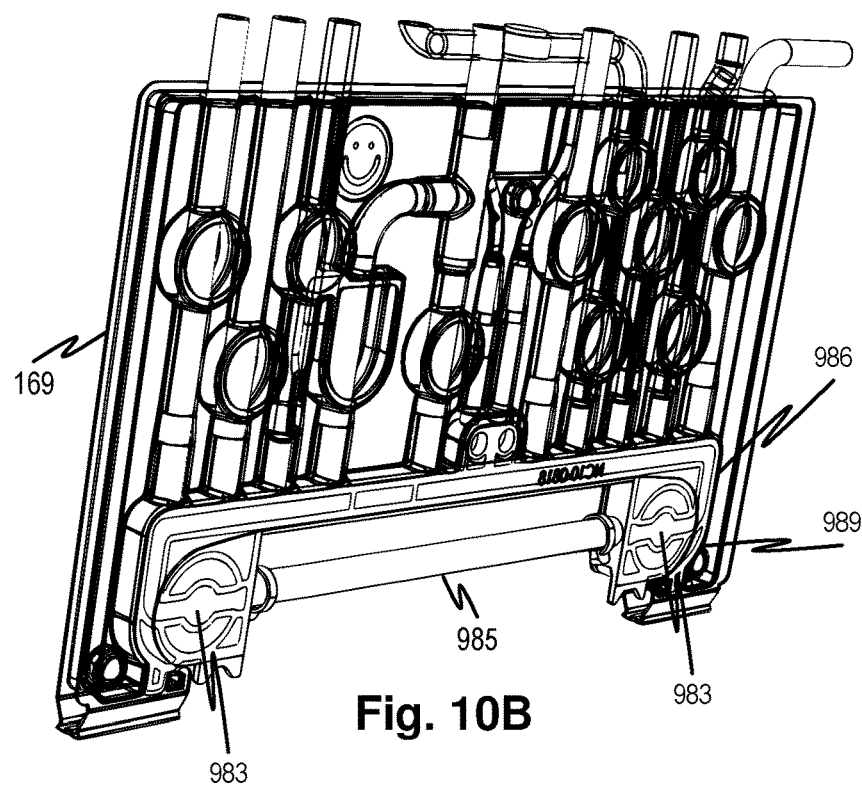
Figure 11:
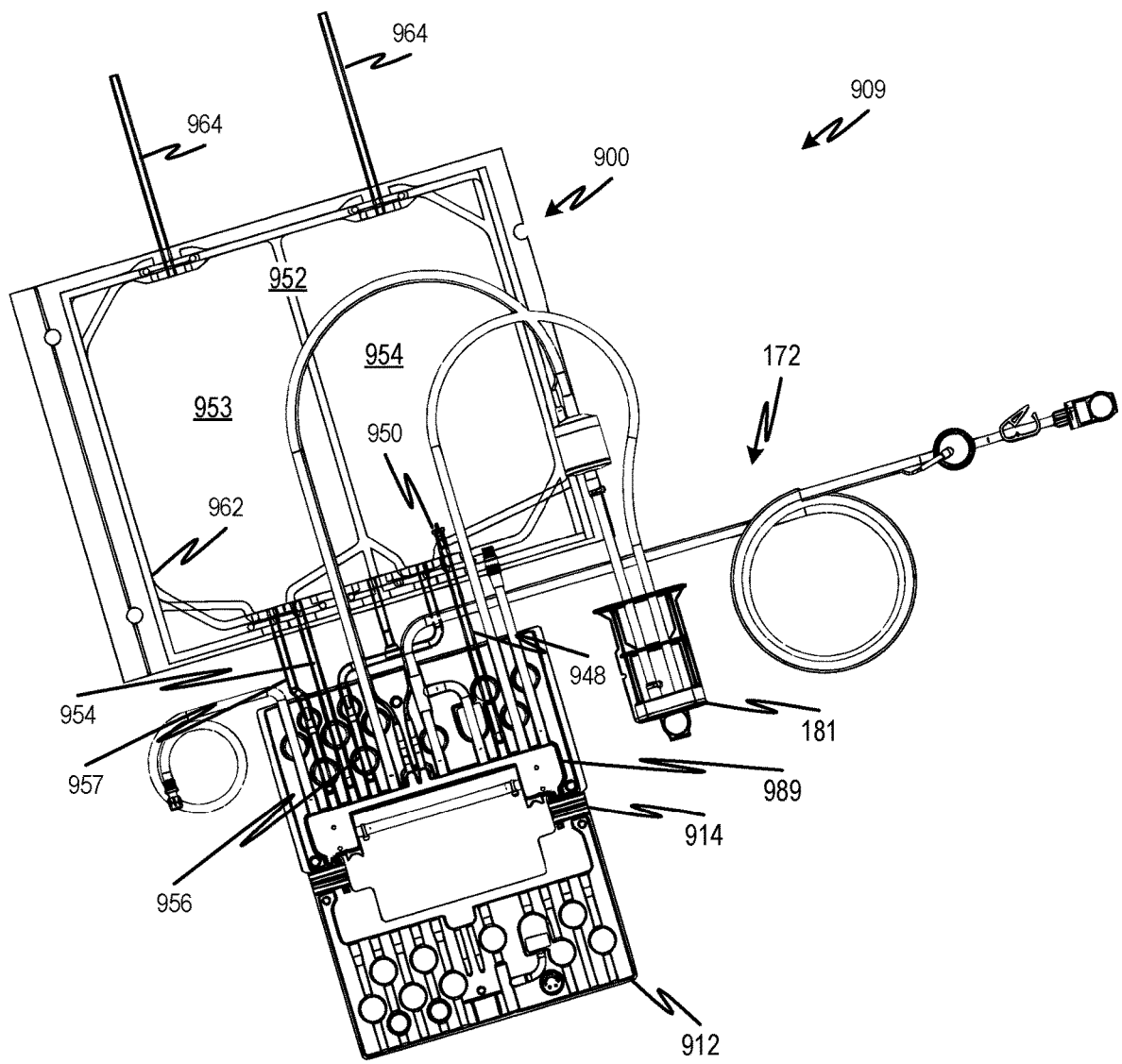
FIG. 11 shows a fluid circuit for peritoneal dialysis according to embodiments of the disclosed subject matter.

Referring now to FIGS. 10A and 10B, a cartridge portion 910 of the fluid circuits according to the various embodiments provides the manifold and the pumping and pressure sensing portions previously described. The cartridge support 169 may be made from a single panel 912 that is folded at a pair of creases indicated at 914. The panels contain recesses for all the tubes held between them precisely controlling their positions. A compartment is defined by the shapes of the panels to hold the rigid housing 989. FIG. 2A shows an alternative embodiment in which the manifold 174 is connected by a battery of tubes indicated collectively at 200C so the double panel structure is not directly attached to the manifold 174. FIG. 11 shows the single vacuum formed panel 912 before it is closed about the pair of creases 914. FIG. 11 otherwise shows a complete fluid circuit 909 including how the features of 8A through 10B are assembled in a completed fluid circuit 909.

According to first embodiments, the disclosed subject matter includes a peritoneal dialysis treatment method that includes connecting a fluid circuit to a peritoneal dialysis treatment, such as a peritoneal dialysis treatment, component, in which the fluid circuit includes a mixing container. The peritoneal dialysis treatment, such as a peritoneal dialysis treatment, component has actuators and at least one sensor that engage with the fluid circuit when the peritoneal dialysis treatment, such as a peritoneal dialysis treatment, component receives the fluid circuit such as by connecting the fluid circuit with mounting points, insertion in a slot, or some other alignment mechanism. The method further includes connecting one or more containers of medicament concentrate to the peritoneal dialysis treatment, such as a peritoneal dialysis treatment, component. Each container may have sufficient medicament concentrate to supply multiple peritoneal dialysis treatments. The method further includes flowing purified water and concentrate through the peritoneal dialysis treatment, such as a peritoneal dialysis treatment, component to the fluid circuit to mix a diluted medicament using the concentrate. The flowing operation may include flowing water and concentrate through at least one sterilizing filter. A sterilizing filter, or sterilizing filter, is one which sterilizes the fluid flowing through it by blocking the passage of large particles such as large molecules, bacteria, bacteria fragments, and other substances other than solutes which are used in the medicament. The method further includes treating a patient using diluted medicament concentrate using the peritoneal dialysis treatment, such as a peritoneal dialysis treatment, component. The diluted medicament concentrate is the medicament that is used to treat the patient. The medicament may, in a principal embodiment, be peritoneal dialysis solution. It may be any type of medicament that can be formed at the point of use from concentrate by dilution. The method further includes testing an integrity of the at least one sterilizing filter, replacing the fluid circuit and repeating the connecting a fluid circuit, flowing purified water and concentrate, treating a patient, and testing multiple times without repeating the connecting of one or more containers of medicament concentrate. In other words, the peritoneal dialysis treatment is repeated without replacing the source of concentrate.

In variations thereof, the first embodiments include ones in which, the at least one filter is integrally attached to the fluid circuit. In variations thereof, the first embodiments include ones in which the flowing water and concentrate through at least one sterilizing filter includes flowing water and concentrate through separate filters.

According to second embodiments, the disclosed subject matter includes a fluid circuit for peritoneal dialysis and dialysis solution preparation. A disposable mixing container of polymeric material has a pre-connected fluid circuit, the mixing container and fluid circuit are sealed from an external environment. The fluid circuit includes a fluid flow director that includes a valve network that has junctions and valve portions that mechanically interface with valve actuators to define selectable flow paths in the valve network. The valve network further includes at least two concentrate lines terminated by respective concentrate line connectors, a water line terminated by a water line connector, and a pair of lines connected to the mixing container to permit simultaneous flow into, and flow out from, the mixing container. Each of the concentrate and water lines has an in-line sterilizing filter with an air-line attached to a respective one of the in-line sterilizing filters, the air-line is connected to the respective one such that air forced through the air-line applies pressure to a membrane of the in-line sterilizing filter to permit an integrity test of the filter. If a lack of integrity is determined a corrective action may be taken by the controller. The valve network is embodied in a cartridge with a pumping portion that has a rigid manifold, the manifold being hollow and defining at least some of the junctions and the air-lines connecting to ports fixedly attached to the manifold. The manifold chamber is rigid and defining two separate chambers connected by a pumping tube segment. The air-lines are each collinear with at least a portion of a respective one of the concentrate and water lines. This means they run continuously and parallel together because they are inter-attached along their lengths.

In variations thereof, the second embodiments include ones in which the air-lines are each integral with at least a portion of a respective one of the concentrate and water lines. In still other examples of the second embodiments, the manifold chamber has pressure sensors integrated therein, one at each end of the pumping tube segment. In variations thereof, the second embodiments include ones in which the pumping tube segment is straight. In variations thereof, the second embodiments include ones in which the pressure sensor includes a pressure pod with a diaphragm that serves as a portion of a wall of a respective one of the two separate chambers. In still other examples of the second embodiments, the respective concentrate line connectors are connected by a frame that support portions of the concentrate lines. In still other examples of the second embodiments, the frame has a window and the portions of the concentrate lines pass across the window. In still other examples of the second embodiments, the valve network has a drain line. In still other examples of the second embodiments, the drain and water lines connected by a frame that support portions of the drain and water lines. In still other examples of the second embodiments, the frame has a window and portions of the drain and water lines pass across the window. In still other examples of the second embodiments, the valve portions are supported by a planar element. In still other examples of the second embodiments, the planar element includes a pair of sheets shaped to hold the valve portions in predefined positions. In still other examples of the second embodiments, the planar element includes a pair of sheets shaped to hold the valve portions in predefined positions, at least one of the pair of sheets has holes in it to permit valve actuators to contact the valve portions. In still other examples of the second embodiments, the valve portions are tube segments. In still other examples of the second embodiments, the cartridge includes parallel panels with the valve network sandwiched between them, the at least two frangible seals are held in the cartridge aligned with windows in at least one of the panels to permit an actuator to fracture them prior to use thereby allowing the concentrate to flow through the at least two concentrate lines.

According to third embodiments, the disclosed subject matter includes a peritoneal dialysis solution admixer/cycler. The embodiments include at least two concentrate containers with concentrate supply connectors. The concentrate containers have sufficient concentrate to perform multiple peritoneal dialysis treatments, where each peritoneal dialysis treatment includes multiple fill/drain cycles. A daily disposable component includes a disposable mixing container of polymeric material with a pre-connected fluid circuit, the mixing container and fluid circuit are sealed from an external environment. The daily disposable component may be used on a different schedule rather than daily, for example, it may be used to perform peritoneal dialysis treatments once every couple of days or less or more frequently than daily. So, the term "daily disposable component" highlights a range of frequencies of use and embodiments. The fluid circuit includes a fluid flow director that includes a valve network that has junctions and valve portions that mechanically interface with valve actuators to define selectable flow paths in the valve network. The valve network further includes at least two concentrate lines terminated by respective concentrate line connectors, a water line terminated by a water line connector, and a pair of lines connected to the mixing container to permit simultaneous flow into, and flow out from, the mixing container. The concentrate line connectors are connectable to the concentrate supply connectors. Each of the concentrate and water lines has an in-line sterilizing filter with an air-line attached to a respective one of the in-line sterilizing filters, the air-line is connected to the respective one such that air forced through the air-line applies pressure to a membrane of the in-line sterilizing filter to permit an integrity test thereof. The valve network is embodied in, held by, or supported by a cartridge that also has a pumping portion supported by a rigid manifold, the manifold being hollow and defining at least some of the junctions and the air-lines connecting to ports fixedly attached to the manifold. The manifold chamber is rigid and defines two separate chambers connected by a pumping tube segment.

Other examples of the third embodiments include a connection platform that mechanically supports the concentrate line connectors and the concentrate supply connectors to facilitate their interconnection. Other examples of the third embodiments include a connection platform that fluidly couples the concentrate line connectors and the concentrate supply connectors to facilitate their interconnection. In other examples of the third embodiments, the air-lines are each collinear with at least a portion of a respective one of the concentrate and water lines. In other examples of the third embodiments, the air-lines are each integral with at least a portion of a respective one of the concentrate and water lines. In other examples of the third embodiments, the manifold chamber has pressure sensors integrated therein, one at each end of the pumping tube segment. In other examples of the third embodiments, the pumping tube segment is straight. In other examples of the third embodiments, the pressure sensor includes a pressure pod with a diaphragm that serves as a portion of a wall of a respective one of the two separate chambers. In other examples of the third embodiments, the respective concentrate line connectors are connected by a frame that supports portions of the concentrate lines. In other examples of the third embodiments, the frame has a window and the portions of the concentrate lines pass across the window. In other examples of the third embodiments, the valve network has a drain line. In other examples of the third embodiments, the drain and water lines are connected by a frame that supports portions of the drain and water lines. In other examples of the third embodiments, the frame has a window and portions of the drain and water lines pass across the window. In other examples of the third embodiments, the valve portions are supported by a planar element.

In other examples of the third embodiments, the planar element includes a pair of sheets shaped to hold the valve portions in predefined positions. In other examples of the third embodiments, the planar element includes a pair of sheets shaped to hold the valve portions in predefined positions, and at least one of the pair of sheets has holes in it to permit valve actuators to contact the valve portions. In other examples of the third embodiments, the valve portions are tube segments. In other examples of the third embodiments, the fluid circuit has a drain line with a drain connector and the connection platform includes a water supply connector and a drain connector to which the water line connector and the drain connector are respectively connectable. In other examples of the third embodiments, the fluid circuit has a drain line with a drain connector and the connection platform includes a water supply connector and a drain connector to which the water line connector and the drain connector are respectively connected. In other examples of the third embodiments, the at least two concentrate containers are contained in a single package. In other examples of the third embodiments, the single package is housed by a single box. In other examples of the third embodiments, the single box is of cardboard. In other examples of the third embodiments, the at least two concentrate containers are cylindrical containers.

According to fourth embodiments, the disclosed subject matter includes a fluid system for dialysis solution preparation. A disposable mixing container is of polymeric material with a pre-connected fluid circuit. The mixing container and fluid circuit are sealed from an external environment. A concentrate container of polymeric material is pre-connected to the fluid circuit. The concentrate container is sealed from an external environment. The fluid circuit includes a valve network that has junctions and valve portions to define selectable flow paths in the valve network. The valve network further includes a concentrate line connected to the concentrate container, a water line terminated by a water line connector, and one or a pair of lines connected to the mixing container to permit intermittent of simultaneous flow into, and flow out from, the mixing container. The water line has an in-line sterilizing filter with an air-line attached thereto, the air-line is connected such that air forced through the air-line applies pressure to a membrane of the in-line sterilizing filter to permit an integrity test thereof. An actuator device has valve actuators, sensors, and a pumping actuator. The fluid circuit has sensor and pumping portions that engage, respectively, along with said valve portions, with the valve actuators, sensors, and a pumping actuator, respectively, of the actuator device.

According to variations thereof, the fourth embodiments are ones in which the valve network is in a cartridge with the pumping portion held by a rigid manifold thereof, the manifold is hollow and defining at least some of said junctions. According to variations thereof, the fourth embodiments are ones in which the air-line connects to a port fixedly attached to said manifold. According to variations thereof, the fourth embodiments are ones in which the manifold is rigid and has two separate chambers connected by the pumping portion. According to variations thereof, the fourth embodiments are ones in which the valve network is supported by a panel providing support for the cartridge, the manifold is connected to the panel. According to variations thereof, the fourth embodiments are ones in which the valve network is supported by a panel, the manifold is spaced apart from the panel. According to variations thereof, the fourth embodiments are ones in which each of said two separate chambers has a pressure sensor integrated therein, one at each end of said pumping portion. According to variations thereof, the fourth embodiments are ones in which each pressure sensor includes a pressure pod with a diaphragm that serves as a portion of a wall of a respective one of the two separate chambers. According to variations thereof, the fourth embodiments are ones in which respective concentrate line connectors are connected by a frame that supports a portion of the concentrate line. According to variations thereof, the fourth embodiments are ones in which the frame has a window and the portion of the concentrate line passes across the window. According to variations thereof, the fourth embodiments are ones in which the valve network has a drain line. According to variations thereof, the fourth embodiments are ones in which the valve network has a fill/drain line connectable to a peritoneal catheter. According to variations thereof, the fourth embodiments are ones in which the valve network has a fill/drain line connectable to a peritoneal catheter. According to variations thereof, the fourth embodiments are ones in which the fill/drain line is pre-connected to the valve network and sealed by a removable end cap.

According to variations thereof, the fourth embodiments are ones in which the drain and water lines are connected by a frame that supports portions of the drain and water lines. According to variations thereof, the fourth embodiments are ones in which the frame has a window and a portion of the concentrate line crosses the window. According to variations thereof, the fourth embodiments are ones in which the valve portions are supported by a planar element. According to variations thereof, the fourth embodiments are ones in which the planar element includes a pair of sheets shaped to hold the valve portions in predefined positions. According to variations thereof, the fourth embodiments are ones in which the planar element includes a pair of sheets shaped to hold the valve portions in predefined positions, at least one of the pair of sheets has holes in it to permit valve actuators to contact the valve portions. According to variations thereof, the fourth embodiments are ones in which the valve portions are tube segments. According to variations thereof, the fourth embodiments are ones in which the valve portions are tube segments. According to variations thereof, the fourth embodiments are ones in which the concentrate line is sealed by a frangible seal. According to variations thereof, the fourth embodiments are ones in which the panel is one of two parallel panels with said valve network sandwiched between them, the valve portion held in alignment with a window in at least one of the two parallel panels to permit an actuator to access the valve portion. According to variations thereof, the fourth embodiments are ones in which the two parallel panels are portions of a single folded panel. According to variations thereof, the fourth embodiments are ones in which the valve network includes the concentrate line which is sealed by a frangible seal thereby separating the concentrate from a remainder of the fluid circuit until the frangible seal is fractured.

According to variations thereof, the fourth embodiments are ones that include a second sterilizing filter connected in series with said in-line sterilizing filter by a flow channel to prevent grow-through contamination between membranes thereof. According to variations thereof, the fourth embodiments are ones in which the mixing container and concentrate container are defined by two bonded flexible panels along seams to define the mixing container and concentrate container. According to variations thereof, the fourth embodiments are ones in which the seams are integral as formed by welding or adhesive bonding. According to variations thereof, the fourth embodiments are ones in which the fluid circuit encloses a sterile internal volume. According to variations thereof, the fourth embodiments are ones in which the actuator device includes a peritoneal dialysis cycler. According to variations thereof, the fourth embodiments are ones in which the actuator device includes a peritoneal dialysis cycler. According to variations thereof, the fourth embodiments are ones in which the actuator device has a cut-and-seal device and a receiving slot that receives said frame and aligns the window with the cut-and-seal device. According to variations thereof, the fourth embodiments are ones in which the actuator device has a controller programmed to activate the cut-and-seal device to cut and seal said concentrate line thereby permitting the fluid circuit to be separated from the frame and a stub portion of the concentrate line. According to variations thereof, the fourth embodiments are ones in which the frame and a stub portion of the concentrate line collectively remain in place on the actuator device when separated from the fluid circuit. According to variations thereof, the fourth embodiments are ones in which the frame and stub portion act as a seal on connectors of the actuator device.

According to fifth embodiments, the disclosed subject matter includes a system for the preparation of sterile peritoneal dialysis fluid that includes a disposable fluid circuit with a pumping tube segment and multiple valve segments, and a peritoneal dialysis solution admixer/cycler dialysis treatment device with at least one pumping actuator positioned to engage the at least one pumping tube segment and multiple valve actuators positioned to engage the valve segments. A first of the multiple valve segments is connected to a fluid inlet. The disposable fluid circuit has a sterilizing filter connected between a fluid inlet connector and the first of the multiple valve segments. A first concentrate container has sufficient concentrate for the preparation of enough peritoneal dialysis solution to perform multiple peritoneal dialysis treatments, wherein each peritoneal dialysis treatment includes multiple fill/drain cycles. The disposable fluid circuit has an integrally-attached mixing container sized to hold sufficient peritoneal dialysis solution for at least a single fill/drain cycle. An interconnection module has a primary concentrate connector and a primary water connector, to which the first concentrate container is connected once every multiple peritoneal dialysis treatments, the interconnection module also has a common secondary connector to which the disposable fluid circuit fluid inlet connector is connected once every peritoneal dialysis treatment. The interconnection module has a valve network controlled by the programmable controller that selects water or concentrate to be drawn by the peritoneal dialysis solution admixer/cycler dialysis treatment device through the common secondary connector. The peritoneal dialysis solution admixer/cycler dialysis treatment device has a programmable controller programmed to control the pumping actuator to pump concentrate and water into the mixing container to make a batch of peritoneal dialysis fluid and subsequently to perform a fill/drain cycle, which includes draining spent peritoneal dialysis solution and pumping a fill of the peritoneal dialysis solution from the mixing container.

In other examples of the fifth embodiments, the disposable fluid circuit has a second concentrate inlet with a sterilizing filter connected between the second concentrate inlet and a third of the multiple valve segments. Other examples of the fifth embodiments include a second concentrate container that includes concentrate for the preparation of enough peritoneal dialysis solution to perform multiple peritoneal dialysis treatments, wherein each peritoneal dialysis treatment includes multiple fill/drain cycles, wherein the first and second concentrate inlets are connected to the first and second concentrate containers by a double connector that carries the first concentrate inlet connector and a second concentrate inlet connector of the disposable fluid circuit, the double connector making connections for the first concentrate inlet connector and the second concentrate inlet simultaneously to the first and second concentrate containers. Other examples of the fifth embodiments include a controller, the controller is programmed to calculate and store data representing a volume of water or concentrate remaining in a portion of the valve network after selecting water or concentrate to be drawn by the peritoneal dialysis solution admixer/cycler dialysis treatment device and to control the pump responsively to the data representing a volume of water or concentrate.

According to sixth embodiments, the disclosed subject matter includes a method of performing a peritoneal dialysis treatment. The method includes drawing a concentrate and water through a sterilizing filter in predefined quantities to make a sufficient quantity of peritoneal dialysis solution for a peritoneal dialysis treatment of multiple fill/drain cycles. The drawing includes, using an interconnection module, connecting water and concentrate in succession to a common inlet of a disposable fluid circuit to which the sterilizing filter is integrally attached. The method further includes testing the sterilizing filter by means of an air pressure test and using, or preventing use of, the quantity for a peritoneal dialysis fill and drain cycle depending on a result of the testing.

Other examples of the sixth embodiments include connecting a long-term concentrate container to the interconnection module once every multiple peritoneal dialysis treatments. Other examples of the sixth embodiments include connecting a peritoneal dialysis treatment circuit that has the sterilizing filter integrally attached thereto, to the interconnection module once every single peritoneal dialysis treatment. Other examples of the sixth embodiments include mixing the water and the concentrate.

In other examples of the sixth embodiments, the drawing and the mixing are performed using a single common pump.

According to seventh embodiments, the disclosed subject matter includes a method of performing a peritoneal dialysis treatment. The method includes drawing a concentrate and water through respective sterilizing filters in predefined quantities to make a sufficient quantity of peritoneal dialysis solution for a single fill of a peritoneal dialysis treatment. The drawing includes, using an interconnection module, flowing water and concentrate in succession to a mixing container by switching flow paths in a peritoneal dialysis cycler. The method further includes testing the sterilizing filter by means of an air pressure test and using, or preventing use of, the quantity for a peritoneal dialysis fill and drain cycle depending on a result of the testing.

Other examples of the seventh embodiments include connecting a long-term concentrate container to the interconnection module once every multiple peritoneal dialysis treatments. Other examples of the seventh embodiments include connecting a peritoneal dialysis treatment circuit that has the respective sterilizing filters integrally attached thereto, to the interconnection module once every single peritoneal dialysis treatment. Other examples of the seventh embodiments include mixing the water and the concentrate. In other examples of the seventh embodiments, the drawing and the mixing are performed using a single common pump. Other examples of the seventh embodiments include the connecting a peritoneal dialysis treatment circuit and removing at least one sterile seal from water and concentrate connectors and connecting one or more new connectors of the peritoneal dialysis treatment circuit to water and concentrate connectors and wherein following the using the quantity, cutting one or more portions of the one or more new connectors to create at least one new sterile seal. In other examples of the seventh embodiments, the interconnection module supports a connector of the concentrate container, the connecting of a long-term concentrate connector which includes replacing the connector of the concentrate container, and the connecting a peritoneal dialysis treatment circuit includes connecting the peritoneal dialysis treatment circuit to the connector of the concentrate container. In other examples of the seventh embodiments, the connecting water and concentrate in succession using the interconnection module includes washing a fixed volume of concentrate from a common outlet of the interconnection module and the disposable fluid circuit inlet, the method further comprising, using a controller used to make the sufficient quantity, calculating an amount of the fixed volume and controlling an amount of water pumped to form the sufficient quantity responsively to a result of the calculating.

According to eighth embodiments, the disclosed subject matter includes a method of making a fluid circuit that has a chamber prefilled with medicament concentrate. The method includes integrally connecting a fluid circuit with a chamber and connecting a sterilizing filter with the chamber. The method is performed in such a way that the integrally connecting and connecting a sterilizing filter form an assembly with a sealed volume that is separated from the outside environment by walls thereof, a frangible plug in a concentrate outlet line stemming from the chamber, and a membrane of the sterilizing filter. The method includes sterilizing the assembly and sterile-filling the chamber with concentrate through the sterilizing filter. The method further includes heat welding and cutting a line connecting the sterilizing filter and the chamber and finally subjecting the fluid circuit and chamber to gamma or e-beam sterilization to terminally sterilize the same. In the embodiments, the sterilizing filter is not one integrated in the product—e.g. pre-connected to multiple daily disposable components. Also, instead of cutting and heat welding, lines may be sealed by crimping a permanent clip or other means.

According to ninth embodiments, the disclosed subject matter includes a fluid circuit for peritoneal dialysis and dialysis solution preparation. The circuit includes a disposable mixing container of polymeric material with a pre-connected fluid circuit, the mixing container and fluid circuit being sealed from an external environment. A concentrate container is of polymeric material and is pre-connected to the fluid circuit and sealed from an external environment. The fluid circuit includes a fluid flow director that includes a valve network that has junctions and valve portions that mechanically interface with valve actuators to define selectable flow paths in the valve network. The valve network further includes a concentrate line connected to the concentrate container, a water line terminated by a water line connector, and a pair of lines connected to the mixing container to permit simultaneous flow into, and flow out from, the mixing container. The water line has an in-line sterilizing filter with an air-line attached thereto, the air-line is connected such that air forced through the air-line applies pressure to a membrane of the in-line sterilizing filter to permit an integrity test thereof. The valve network is embodied in a cartridge with a pumping portion that has a rigid manifold, the manifold being hollow and defining at least some of the junctions, and the air-line connects to a port fixedly attached to the manifold. The manifold is rigid and includes two separate chambers connected by a pumping tube segment.

In other examples of the ninth embodiments, the air-line is collinear with at least a portion of a respective one of the concentrate and water lines. In other examples of the ninth embodiments, the valve network is supported by a panel, and the manifold is connected to the panel. In other examples of the ninth embodiments, the valve network is supported by a panel, and the manifold is spaced apart from the panel. In other examples of the ninth embodiments, the air-line is integral with at least a portion of a respective one of the concentrate and water lines. In other examples of the ninth embodiments, the manifold chamber has pressure sensors integrated therein, one at each end of the pumping tube segment. In other examples of the ninth embodiments, the pumping tube segment is straight. In other examples of the ninth embodiments, pressure sensor includes a pressure pod with a diaphragm that serves as a portion of a wall of a respective one of the two separate chambers. In other examples of the ninth embodiments, respective concentrate line connectors are connected by a frame that supports a portion of the concentrate line. In other examples of the ninth embodiments, the frame has a window and a portion of the concentrate line passes across the window. In other examples of the ninth embodiments, the valve network has a drain line. In other examples of the ninth embodiments, the valve network has a fill/drain line connectable to a peritoneal catheter. In other examples of the ninth embodiments, the fill/drain line is sealed by a removable end cap.

In other examples of the ninth embodiments, the fill/drain line has a second air-line collinear with the fill/drain line, connected at an end of the fill/drain line to a pressure pod connected to the fill/drain line to measure a pressure therewithin. In other examples of the ninth embodiments, the drain and water lines are connected by a frame that supports portions of the drain and water lines. In other examples of the ninth embodiments, the frame has a window and portions of the drain and water lines pass across the window. In other examples of the ninth embodiments, the valve portions are supported by a planar element. In other examples of the ninth embodiments, the planar element includes a pair of sheets shaped to hold the valve portions in predefined positions. In other examples of the ninth embodiments, the planar element includes a pair of sheets shaped to hold the valve portions in predefined positions, at least one of the pair of sheets having holes to permit valve actuators to contact the valve portions. In other examples of the ninth embodiments, the valve portions are tube segments. In other examples of the ninth embodiments, the concentrate line is sealed by a frangible seal. In other examples of the ninth embodiments, the cartridge includes parallel panels with the valve network sandwiched between them, and the frangible seal is held in the cartridge aligned with windows in at least one of the panels to permit an actuator to fracture them prior to use thereby allowing the concentrate to flow through the concentrate line. In other examples of the ninth embodiments, the cartridge includes a single folded panel forming parallel panel portions with the valve network sandwiched between them, and the frangible seal is held in the cartridge aligned with windows in at least one of the panels to permit an actuator to fracture them prior to use thereby allowing the concentrate to flow through the concentrate line. In other examples of the ninth embodiments, the valve network includes the concentrate line which is sealed by a frangible seal thereby separating the concentrate from the rest of the fluid circuit until the frangible seal is fractured.

Other examples of the ninth embodiments include a second sterilizing filter connected in series with the in-line sterilizing filter such that the second and in-line sterilizing filters are separated by a flow channel to prevent grow-through contamination between membranes thereof. In other examples of the ninth embodiments, the mixing container and concentrate container are defined by two bonded flexible panels along seams to define the mixing container and concentrate container. In other examples of the ninth embodiments, the seams are a result of thermal welding. In other examples of the ninth embodiments, the fluid circuit encloses a sterile internal volume.

According to tenth embodiments, the disclosed subject matter includes a fluid line connector with at least one thermoplastic tube supported in a frame such that the at least one thermoplastic tube is accessible from opposite sides of the frame. The frame has an overhanging ridge at one end and at least one connector that is fluidly coupled at an opposite end to the at least one thermoplastic tube. A cap is fitted to the frame to cover the at least one connector. The at least one tube extends through holes in the frame at an end thereof adjacent to the overhanging ridge. In other examples of the tenth embodiments, the frame has a recess shaped to engage a détente pin along an elongated side thereof. In other examples of the tenth embodiments, the frame has an oval-shaped recess, and the at least one connector is located within the oval-shaped recess. In other examples of the tenth embodiments, the cap fits in the oval-shaped recess to define a tortuous path between the at least one connector and an access of the oval-shaped recess. In other examples of the tenth embodiments, at least one connector and the at least one thermoplastic tubes are at least two.

According to eleventh embodiments, the disclosed subject matter includes a connector system with a connector component that has at least one thermoplastic tube supported in a frame such that the at least one thermoplastic tube is accessible from opposite sides of the frame. The frame has an overhanging ridge at one end and at least one connector that is fluidly coupled at an opposite end to the at least one thermoplastic tube. A cap is fitted to the frame to cover the at least one connector. The at least one tube extends through holes in the frame at an end thereof adjacent to the overhanging ridge. A fluid supply device with at least one supply connector that mates with the at least one connector has a portion shaped to engage the frame to align the at least one thermoplastic tube with a tube cut-and-seal device.

In other examples of the eleventh embodiments, the cut-and-seal device cuts the at least one thermoplastic tube and seals it at both cut ends, the connector component is configured to permit the at least one thermoplastic tube to be withdrawn from the one end leaving the frame and at least one connector in place on the at least one supply connector to cover and protect it from contamination until it is replaced by another connector component. In other examples of the eleventh embodiments, the frame has a recess shaped to engage a détente pin along an elongated side thereof. In other examples of the eleventh embodiments, the frame has an oval-shaped recess, and the at least one connector is located within the oval-shaped recess. In other examples of the eleventh embodiments, the cap fits in the oval-shaped recess to define a tortuous path between the at least one connector and an access of the oval-shaped recess. In other examples of the eleventh embodiments, the at least one connector and the at least one thermoplastic tubes are at least two.

According to twelfth embodiments, the disclosed subject matter includes a fluid system for peritoneal dialysis and dialysis solution preparation. A disposable mixing container of polymeric material has a pre-connected fluid circuit. The mixing container and fluid circuit are sealed from an external environment. A concentrate container is of polymeric material pre-connected to the fluid circuit. The concentrate container is sealed from an external environment. The fluid circuit includes a fluid flow director that includes a valve network that has junctions and valve portions that mechanically engage valve actuators to define selectable flow paths in the valve network. The valve network further includes a concentrate line connected to the concentrate container, a water line terminated by a water line connector, and a pair of lines connected to the mixing container to permit simultaneous flow into, and flow out from, the mixing container. The water line has an in-line sterilizing filter with an air-line attached thereto, the air-line is connected such that air forced through the air-line applies pressure to a membrane of the in-line sterilizing filter to permit an integrity test thereof. An actuator device has valve actuators, sensors, and a pumping actuator. The fluid circuit has sensor and pumping portions that engage, respectively, along with the valve portions, with effecters of the actuator device.

In other examples of the twelfth embodiments, the valve network is in a cartridge with the pumping portion held by a rigid manifold thereof, the manifold is hollow, and defines at least some of the junctions. In other examples of the twelfth embodiments, the air-line connects to a port fixedly attached to the manifold. In other examples of the twelfth embodiments, the manifold is rigid and has two separate chambers connected by the pumping portion. In other examples of the twelfth embodiments, the valve network is supported by a panel providing support for the cartridge, and the manifold is connected to the panel. In other examples of the twelfth embodiments, the valve network is supported by a panel, and the manifold is spaced apart from the panel. In other examples of the twelfth embodiments, the manifold chamber has pressure sensors integrated therein, one at each end of the pumping portion. In other examples of the twelfth embodiments, the pressure sensor includes a pressure pod with a diaphragm that serves as a portion of a wall of a respective one of the two separate chambers. In other examples of the twelfth embodiments, the respective concentrate line connectors are connected by a frame that supports a portion of the concentrate line. In other examples of the twelfth embodiments, the frame has a window and a portion of the concentrate line passes across the window. In other examples of the twelfth embodiments, the valve network has a drain line. In other examples of the twelfth embodiments, the valve network has a fill/drain line connectable to a peritoneal catheter. In other examples of the twelfth embodiments, the fill/drain line is sealed by a removable end cap. In other examples of the twelfth embodiments, the fill/drain line has a second air-line collinear with the fill/drain line, connected at an end of the fill/drain line to a pressure pod connected to the fill/drain line to measure a pressure therewithin. In other examples of the twelfth embodiments, the drain and water lines are connected by a frame that supports portions of the drain and water lines.

In other examples of the twelfth embodiments, the frame has a window and portions of the drain and water lines pass across the window. In other examples of the twelfth embodiments, the valve portions are supported by a planar element. In other examples of the twelfth embodiments, the planar element includes a pair of sheets shaped to hold the valve portions in predefined positions. In other examples of the twelfth embodiments, the planar element includes a pair of sheets shaped to hold the valve portions in predefined positions, and at least one of the pair of sheets has holes in it to permit valve actuators to contact the valve portions. In other examples of the twelfth embodiments, the valve portions are tube segments. In other examples of the twelfth embodiments, the valve portions are tube segments. In other examples of the twelfth embodiments, the concentrate line is sealed by a frangible seal. In other examples of the twelfth embodiments, the cartridge includes parallel panels with the valve network sandwiched between them, and the frangible seal is held in the cartridge and aligned with windows in at least one of the panels to permit an actuator to fracture them prior to use, thereby allowing the concentrate to flow through the concentrate line. In other examples of the twelfth embodiments, the cartridge includes a single folded panel forming parallel panel portions with the valve network sandwiched between them, and the frangible seal is held in the cartridge and aligned with windows in at least one of the panels to permit an actuator to fracture them prior to use, thereby allowing the concentrate to flow through the concentrate line. In other examples of the twelfth embodiments, the valve network includes the concentrate line which is sealed by a frangible seal thereby separating the concentrate from the rest of the fluid circuit until the frangible seal is fractured. Other examples of the twelfth embodiments include a second sterilizing filter connected in series with the in-line sterilizing filter such that the second and in-line sterilizing filters are separated by a flow channel to prevent grow-through contamination between membranes thereof. In other examples of the twelfth embodiments, the mixing container and concentrate container are defined by two bonded flexible panels along seams to define the mixing container and concentrate container. In other examples of the twelfth embodiments, the seams are a result of thermal welding. In other examples of the twelfth embodiments, the fluid circuit encloses a sterile internal volume. In other examples of the twelfth embodiments, the actuator device includes a peritoneal dialysis cycler. In other examples of the twelfth embodiments, the actuator device has a cut-and-seal device and a receiving slot that receives the frame and aligns the window with the cut-and-seal device. In other examples of the twelfth embodiments, the actuator device has a controller programmed to activate the cut-and-seal device to cut and seal the concentrate line thereby permitting the fluid circuit to be separated from the frame and the concentrate line connector, as well as from a stub portion of the concentrate line, which collectively remain in place on the actuator device to act as a seal on connectors of the actuator device.

According to thirteenth embodiments, the disclosed subject matter includes a peritoneal dialysis treatment method. The method includes connecting a fluid circuit to a fluid admixer, the fluid circuit includes a mixing container. The admixer has actuators and that engage with the fluid circuit when received thereby. The method further includes connecting one or more containers of medicament concentrate to the fluid circuit, each container has sufficient medicament concentrate for multiple peritoneal dialysis treatments and using the admixer, flowing purified water and concentrate through the fluid circuit to the mixing container to prepare a medicament in the mixing container by admixing and diluting the medicament concentrate. The flowing includes flowing water and concentrate through at least one sterilizing filter to ensure sterility of the water and concentrate. ensuring an integrity of at least one sterilizing filter by testing the at least one sterilizing filter or providing serially-connected redundant sterilizing filters. The method further includes treating a patient using the prepared medicament in the mixing container. replacing the fluid circuit with a new fluid circuit and repeating the connecting a fluid circuit, flowing purified water and concentrate, treating a patient, without replacing said one or more containers of medicament concentrate.

In other examples of the thirteenth embodiments, the at least one filter is integrally attached to the fluid circuit. In other examples of the thirteenth embodiments, the flowing water and concentrate through at least one sterilizing filter includes flowing water and concentrate through separate filters.

According to fourteenth embodiments, the disclosed subject matter includes a fluid circuit for peritoneal dialysis and dialysis solution preparation. A disposable mixing container of polymeric material has a pre-connected fluid circuit. The mixing container and fluid circuit are sealed from an external environment. A concentrate container of polymeric material is pre-connected to the fluid circuit. The concentrate container is sealed from an external environment. The fluid circuit includes a fluid flow director that includes a valve network that has junctions and valve portions that mechanically engage valve actuators to define selectable flow paths in the valve network. The valve network further includes a concentrate line connected to the concentrate container, a water line terminated by a water line connector, and a pair of lines connected to the mixing container to permit simultaneous flow into, and flow out from, the mixing container. A fluid line has an in-line sterilizing filter. The valve network is positioned and held in a cartridge that has a pumping portion supported by a rigid manifold. The manifold is hollow and defines at least some of the junctions. The manifold is rigid and defining two separate chambers connected by a pumping tube segment.

In other examples of the fourteenth embodiments, the in-line sterilizing filter has an air-line attached thereto; the air-line is connected such that air forced through the air-line applies pressure to a membrane of the in-line sterilizing filter to permit an integrity test thereof, said air-line also connecting to a port fixedly attached to the manifold. In other examples of the fourteenth embodiments, the air-line is collinear with at least a portion of a respective one of the concentrate and water lines. In other examples of the fourteenth embodiments, the valve network is supported by a panel and the manifold is connected to the panel. In other examples of the fourteenth embodiments, the valve network is supported by a panel and the manifold is spaced apart from the panel. In other examples of the fourteenth embodiments, the air-line is integral with at least a portion of a respective one of the concentrate and water lines.

In other examples of the fourteenth embodiments, the manifold chamber has pressure sensors integrated therein, one at each end of the pumping tube segment. In other examples of the fourteenth embodiments, the pumping tube segment is straight. In other examples of the fourteenth embodiments, the pressure sensor includes a pressure pod with a diaphragm that serves as a portion of a wall of a respective one of the two separate chambers. In other examples of the fourteenth embodiments, the respective concentrate line connectors are connected by a frame that supports a portion of the concentrate line. In other examples of the fourteenth embodiments, the frame has a window and the portion of the concentrate line passes across the window. In other examples of the fourteenth embodiments, the valve network has a drain line. In other examples of the fourteenth embodiments, the valve network has a fill/drain line connectable to a peritoneal catheter. In other examples of the fourteenth embodiments, the fill/drain line is sealed by a removable end cap. In other examples of the fourteenth embodiments, the fill/drain line has a second air-line collinear with the fill/drain line, connected at an end of the fill/drain line to a pressure pod connected to the fill/drain line to measure a pressure therewithin. In other examples of the fourteenth embodiments, the drain and water lines are connected by a frame that supports portions of the drain and water lines. In other examples of the fourteenth embodiments, the frame has a window and portions of the drain and water lines pass across the window. In other examples of the fourteenth embodiments, the valve portions are supported by a planar element. In other examples of the fourteenth embodiments, the planar element includes a pair of sheets shaped to hold the valve portions in predefined positions. In other examples of the fourteenth embodiments, the planar element includes a pair of sheets shaped to hold the valve portions in predefined positions, and at least one of the pair of sheets has holes in it to permit valve actuators to contact the valve portions. In other examples of the fourteenth embodiments, the valve portions are tube segments. In other examples of the fourteenth embodiments, the concentrate line has a valve portion exposed for access by a valve actuator. In other examples of the fourteenth embodiments, the cartridge includes parallel panels with the valve network sandwiched between them, and the valve portion held in the cartridge is aligned with a window in at least one of the panels to permit an actuator to access the valve portion. In other examples of the fourteenth embodiments, the cartridge includes a single folded panel forming parallel panel portions with the valve network sandwiched between them, and the valve portion held in the cartridge is aligned with a windows in at least one of the panels to permit an actuator to access the valve portion. Other examples of the fourteenth embodiments include a second sterilizing filter connected in series with the in-line sterilizing filter such that the second and in-line sterilizing filters are separated by a flow channel to prevent grow-through contamination between membranes thereof. In other examples of the fourteenth embodiments, the mixing container and concentrate container are defined by two bonded flexible panels along seams that define the mixing container and concentrate container. In other examples of the fourteenth embodiments, the seams are a result of thermal welding. In other examples of the fourteenth embodiments, the fluid circuit encloses a sterile internal volume.

According to fifteenth embodiments, the disclosed subject matter includes a system for performing a peritoneal dialysis treatment. At least two concentrate containers have concentrate supply connectors. The concentrate containers have sufficient concentrate to perform multiple peritoneal dialysis treatments, where each peritoneal dialysis treatment includes multiple fill/drain cycles. A daily disposable component includes a disposable mixing container of polymeric material with a pre-connected fluid circuit. The mixing container and fluid circuit are sealed from an external environment. The fluid circuit includes a fluid flow director that includes a valve network that has junctions and valve portions that mechanically engage valve actuators to define selectable flow paths in the valve network. The valve network further includes a fluid inlet line and a pair of lines connected to the mixing container to permit simultaneous flow into, and flow out from, the mixing container. The fluid inlet line has an in-line sterilizing filter with an air-line attached to the in-line sterilizing filter. The air-line is connected such that air forced through the air-line applies pressure to a membrane of the in-line sterilizing filter to permit an integrity test thereof. The valve network is positioned and held in a cartridge that has a pumping portion supported by a rigid manifold, a manifold that is hollow and defines at least some of the junctions, and air-lines connecting to ports fixedly attached to the manifold. The manifold chamber is rigid and defines two separate chambers connected by a pumping tube segment.

Other examples of the fifteenth embodiments include a connection platform that mechanically supports the at least two concentrate containers and selectively couples them to the fluid inlet line.

Other examples of the fifteenth embodiments include a connection platform with a water source and attachments for the at least two concentrate containers, the connection platform having a valve network that fluidly couples the concentrate containers and the water source to the fluid inlet line.

In other examples of the fifteenth embodiments, an air-line is collinear with at least a portion of the fluid inlet line. In other examples of the fifteenth embodiments, an air-line is attached along at least a portion of the fluid inlet line. In other examples of the fifteenth embodiments, the manifold chamber has pressure sensors integrated therein, one at each end of the pumping tube segment. In other examples of the fifteenth embodiments, the pumping tube segment is straight. In other examples of the fifteenth embodiments, the pressure sensor includes a pressure pod with a diaphragm that serves as a portion of a wall of a respective one of the two separate chambers. In other examples of the fifteenth embodiments, the respective concentrate line connectors are connected by a frame that supports portions of the concentrate lines. In other examples of the fifteenth embodiments, the frame has a window and portions of the concentrate lines pass across the window. In other examples of the fifteenth embodiments, the valve network has a drain line. In other examples of the fifteenth embodiments, the drain and fluid lines are connected by a frame that supports portions of the drain and fluid lines. In other examples of the fifteenth embodiments, the frame has a window and portions of the drain and fluid lines pass across the window. In other examples of the fifteenth embodiments, the valve portions are supported by a planar element. In other examples of the fifteenth embodiments, the planar element includes a pair of sheets shaped to hold the valve portions in predefined positions. In other examples of the fifteenth embodiments, the planar element includes a pair of sheets shaped to hold the valve portions in predefined positions, and at least one of the pair of sheets has holes in it to permit valve actuators to contact the valve portions. In other examples of the fifteenth embodiments, the valve portions are tube segments. In other examples of the fifteenth embodiments, the fluid circuit has a drain line with a drain connector, the fluid line has a fluid line connector, and the connection platform includes a fluid supply connector and a drain receiving connector to which the fluid line connector and the drain connector are respectively connectable. In other examples of the fifteenth embodiments, the at least two concentrate containers are contained in a single package. In other examples of the fifteenth embodiments, the single package is housed by a single box. In other examples of the fifteenth embodiments, the single box is made from cardboard. In other examples of the fifteenth embodiments, the at least two concentrate containers are cylindrical containers.

According to sixteenth embodiments, the disclosed subject matter includes a system for the preparation of sterile peritoneal dialysis fluid. It includes a disposable fluid circuit with a pumping tube segment and multiple valve segments. The peritoneal dialysis solution admixer/cycler dialysis treatment device includes at least one pumping actuator shaped to engage the at least one pumping tube segment, and has multiple valve actuators positioned to engage the valve segments. A first of the multiple valve segments is connected to a fluid inlet. The disposable fluid circuit has a sterilizing filter connected between the first of the multiple valve segments and the fluid inlet. The system has a water source such as a water purifier or containers of pure water. The system has a first concentrate container with sufficient concentrate for the preparation of enough peritoneal dialysis solution to perform multiple peritoneal dialysis treatments, each peritoneal dialysis treatment including multiple fill/drain cycles. A flow control module connects the first concentrate container and the water source to the fluid inlet and controls flow such that a selected one of water and concentrate can be pumped through the fluid inlet while excluding an unselected one of concentrate and water. The disposable fluid circuit has an integrally-attached mixing container sized to hold sufficient peritoneal dialysis solution for at least a single fill/drain cycle. The peritoneal dialysis solution admixer/cycler dialysis treatment device has a programmable controller programmed to control the pumping actuator to pump concentrate and water into the mixing container to make a batch of peritoneal dialysis fluid and subsequently to perform a fill/drain cycle that includes draining spent peritoneal dialysis solution and pumping a fill of the peritoneal dialysis solution from the mixing container.

Other examples of the sixteenth embodiments may include a second concentrate container that is connected by the flow control module to the fluid circuit.

Other examples of the sixteenth embodiments may include a second concentrate container that has concentrate for the preparation of enough peritoneal dialysis solution to perform multiple peritoneal dialysis treatments, each such peritoneal dialysis treatment including multiple fill/drain cycles.

In other examples of the sixteenth embodiments, the flow control module has a primary connector for the first concentrate container to be used every multiple peritoneal dialysis treatments and a secondary connector to which the fluid inlet is connected once every peritoneal dialysis treatment. In other examples of the sixteenth embodiments, the sterilizing filter has an air port to allow a membrane of the sterilizing filter to be pressure tested, and the controller is programmed to test the sterilizing filter membrane by applying pressure to the air port and measuring the pressure after pumping water therethrough. In other examples of the sixteenth embodiments, the controller generates an alarm signal responsively to a result of a test of the sterilizing filter membrane if the test indicates a loss of integrity of the sterilizing filter membrane.

According to seventeenth embodiments, the disclosed subject matter includes a system for the preparation of sterile peritoneal dialysis fluid. It includes a disposable fluid circuit with a pumping tube segment and multiple valve segments. The peritoneal dialysis solution admixer/cycler dialysis treatment device has at least one pumping actuator positioned to engage the at least one pumping tube segment, and multiple valve actuators positioned to engage the valve segments. A first of the multiple valve segments is connected to a fluid inlet. The disposable fluid circuit has a sterilizing filter connected between a fluid inlet connector and the first of the multiple valve segments. A first concentrate container has sufficient concentrate for the preparation of enough peritoneal dialysis solution to perform multiple peritoneal dialysis treatments, each peritoneal dialysis treatment including multiple fill/drain cycles. The disposable fluid circuit has an integrally-attached mixing container sized to hold sufficient peritoneal dialysis solution for at least a single fill/drain cycle. An interconnection module has a primary concentrate connector and a primary water connector. The first concentrate container is replaced by connecting a new first concentrate connector to the primary concentrate connector once every multiple peritoneal dialysis treatments. The interconnection module also has a common secondary connector to which the disposable fluid circuit fluid inlet connector is connected once every peritoneal dialysis treatment. The interconnection module has a valve network controlled by the programmable controller that selects water or concentrate to be drawn by the peritoneal dialysis solution admixer/cycler dialysis treatment device through the common secondary connector. The peritoneal dialysis solution admixer/cycler dialysis treatment device has a programmable controller programmed to control the pumping actuator to pump concentrate and water into the mixing container to make a batch of peritoneal dialysis fluid and subsequently to perform a fill/drain cycle that includes draining spent peritoneal dialysis solution and pumping a fill of the peritoneal dialysis solution from the mixing container.

Other examples of the seventeenth embodiments include a second concentrate container that is replaced by connecting a new second concentrate connector to the primary concentrate connector once every multiple peritoneal dialysis treatments, the interconnection module valve network controlled to select water, the first concentrate, or the second concentrate to be drawn by the peritoneal dialysis solution admixer/cycler dialysis treatment device through the common secondary connector. In other examples of the seventeenth embodiments, the second concentrate container has concentrate for the preparation of enough peritoneal dialysis solution to perform multiple peritoneal dialysis treatments, each peritoneal dialysis treatment including multiple fill/drain cycles, wherein first and second concentrate inlets are connected to the first and second concentrate containers by a double connector, the double connector making connections for the first concentrate inlet connector and the second concentrate inlet simultaneously to the first and second concentrate containers, the interconnection module selectively connecting the first and second concentrate inlets to the primary concentrate connector. In other examples of the seventeenth embodiments, the programmable controller is programmed to calculate and store data representing a volume, and data representing a composition of fluid remaining in a portion of the valve network after flowing fluid by the peritoneal dialysis solution admixer/cycler dialysis treatment device, and to control the pump responsively to the data representing a volume of water or concentrate, whereby the proportions of solutes and water ultimately generated in the mixing container includes residual volumes remaining at times in the fluid circuit which are accounted for by the controller.

According to eighteenth embodiments, the disclosed subject matter includes a method of performing a peritoneal dialysis treatment. The method includes drawing a concentrate and water through a sterilizing filter in predefined quantities to make a sufficient quantity of peritoneal dialysis solution for at least a single fill of a peritoneal dialysis treatment. The drawing includes, using an interconnection module, connecting water and concentrate at different times to a common inlet of a disposable fluid circuit to which the sterilizing filter is integrally attached. The method includes testing the sterilizing filter by means of an air pressure test and using, or preventing use of, the quantity of peritoneal dialysis solution for a peritoneal dialysis fill and drain cycle depending on a result of the testing.

In other eighteenth embodiments, the method may include connecting a long-term concentrate container to the interconnection module once every multiple peritoneal dialysis treatments. In other eighteenth embodiments, the method may include connecting a peritoneal dialysis treatment circuit with the sterilizing filter integrally attached thereto to the interconnection module once every single peritoneal dialysis treatments. In other eighteenth embodiments, the method may include mixing the water and the concentrate. In other eighteenth embodiments, the drawing and the mixing are performed using a single common pump. In other eighteenth embodiments, the drawing is assisted by a separate pump connected to a source of concentrate.

According to nineteenth embodiments, the disclosed subject matter includes a method of making a fluid circuit that has a chamber prefilled with medicament concentrate. The method includes integrally connecting a fluid circuit with a chamber, and connecting a sterilizing filter with the chamber. The integrally connecting and connecting a sterilizing filter may form an assembly with a sealed volume that is separated from the outside environment by walls thereof, a frangible plug in a concentrate outlet line stemming from the chamber, and a membrane of the sterilizing filter. The method includes sterilizing the assembly and sterile-filling the chamber with concentrate through the sterilizing filter, permanently cutting and sealing a line connecting the sterilizing filter and the chamber. The method may include subjecting the fluid circuit and chamber to gamma or e-beam sterilization.

According to twentieth embodiments, the disclosed subject matter includes a fluid circuit for peritoneal dialysis and dialysis solution preparation. A disposable mixing container of polymeric material has a pre-connected fluid circuit. The mixing container and fluid circuit are sealed from an external environment. A concentrate container of polymeric material is pre-connected to the fluid circuit. The concentrate container is sealed from an external environment. The fluid circuit includes a fluid flow director that includes a valve network that has junctions and valve portions that mechanically engage valve actuators to define selectable flow paths in the valve network. The valve network further includes a concentrate line connected to the concentrate container. A water line is terminated by a water line connector. A pair of lines is connected to the mixing container to permit simultaneous flow into, and flow out from, the mixing container. The water line has an in-line sterilizing filter with an air-line attached thereto. The air-line is connected such that air forced through the air-line applies pressure to a membrane of the in-line sterilizing filter to permit an integrity test thereof. The valve network is positioned and held in a cartridge that has a pumping portion supported by a rigid manifold which is hollow and defines at least some of the junctions, and an air-line connecting to a port fixedly attached to the manifold. The manifold is rigid and defines two separate chambers connected by a pumping tube segment.

In variations thereof, the twentieth embodiments include ones in which the air-line is collinear with at least a portion of a respective one of the concentrate and water lines. In variations thereof, the twentieth embodiments include ones in which the valve network is supported by a panel and the manifold is connected to the panel. In variations thereof, the twentieth embodiments include ones in which the valve network is supported by a panel and the manifold is spaced apart from the panel. In variations thereof, the twentieth embodiments include ones in which the air-line is integral with at least a portion of a respective one of the concentrate and water lines. In variations thereof, the twentieth embodiments include ones in which the manifold chamber has pressure sensors integrated therein, one at each end of the pumping tube segment.

In variations thereof, the twentieth embodiments include ones in which the pumping tube segment is straight. In variations thereof, the twentieth embodiments include ones in which the pressure sensor includes a pressure pod with a diaphragm that serves as a portion of a wall of a respective one of the two separate chambers. In variations thereof, the twentieth embodiments include ones in which the respective concentrate line connectors are connected by a frame that supports a portion of the concentrate line. In variations thereof, the twentieth embodiments include ones in which the frame has a window and a portion of the concentrate line passes across the window. In variations thereof, the twentieth embodiments include ones in which the valve network has a drain line. In variations thereof, the twentieth embodiments include ones in which the valve network has a fill/drain line connectable to a peritoneal catheter. In variations thereof, the twentieth embodiments include ones in which the fill/drain line is sealed by a removable end cap. In variations thereof, the twentieth embodiments include ones in which the fill/drain line has a second air-line collinear with the fill/drain line, connected at an end of the fill/drain line to a pressure pod connected to the fill/drain line to measure a pressure therewithin.

In variations thereof, the twentieth embodiments include ones in which the drain and water lines are connected by a frame that supports portions of the drain and water lines. In variations thereof, the twentieth embodiments include ones in which the frame has a window and portions of the drain and water lines pass across the window. In variations thereof, the twentieth embodiments include ones in which the valve portions are supported by a planar element. In variations thereof, the twentieth embodiments include ones in which the planar element includes a pair of sheets shaped to hold the valve portions in predefined positions. In variations thereof, the twentieth embodiments include ones in which the planar element includes a pair of sheets shaped to hold the valve portions in predefined positions, and at least one of the pair of sheets has holes in it to permit valve actuators to contact the valve portions. In variations thereof, the twentieth embodiments include ones in which the valve portions are tube segments. In variations thereof, the twentieth embodiments include ones in which the concentrate line is sealed by a frangible seal. In variations thereof, the twentieth embodiments include ones in which the cartridge includes parallel panels with the valve network sandwiched between them, and the frangible seal held in the cartridge is aligned with windows in at least one of the panels to permit an actuator to fracture them prior to use, thereby allowing the concentrate to flow through the concentrate line. In variations thereof, the twentieth embodiments include ones in which the cartridge includes a single folded panel forming parallel panel portions with the valve network sandwiched between them, and the frangible seal held in the cartridge is aligned with windows in at least one of the panels to permit an actuator to fracture them prior to use thereby allowing the concentrate to flow through the concentrate line. In variations thereof, the twentieth embodiments include ones in which the valve network includes the concentrate line which is sealed by a frangible seal thereby separating the concentrate from the rest of the fluid circuit until the frangible seal is fractured. In variations thereof, the twentieth embodiments include ones with a second sterilizing filter connected in series with the in-line sterilizing filter such that the second and in-line sterilizing filters are separated by a flow channel to prevent grow-through contamination between membranes thereof. In variations thereof, the twentieth embodiments include ones in which the mixing container and concentrate container are defined by two bonded flexible panels along seams that define the mixing container and concentrate container. In variations thereof, the twentieth embodiments include ones in which the seams are a result of thermal welding. In variations thereof, the twentieth embodiments include ones in which the fluid circuit encloses a sterile internal volume.

According to twenty-first embodiments, the disclosed subject matter includes a fluid line connector. At least one thermoplastic tube is supported in a frame such that the at least one thermoplastic tube is accessible from opposite sides of the frame. The frame has an overhanging ridge at one end and at least one connector that is fluidly coupled at an opposite end to the at least one thermoplastic tube. A cap is fitted to the frame to cover the at least one connector. The at least one tube extends through holes in the frame at ends thereof adjacent the overhanging ridge.

In variations thereof, the twenty-first embodiments include ones in which the frame has a recess shaped to engage a détente pin along an elongated side thereof. In variations thereof, the twenty-first embodiments include ones in which the frame has an oval-shaped recess, and the at least one connector is located within the oval-shaped recess. In variations thereof, the twenty-first embodiments include ones in which the cap fits in the oval-shaped recess to define a tortuous path between the at least one connector and an access of the oval-shaped recess. In variations thereof, the twenty-first embodiments include ones in which at least one connector and the at least one thermoplastic tubes are at least two.

According to twenty-second embodiments, the disclosed subject matter includes a connector system in which a connector component has at least one thermoplastic tube supported in a frame such that the at least one thermoplastic tube is accessible from opposite sides of the frame. The frame has an overhanging ridge at one end and at least one connector that is fluidly coupled at an opposite end to the at least one thermoplastic tube. A cap is fitted to the frame to cover the at least one connector. The at least one tube extends through holes in the frame at an end thereof adjacent the overhanging ridge. A fluid supply device has at least one supply connector that mates with the at least one connector. The fluid supply device has a portion shaped to engage the frame to align the at least one thermoplastic tube with a tube cut-and-seal device.

In variations thereof, the twenty-second embodiments include ones in which the cut-and-seal device cuts the at least one thermoplastic tube thereby forming two cut ends and seals it at the two cut ends. The connector component is configured to permit the at least one thermoplastic tube to be withdrawn from the one end leaving the frame and at least one connector in place on the at least one supply connector to cover and protect it from contamination until it is replaced by another connector component. In variations thereof, the twenty-second embodiments include ones in which the frame has a recess shaped to engage a détente pin along an elongated side thereof. In variations thereof, the twenty-second embodiments include ones in which the frame has an oval-shaped recess, and the at least one connector is located within the oval-shaped recess. In variations thereof, the twenty-second embodiments include ones in which the cap fits in the oval-shaped recess to define a tortuous path between the at least one connector and an access of the oval-shaped recess.

According to twenty-third embodiments, the disclosed subject matter includes a fluid preparation method implemented by an admixer under programmatic control of a controller. The controller implements the method. The admixer has, connected thereto, a fluid circuit that includes a mixing container, one or more containers of medicament concentrate, and a source of purified water suitable for peritoneal dialysate. Each of the one or more containers has sufficient medicament concentrate for multiple treatments. The admixer has actuators that engage with the fluid circuit to transport concentrate and water to the mixing container. The method includes flowing purified water and concentrate through the fluid circuit to the mixing container to prepare a medicament in the mixing container by admixing and diluting the medicament concentrate. The flowing includes flowing water and concentrate through at least one sterilizing filter to ensure sterility of the water and concentrate.

In variations thereof, the twenty-third embodiments include ones in which the at least one sterilizing filter is integrally attached to the fluid circuit. In variations thereof, the twenty-third embodiments include ones that include ensuring an integrity of at least one sterilizing filter by testing the at least one sterilizing filter or providing serially-connected redundant sterilizing filters. In variations thereof, the twenty-third embodiments include ones that include using the contents of the mixing container to treat a first patient and thereafter replacing the fluid circuit in preparation for treating the first or a second patient.

According to twenty-fourth embodiments, the disclosed subject matter includes a fluid preparation system. An admixing component receives water and concentrate from sources thereof and mixes them in a mixing container under control of a controller. A drain component is connected to the mixing container through a fluid flow director controlled by the controller to selectively convey fluids from the mixing container to the drain through a fluid channel containing a fluid conductivity measurement sensor. A bypass line has an automatic valve, controlled by the controller, that diverts fluids from fluid flow director directly to the drain without flowing through the fluid conductivity measurement sensor.

In variations thereof, the twenty-fourth embodiments include ones in which the controller is a programmable controller programmed to divert fluids from a source other than the mixing container from the fluid flow director directly to the drain. In variations thereof, the twenty-fourth embodiments include ones in which the source other than the mixing container is a source of cleaning fluid or a source of water. In variations thereof, the twenty-fourth embodiments include ones in which the source other than the mixing container is a source of used dialysate. In variations thereof, the twenty-fourth embodiments include ones in which the source other than the mixing container is a source of cleaning fluid or a source of water.

According to twenty-fifth embodiments, the disclosed subject matter includes a system for generating a dialysis fluid. A fluid admixer with an admixer controller and valve and pumping actuators is controlled by an admixer controller. At least two concentrate containers have concentrate supply connectors. The concentrate containers have sufficient concentrate to perform multiple peritoneal dialysis treatments. Each treatment includes multiple fill/drain cycles. A daily disposable component includes a mixing container of polymeric material with a pre-connected fluid circuit. The mixing container and fluid circuit is sealed from an external environment. The mixing container has a capacity sufficient for a full automated peritoneal dialysis treatment of at least five fill/drain cycles each of at least 1000 ml. The fluid circuit includes a valve network with junctions and valve portions and a pumping portion that mechanically interface with the valve and pumping actuators to define selectable flow paths in the valve network. The valve network further includes a fluid inlet line. The valve network is fluidly connected for flow into and out of the mixing container. The fluid inlet line has at least one in-line sterilizing filter.

In variations thereof, the twenty-fifth embodiments include ones in which the valve network is positioned and held in a cartridge that has a pumping portion supported by a rigid manifold, the rigid manifold is hollow and defining at least some of the junctions. In variations thereof, the twenty-fifth embodiments include ones in which the at least one in-line sterilizing filter includes a testable filter with an air-line, the air-line connecting to a port fixedly attached to the rigid manifold and configured to engage with an air supply port of the fluid admixer upon insertion of the manifold in a slot of the fluid admixer. In variations thereof, the twenty-fifth embodiments include ones in which the rigid manifold defines two separate chambers, the pumping portion includes a pumping tube segment, the pumping tube segment connecting the two separate chambers. In variations thereof, the twenty-fifth embodiments include ones that include a connection platform that mechanically supports the at least two concentrate containers and selectively couples them to the fluid inlet line. In variations thereof, the twenty-fifth embodiments include ones that include a connection platform with a water source and attachments for the at least two concentrate containers, the connection platform has a valve network that fluidly couples the concentrate containers and the water source to the fluid inlet line. In variations thereof, the twenty-fifth embodiments include ones in which the at least one sterilizing filter includes two redundant sterilizing filters in series or an air-line attached to the in-line sterilizing filter, the air-line is connected such that air forced through the air-line applies pressure to a membrane of the in-line sterilizing filter to permit an integrity test thereof the air-lines are each collinear with at least a portion of the fluid inlet line. In variations thereof, the twenty-fifth embodiments include ones in which the air-line is attached along at least a portion of the fluid inlet line. In variations thereof, the twenty-fifth embodiments include ones in which each manifold chamber has pressure sensors integrated therein, one at each end of the pumping tube segment. In variations thereof, the twenty-fifth embodiments include ones in which the pumping tube segment is straight. In variations thereof, the twenty-fifth embodiments include ones in which the pressure sensors include pressure pods, each with a diaphragm that serves as a portion of a wall of a respective one of the two separate chambers. In variations thereof, the twenty-fifth embodiments include ones that include a connection platform, wherein respective concentrate supply connectors are connected to a valve network of the connection platform, the connection platform has a water source connected to the fluid inlet by the connection platform valve network. In variations thereof, the twenty-fifth embodiments include ones in which the valve network has a drain line with at least one conductivity sensor. In variations thereof, the twenty-fifth embodiments include ones that include a connection platform and wherein respective concentrate supply connectors are connected to a valve network of the connection platform, the connection platform has a water source connected to the fluid inlet by the connection platform valve network, the water source has a pump and the connection platform valve network has a pump connected by outlets of the at least two concentrate containers.

According to twenty-sixth embodiments, the disclosed subject matter includes a fluid preparation system with an admixer under programmatic control of an admixing controller. The admixer has connectable to a disposable fluid circuit that includes a mixing container. The fluid circuit is connected by a fluid interface to one or more containers of medicament concentrate, and a pure water source, the pure water source includes a container or treatment plant suitable for providing purified water suitable for peritoneal dialysate. Each of the one or more containers of medicament concentrate has sufficient medicament concentrate for multiple peritoneal dialysis treatments. the admixer is connected to the fluid interface to receive medicament concentrate and water from the pure water source therethrough. the admixer has actuators that engage with the fluid circuit, when connected thereto, to transport concentrate and water to the mixing container. The admixing controller is programmed to flow water and concentrate through the fluid circuit to the mixing container to prepare a medicament in the mixing container by admixing and diluting the medicament concentrate.

In variations thereof, the twenty-sixth embodiments include ones with at least one sterilizing filter positioned in the disposable fluid circuit to filter water and concentrate from the one or more containers of concentrate, wherein the at least one sterilizing filter is integrally attached to the fluid circuit. In variations thereof, the twenty-sixth embodiments include ones in which the fluid interface has a drain component connectable to the fluid circuit by a drain port. In variations thereof, the twenty-sixth embodiments include ones in which the drain component has a conductivity sensor and two selectable channels including a bypass channel that connects the drain port directly to a drain outlet and a conductivity sensor channel connects the drain port to the drain outlet through the conductivity sensor, a selected one of the two selectable channels connecting the drain port and drain outlet being selectable by means of a control valve. In variations thereof, the twenty-sixth embodiments include ones in which the admixing controller selects the selected one of the two selectable channels responsively to a type of fluid or a fluid source. In variations thereof, the twenty-sixth embodiments include ones in which the admixing controller selects the conductivity sensor channel, at times, when the fluid source is the mixing container. In variations thereof, the twenty-sixth embodiments include ones in which the admixing controller selects the bypass channel, at times, when the fluid source is a source of cleaning fluid. In variations thereof, the twenty-sixth embodiments include ones in which the admixing controller selects the bypass channel, at times, when the fluid source is the pure water source. In variations thereof, the twenty-sixth embodiments include ones in which the admixing controller selects the bypass channel, at times, when the fluid source is a source of used dialysate. In variations thereof, the twenty-sixth embodiments include ones in which the fluid interface has a fluid supply network with valves for each of the one or more containers of medicament concentrate, the fluid supply network selectively connecting a selected one of the one or more containers of medicament concentrate to a common concentrate line of the fluid supply network responsively to the admixing controller. In variations thereof, the twenty-sixth embodiments include ones in which the fluid supply network includes a single pump in the common concentrate line. In variations thereof, the twenty-sixth embodiments include ones in which the common concentrate line is connectable to a common fluid inlet of the fluid circuit. In variations thereof, the twenty-sixth embodiments include ones in which the common fluid inlet of the fluid circuit has a sterilizing filter. In variations thereof, the twenty-sixth embodiments include ones in which the at least one sterilizing filter includes two sterilizing filters in series or a testable filter with a port for an application of pressurized air. In variations thereof, the twenty-sixth embodiments include ones in which the fluid interface has a fluid supply network with valves for each of the one or more containers of medicament concentrate and a valve for the pure water source, the fluid supply network selectively connecting a selected one of the one or more containers of medicament concentrate or the pure water source a common fluid line of the fluid supply network responsively to the admixing controller. In variations thereof, the twenty-sixth embodiments include ones in which the fluid supply network includes a single pump in the common fluid line. In variations thereof, the twenty-sixth embodiments include ones in which the common fluid line is connectable to a common fluid inlet of the fluid circuit. In variations thereof, the twenty-sixth embodiments include ones in which the common fluid inlet of the fluid circuit has a sterilizing filter. In variations thereof, the twenty-sixth embodiments include ones that include at least one in-line sterilizing filter positioned in the disposable fluid circuit to filter water and concentrate from the one or more containers of concentrate, wherein the at least one sterilizing filter is integrally attached to the fluid circuit and wherein the sterilizing filter includes two sterilizing filters in series or a testable filter with a port for an application of pressurized air. In variations thereof, the twenty-sixth embodiments include ones in which the fluid interface has a fluid supply network with valves for each of the one or more containers of medicament concentrate and a valve for the pure water source, the fluid supply network selectively connecting a selected one of the one or more containers of medicament concentrate or the pure water source a common fluid line of the fluid supply network responsively to the admixing controller, wherein the pure water source includes a treatment plant with a pump. In variations thereof, the twenty-sixth embodiments include ones in which the fluid supply network includes a single pump in the common fluid line. In variations thereof, the twenty-sixth embodiments include ones in which the common fluid line is connectable to a common fluid inlet of the fluid circuit. In variations thereof, the twenty-sixth embodiments include ones in which the common fluid inlet of the fluid circuit has a sterilizing filter. In variations thereof, the twenty-sixth embodiments include ones in which the sterilizing filter includes two sterilizing filters in series or a testable filter with a port for an application of pressurized air. In variations thereof, the twenty-sixth embodiments include ones in which the fluid interface has a fluid supply network with channels for each of the one or more containers of medicament concentrate and a channel for the pure water source, each of the channels connecting to the fluid circuit connected to the admixing controller, the admixing controller selecting, at a time, one of the channels for transport of a selected concentrate or water to the mixing container by actuation of the actuators. In variations thereof, the twenty-sixth embodiments include ones in which each of the channels has a sterilizing filter. In variations thereof, the twenty-sixth embodiments include ones in which the sterilizing filter includes two sterilizing filters in series or a testable filter with a port for application of pressurized air.

According to twenty-seventh embodiments, the disclosed subject matter includes a fluid circuit for dialysis solution preparation. A disposable mixing container of polymeric material has a pre-connected fluid circuit, the mixing container and fluid circuit is sealed from an external environment. A concentrate container of polymeric material is pre-connected to the fluid circuit and fluidly coupled therewith except for has a frangible seal between the concentrate container and a rest of the fluid circuit. The concentrate container and fluid circuit are sealed from an external environment. The fluid circuit includes a valve network that has junctions and valve portions that mechanically interface with valve actuators to define selectable flow paths in the valve network. The valve network further includes a concentrate line connected to the concentrate container, a water line terminated by a water line connector, and at least one line connected to the mixing container to permit simultaneous flow into, and flow out from, the mixing container. A water inlet line in the valve network fluidly coupled to the mixing container, the water inlet line having an in-line sterilizing filter. In the twenty-seventh embodiments and in others disclosed herein, the sterile filter is positioned in the water line. In use, because of the pumping directions and valve settings, the water line may be the only line by which fluid may enter the mixing container via the fluid network from the outside world. This is not guaranteed by the form of the fluid circuit but this is enabled by it in providing the sterilizing filter on the water connection. Other connection such as the patient line, drain, and sample lines may be provided but these only permit flow out of the fluid circuit, except for the flow of spent peritoneal dialysis fluid which is generally safe from contamination as long as the patient is healthy and sterile practice is properly followed in performing a treatment. An example of the twenty-seventh embodiment is the fluid circuit 200. It can be verified that the only other fluids required for adding to the mixing container to make a batch of dialysis fluid are the concentrates and those are already sterile-sealed in the fluid circuit. Thus, by providing a sterile filter 115 on the water line, no risk of touch contamination is present except for the patient line, when the admixer/cycler uses the fluid circuit.

In variations thereof, the twenty-seventh embodiments include ones in which the at least one line includes a pair of lines. In variations thereof, the twenty-seventh embodiments include ones in which the valve network is positioned and held in a cartridge that has a pumping portion. In variations thereof, the twenty-seventh embodiments include ones in which the valve network is positioned and held in a cartridge that has a pumping portion supported by a rigid manifold. In variations thereof, the twenty-seventh embodiments include ones in which the manifold has two chambers interconnected by the pumping portion. In variations thereof, the twenty-seventh embodiments include ones in which the manifold two chambers are rigidly connected. In variations thereof, the twenty-seventh embodiments include ones in which the pumping portion includes a pumping tube segment. In variations thereof, the twenty-seventh embodiments include ones in which the valve network includes a manifold and the in-line sterilizing filter has an air-line attached thereto, the air-line is connected such that air forced through the air-line applies pressure to a membrane of the in-line sterilizing filter to permit an integrity test thereof, the air-line connecting to a port fixedly attached to the manifold. In variations thereof, the twenty-seventh embodiments include ones in which the mixing container and concentrate container are defined by two bonded flexible panels along seams to define the mixing container and concentrate container. In variations thereof, the twenty-seventh embodiments include ones in which the seams are integral as formed by welding or adhesive bonding. In variations thereof, the twenty-seventh embodiments include ones in which the fluid circuit encloses a sterile internal volume.

According to twenty-eight embodiments, the disclosed subject matter includes a system for dialysis solution preparation. An admixer has valve and pumping actuators and an admixing controller. A disposable mixing container of polymeric material has a pre-connected fluid circuit. The mixing container and fluid circuit are sealed from an external environment. A concentrate container of polymeric material is pre-connected to the fluid circuit and fluidly coupled therewith except for has a frangible seal between the concentrate container and a rest of the fluid circuit. The concentrate container and fluid circuit are sealed from an external environment (using connector seal caps as necessary). The fluid circuit includes a valve network that has pumping and valve portions that mechanically interface with the valve and pumping actuators to transport fluid along selected channels in the valve network. The valve network further includes a concentrate line connected to the concentrate container, a water line terminated by a water line connector, and at least one line connected to the mixing container to permit simultaneous flow into, and flow out from, the mixing container. A water inlet line in the valve network fluidly coupled to the mixing container, the water inlet line having an in-line sterilizing filter.

In variations thereof, the twenty-eighth embodiments include ones in which the admixer has a seal breaker that engages with the frangible seal, the admixing controller breaking the frangible seal before transporting concentrate through the fluid circuit. In variations thereof, the twenty-eighth embodiments include ones in which the at least one line includes a pair of lines. In variations thereof, the twenty-eighth embodiments include ones in which the valve network is positioned and held in a cartridge that has a pumping portion. In variations thereof, the twenty-eighth embodiments include ones in which valve network is positioned and held in a cartridge that has a pumping portion supported by a rigid manifold. In variations thereof, the twenty-eighth embodiments include ones in which the manifold has two chambers interconnected by the pumping portion. In variations thereof, the twenty-eighth embodiments include ones in which the manifold two chambers are rigidly connected. In variations thereof, the twenty-eighth embodiments include ones in which the pumping portion includes a pumping tube segment. In variations thereof, the twenty-eighth embodiments include ones in which the in-line sterilizing filter has an air-line attached thereto, the air-line is connected such that air forced through the air-line applies pressure to a membrane of the in-line sterilizing filter to permit an integrity test thereof, the air-line connecting to a port fixedly attached to the manifold. In variations thereof, the twenty-eighth embodiments include ones in which the mixing container and concentrate container are defined by two bonded flexible panels along seams to define the mixing container and concentrate container. In variations thereof, the twenty-eighth embodiments include ones in which the seams are integral as formed by welding or adhesive bonding. In variations thereof, the twenty-eighth embodiments include ones in which the system encloses a sterile internal volume.

According to twenty-ninth embodiments, the disclosed subject matter includes a system for dialysis solution preparation. An admixer has valve actuators, a pumping actuator, and an admixing controller. A disposable mixing container of polymeric material is pre-connected by a mixing container line to a fluid circuit. The mixing container and fluid circuit are sealed from an external environment and the fluid circuit has a valve network. One or more concentrate containers and a source of purified water are connected to the valve network. The valve network defines selectable flow paths to convey water and concentrate into the mixing container and permit flow of contents of the mixing container out of the mixing container. The valve network has pumping and valve portions that mechanically interface with the valve and pumping actuators to transport fluid along selected channels in the valve network to mix water and concentrate in the mixing container. The mixing container line is connected to a header tube with multiple openings to distribute flow over an extended length thereof to the mixing container. The admixing controller controls the pumping actuator pump to mix fluid in the mixing container by pumping fluid into and out of the mixing container.

In variations thereof, the twenty-ninth embodiments include ones in which a header tube receives flow from the mixing container at multiple locations along the header tube. In variations thereof, the twenty-ninth embodiments include ones in which the header tube has a plurality of openings distributed along a major length thereof. In variations thereof, the twenty-ninth embodiments include ones in which the mixing container line is used for incoming flow only and outgoing flow is conveyed from the mixing container through a further line connected to the valve network. In variations thereof, the twenty-ninth embodiments include ones in which the fluid circuit has an accumulator and the pumping actuator pumps fluid back and forth between the mixing container and the accumulator to mix the contents of the mixing container.

According to thirtieth embodiments, the disclosed subject matter includes a fluid circuit for dialysis solution preparation. A disposable mixing container of polymeric material is pre-connected by a mixing container line to a fluid circuit. The mixing container and fluid circuit are sealed from an external environment. The fluid circuit has a valve network. At least one fluid line has an inlet connection for receiving concentrate and purified water into the valve network. The valve network defining selectable flow paths to convey water and concentrate into the mixing container and permit flow of contents of the mixing container out of the mixing container. The valve network has pumping and valve portions that can mechanically interface with valve and pumping actuators to define the selectable flow paths in the valve network and permit pumping therethrough to mix water and concentrate in the mixing container. The mixing container line is connected to a header tube with multiple openings to distribute flow over an extended length thereof to the mixing container.

In variations thereof, the thirtieth embodiments include ones in which the mixing container header tube receives flow from the mixing container at multiple locations along the header tube. In variations thereof, the thirtieth embodiments include ones in which the fluid circuit includes an accumulator fluidly connected to the mixing container with the pumping portion between the mixing container and accumulator to permit the pumping of fluid therebetween to perform mixing.

In variations thereof, the thirtieth embodiments include ones in which the header tube has a plurality of openings distributed along a major length thereof. In variations thereof, the thirtieth embodiments include ones in which the mixing container line is used for incoming flow only and outgoing flow is conveyed from the mixing container through a further line connected to the valve network.

According to thirty-first embodiments, the disclosed subject matter includes a connector system with a connector component that has at least one thermoplastic tube supported in a frame such that the at least one thermoplastic tube is accessible from opposite sides of the frame. The frame has a first at least one male and/or female connector that is fluidly coupled at an end of the at least one thermoplastic tube. A complementary connector has a second at least one male and/or female connector that fits the first at least one male or female connector. A pin on one of the complementary connector or the frame is adjacent a respective one of the first and second male and/or female connector. There is a slot on the other of the complementary connector or the frame that is sized and positioned to receive the pin.

In variations thereof, the thirty-first embodiments include ones in which a cap that is fitted to the frame to cover the at least one connector. In variations thereof, the thirty-first embodiments include ones in which the at least one thermoplastic tube extends through one or more holes in the frame at an end thereof. In variations thereof, the thirty-first embodiments include ones in which the frame has an overhanging ridge adjacent the first at least one male and/or female connector. In variations thereof, the thirty-first embodiments include ones that include a fluid supply device with at least one supply connector that mates with the at least one connector, the fluid supply device has a portion shaped to engage the frame to align the at least one thermoplastic tube with a tube cut-and-seal device. In variations thereof, the thirty-first embodiments include ones in which the cut-and-seal device cuts the at least one thermoplastic tube thereby forming two cut ends and seals it at the two cut ends, the connector component is configured to permit the at least one thermoplastic tube to be withdrawn from the one end leaving the frame and at least one connector in place on the at least one supply connector to cover and protect it from contamination until it is replaced by another connector component. In variations thereof, the thirty-first embodiments include ones in which the frame has a recess shaped to engage a détente pin along an elongated side thereof. In variations thereof, the thirty-first embodiments include ones in which the frame has an oval-shaped recess, the at least one connector is located within the oval-shaped recess. In variations thereof, the thirty-first embodiments include ones in which the cap fits in the oval-shaped recess to define a tortuous path between the at least one connector and an access of the oval-shaped recess. In variations thereof, the thirty-first embodiments include ones in which at least one connector and the at least one thermoplastic tube are at least two. In variations thereof, the thirty-first embodiments include ones in which the frame has a recess shaped to engage a détente pin along an elongated side thereof. In variations thereof, the thirty-first embodiments include ones in which the frame has an oval-shaped recess, the at least one connector is located within the oval-shaped recess. In variations thereof, the thirty-first embodiments include ones in which the cap fits in the oval-shaped recess to define a tortuous path between the at least one connector and an access of the oval-shaped recess. In variations thereof, the thirty-first embodiments include ones in which the at least one connector and the at least one thermoplastic tube are at least two.

According to thirty-second embodiments, the disclosed subject mater includes a system for preparing dialysis treatment fluid. An integrally interconnected fluid circuit includes a mixing container with a pre-connected fluid circuit. The mixing container and fluid circuit are sealed from an external environment. The fluid circuit includes a valve network that has junctions and valve portions that mechanically interface with valve actuators to define selectable flow paths in the valve network. The valve network further includes a pumping portion and a fluid inlet line with a connector for connection to a fluid source. The fluid inlet line is fluidly connected to the mixing container by the pumping portion. The valve network is fluidly connects the mixing container to the fluid inlet. The fluid inlet line has at least one in-line sterilizing filter includes one of a pair of spaced sterilizing filters and a testable filter with an air-line.

In variations thereof, the thirty-second embodiments include ones in which the mixing container is principally of polymeric sheet material. In variations thereof, the thirty-second embodiments include ones in which the valve portions include tube segments that are flexible to permit closure by clamps. In variations thereof, the thirty-second embodiments include ones that include a manifold connected to the valve network and defining at least some of the junctions, the manifold has integrated pressure sensors. In variations thereof, the thirty-second embodiments include ones in which the manifold supports the pumping portion between the pressure sensors. In variations thereof, the thirty-second embodiments include ones in which the pumping portion is a straight tube supported at opposite ends thereof by the manifold. In variations thereof, the thirty-second embodiments include ones in which the manifold has connectors for the air-line.

In variations thereof, the thirty-second embodiments include ones in which the sterile filter is a testable sterile filter with an air pressure line, the air pressure line is connected to an air pump. In variations thereof, the thirty-second embodiments include ones in which the mixing container has two mixing container lines. In variations thereof, the thirty-second embodiments include ones in which the mixing container has single mixing container line. In variations thereof, the thirty-second embodiments include ones in which the valve network is connected to an accumulator that is connected by the pumping portion to the mixing container. In variations thereof, the thirty-second embodiments include ones in which the fluid inlet is connected to at least two concentrate containers, the concentrate containers have a capacity sufficient to store enough concentrate to perform multiple peritoneal dialysis treatments, where each treatment includes multiple fill/drain cycles. In variations thereof, the thirty-second embodiments include ones in which the fluid inlet is connected to a water source. In variations thereof, the thirty-second embodiments include ones in which a first of the at least two concentrate containers contains an osmotic agent and the second of the concentrate containers containing electrolytes. In variations thereof, the thirty-second embodiments include ones that include a peritoneal dialysis admixer/cycler with a controller connected to control valve actuators arranged to engage the valve portions and a pumping actuator arranged to receive the pumping portion when the fluid circuit is attached thereto. In variations thereof, the thirty-second embodiments include ones in which the controller is of a programmable type that stores a program to automatically perform a pressure test of the sterile filter filling the mixing container with a fluid. In variations thereof, the thirty-second embodiments include ones that include a peritoneal dialysis admixer/cycler with a controller connected to control valve actuators arranged to engage the valve portions and a pumping actuator arranged to receive the pumping portion when the fluid circuit is attached thereto, wherein the controller is of a programmable type that stores a program to automatically detect the replacement of the fluid circuit and responsively thereto, to determine whether a remaining quantity of the at least two concentrates is sufficient to mix sufficient peritoneal dialysis fluid for a treatment. In variations thereof, the thirty-second embodiments include ones that include a peritoneal dialysis admixer/cycler with a controller that controls a pumping actuator in engagement with the pumping portion, the controller controlling the pumping actuator to mix fluid in the mixing container by continuously circulating fluid with the pump through the valve network and the mixing container through the mixing container lines.

In variations thereof, the thirty-second embodiments include ones that include a peritoneal dialysis admixer/cycler with a controller that controls a pumping actuator in engagement with the pumping portion, the controller controlling the pumping actuator to mix fluid in the mixing container by intermittently exchanging fluid with the pump or an accumulator connected to the valve network. In variations thereof, the thirty-second embodiments include ones in which fluid circuit has a double connector carrying the fluid inlet line and a drain line, the drain line is connected to the valve network, the double connector has a frame that exposes the fluid inlet and drain lines on opposing sides thereof. In variations thereof, the thirty-second embodiments include ones in which the manifold has at least one manifold chamber connected to a sample port, the at least one sample port is controlled by one of the valve actuators responsively to the controller. In variations thereof, the thirty-second embodiments include ones that include a manifold connected to the valve network and defining at least some of the junctions, wherein the fluid circuit has a sample line, a patient fill line, a patient drain line, and drain line connected to the manifold. In variations thereof, the thirty-second embodiments include ones in which the two mixing container lines, the sample line, the fluid inlet line, the patient fill line, the patient drain line, stem from the manifold. In variations thereof, the thirty-second embodiments include ones in which the two mixing container lines, the sample line, the fluid inlet line, the patient fill line, the patient drain line are parallel and adjacent to the manifold and pass along a planar support. In variations thereof, the thirty-second embodiments include ones in which the planar support has windows to permit access to pinch valve actuators. In variations thereof, the thirty-second embodiments include ones in which the planar support, manifold and parallel lines form a generally planar cartridge that can be inserted in a slot. In variations thereof, the thirty-second embodiments include ones in which the controller performs a peritoneal dialysis treatment using the mixing container. In variations thereof, the thirty-second embodiments include ones in which the controller detects an attachment of a new fluid circuit. In variations thereof, the thirty-second embodiments include ones that include a peritoneal dialysis admixer/cycler with a controller that controls a pumping actuator and valve actuators in a receiver into which the insertion of the cartridge, when inserted therein, aligns the pumping actuator, pinch valve actuators, an air sensor, air pump connectors, and pressure transducers with respective portions of the cartridge.

In variations thereof, the thirty-second embodiments include ones in which the patient fill line and patient drain line join via a junction. In variations thereof, the thirty-second embodiments include ones in which the peritoneal dialysis admixer/cycler includes a cycler. In variations thereof, the thirty-second embodiments include ones in which the fluid source includes a connection platform with concentrates and a water source. In variations thereof, the thirty-second embodiments include ones in which the water source includes a purification plant with a pump upstream of the fluid inlet. In variations thereof, the thirty-second embodiments include ones in which the connection platform has a valve array to define flow paths selectively indicated by the controller to connect a selected one of the concentrates or water to the fluid inlet line. In variations thereof, the thirty-second embodiments include ones in which the connection platform has a controller that receives commands from the peritoneal dialysis admixer/cycler. In variations thereof, the thirty-second embodiments include ones in which the connection platform valve array includes a concentrate valve for each of multiple concentrates and a water valve for the water source. In variations thereof, the thirty-second embodiments include ones in which the water source includes a water purification plant with a pump and the water valve is located at an outlet of the water purification, an outlet of the water valve leading to a junction connects a common concentrate line with a pump to a fluid outlet that connects to the fluid inlet, the common concentrate line is connected to the concentrate containers. In variations thereof, the thirty-second embodiments include ones in which the peritoneal dialysis admixer/cycler mixes concentrate and water by commanding the connection platform to set the valve array to select each fluid for transport to the mixing container.

In variations thereof, the thirty-second embodiments include ones in which the peritoneal dialysis admixer/cycler uses contents of the mixing container to perform an automated peritoneal dialysis treatment. In variations thereof, the thirty-second embodiments include ones that include a flow diverter connected to the mixing container line and configured to cause ingoing fluid to enter mixing container at a different location or to be projected to a different location by a nozzle than where outgoing flow exits the mixing container. In variations thereof, the thirty-second embodiments include ones that include a header tube in the mixing container that is configured to distribute ingoing fluid from multiple openings in the mixing container. In variations thereof, the thirty-second embodiments include ones in which the valve network is positioned and held in a cartridge, the pumping portion is supported by a rigid manifold, the manifold is hollow and defining at least some of the junctions. In variations thereof, the thirty-second embodiments include ones in which the manifold has two separate chambers connected by a pumping tube segment. In variations thereof, the thirty-second embodiments include ones in which the manifold has two separate chambers connected for flow communication. In variations thereof, the thirty-second embodiments include ones in which the at least one in-line sterilizing filter includes two redundant sterilizing filters in series. In variations thereof, the thirty-second embodiments include ones in which the in-line sterilizing filter is testable by means of air pressure applied to an air-line attached thereto, the air-line is attached along at least a portion of the fluid inlet line. In variations thereof, the thirty-second embodiments include ones in which the fluid circuit contains no fluids. In variations thereof, the thirty-second embodiments include ones in which the concentrate containers have sufficient concentrate to form at least 35, 40, 50, 65, 80, or 100 liters of ready-to-use dialysate. In variations thereof, the thirty-second embodiments include ones in which the mixing container has a capacity of no more than 15, 20, 25, or 30 liters.

In any of the embodiments, any of the pumps may be, or include, any of a variety of types including peristaltic pumps, diaphragm pumps, screw pumps, gear pumps, centrifugal pumps, turbine pumps, syringe pumps, or piston pumps. The foregoing is a list of examples and is not intended to limit the scope of the present disclosure or the claims below.

In any of the embodiments, the containers of concentrate may be replaced with online sources of concentrate such as admixing plants in a large-scale installation that mixes component ingredients to form concentrates and provides them from a fixed connector. In any of the embodiments, other sources of fluids may be connected to the fluid flow director embodiments described herein. For example, cleaning fluids, reference testing fluids for calibrating the conductivity sensor or sensors, sample fluids, and fluids for testing membranes such as air. In any of the embodiments, such other fluids may flow through various parts of the fluid circuit including the drain as described with reference to other fluids.

As the term is used herein, "flow director" is a fluid circuit and associated actuators effective for selectively creating flow paths and moving fluids through the flow paths in order to connect fluid channels or vessels including those connected to sources and consumers, repositories, or other receiving elements. A "fluid circuit" is may be any line or branching element and may contain vessels, chambers, sensor portions, actuator portions, or any other type of fluid confining and controlling element.

Any embodiment which recites or shows tubes as portions of a fluid circuit, fluid channel, or other equivalent may have instead other types of fluid channel elements such as channels defined in a casting with a bonded film layer to close the channels, panels with welded patterns to form fluid channels, non-round ducts, or other types of elements. The disclosed tubes may be replaced with such alternative elements to form additional embodiments.

Any embodiment which identifies peritoneal dialysis fluid may be modified to form additional embodiments by replacing the components identified with that particular fluid with corresponding fluids to form other medicaments.

Any component or element identified herein as "disposable" may be sterile. Sterility may be readily provided and assured at a time of use, by providing components as disposable elements as is known in the relevant field of medical devices.

As used herein, "pre-connected" or "pre-connected" may refer to the integral combination of elements or to their connection in such a manner as to form a sterile boundary or permit the provision of a sterile boundary around their interior. For example, if a connection of connectors of two elements is made (i.e., they are pre-connected or pre-connected) and the connected elements are sterilized as a unit thereafter, the pre-connected or pre-connected elements may protect against the touch contamination that would be required if the corresponding connection were made in the field, for example. When elements are integral they may provide the same benefit. The terms "pre-connected" or "pre-connected" have the same meaning as used herein.

As the terms are used herein, electrolyte concentrate may include various ionic species as well as non-ionic species as required. As used herein, osmotic agent concentrate may include any osmotic agent such as glucose or dextrose and may include other species including ionic species that may be characterized by the term "electrolytes."

Any of the embodiments expressly limited to "peritoneal dialysis fluid" may be modified to form additional embodiments by substitution of the term "dialysate" and making appropriate substitutions for the constituents. Any embodiments limited to multiple concentrates, including two, may be changed to employ a single concentrate that is diluted to form a ready-to-use medicament.

Any of the valves or pumps recited herein may be substituted for any of a variety of types of flow directing and fluid conveying devices. For example a variety of pump and valve types are known and may be substituted for those described herein. Variations based on substitutions of these elements may be made to form additional embodiments.

As the term is used herein, "in-line" means that an element is in a flow path. For example, a flow channel with an in-line sterilizing filter is such that fluid flowing in the flow channel is filtered by the in-line filter.

A port is any transition for a fluid conveyance such as a channel, tube, integral connection, or connector. Any recitation of "port" may be replaced with the term "connector" to form variations of the disclosed embodiments.

As used herein, a window is any opening in a curved or flat element. A drain is any outlet to an external element and may include a storage vessel.

Any sterilizing filter may be embodied as a channel blocked by a microporous membrane. Such a microporous membrane may have pores whose maximum size is no greater than a minimum pathogen size. Known threshold pore sizes are, for example, 0.2 microns.

Any embodiment element identified with the term "daily" may be changed by substitution of other time intervals to form additional embodiments.

Integral or integrally attached refers to elements that are formed of a single piece or bonded together so as to create a single unit. Elements identified as integral may be changed to identify them as "connected" or "attached" to define additional embodiments.

As used herein, a "source" is any container or plant capable of supplying a recited fluid. A sink is any destination for a fluid such as a container, a consuming device, or a drain.

As user herein, a "line" is tube or other type of fluid channel. In any of the embodiments, lines may be tubes such as polymer tubing commonly used for medical disposable devices.

A "recess" is any concavity. A recess has two ends, an "access" which is the open end, and a "blind end," which is the closed end.

Any détente mechanism identified herein may be substituted with any type of frictional or interference-based mechanism for locking or restraining one element relative to another to form additional embodiments.

It will be appreciated that the modules, processes, systems, and sections described above can be implemented in hardware, hardware programmed by software, software instruction stored on a non-transitory computer readable medium, or a combination of the above. For example, a method for preparing a peritoneal dialysis treatment fluid and/or treating a patient can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C #.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control system, fluid handling systems, peritoneal dialysis treatment, such as a peritoneal dialysis treatment, and/or computer programming arts.

Moreover, embodiments of the disclosed method, system, and computer program product can be implemented in software executed on a programmed general-purpose computer, a special-purpose computer, a microprocessor, or the like.

Figure 12:
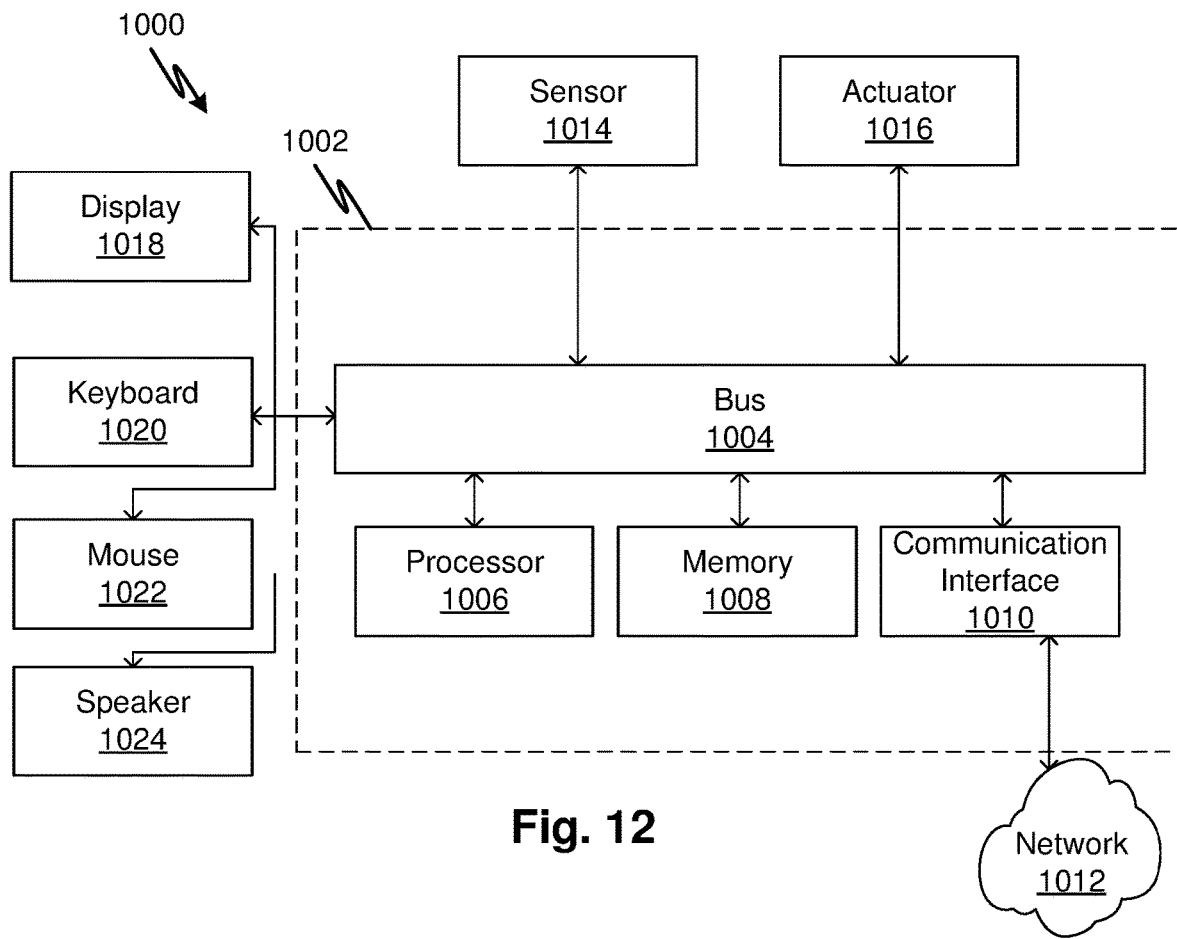
FIG. 12 shows a block diagram of an example computer system according to embodiments of the disclosed subject matter.

FIG. 12 shows a block diagram of an example computer system according to embodiments of the disclosed subject matter. In the embodiments where a controller is identified, the controller may take the form of the embodiment of FIG. 12. In various embodiments, all or parts of system 1000 may be included in a peritoneal dialysis treatment, such as a peritoneal dialysis treatment, device/system such as a renal replacement therapy system. In these embodiments, all or parts of system 1000 may provide the functionality of a controller of the peritoneal dialysis treatment, such as a peritoneal dialysis treatment, device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C #, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a peritoneal dialysis treatment for a patient and monitoring a patient during a peritoneal dialysis treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with a sensor 1014 and/or an actuator 1016, each providing respective functionality in accordance with various embodiments disclosed herein, for example, for measuring signals indicative of a patient/device condition and for controlling the operation of the device accordingly. For example, sensor 1014 may provide a signal indicative of a viscosity of a fluid in a fluid circuit in a renal replacement therapy device, and actuator 1016 may operate a pump that controls the flow of the fluid responsively to the signals of sensor 1014.

In any and all of the foregoing disposable fluid circuits, the components may be integrally-attached, meaning the components may be permanently bonded or otherwise locked together as delivered for use except for removable caps on inlets and outlets. In embodiments, only a single cap may be required to connect one or more concentrate inlets and a single cap may be required to connect a peritoneal dialysis catheter to the integrally-attached fill/drain line. This helps to ensure that a fluid circuit as delivered will not be contaminated by making multiple connections.

Note that in any of the embodiments that include pressure testing of a sterilizing filter, the pressure testing may be performed by applying pressurized air to one side of the filter membrane, fixing the pressurized volume, for example by halting a positive displacement pump, and sampling the pressure over time to acquire a pressure decay curve. Alternatively, a bubble point test may be employed. In yet further embodiments, any other known type of filter integrity test may be employed in addition or as an alternative.

Note that any of the controllers may be formed by multiple controllers or consolidated in a single device, such as an embedded system. The controllers may also include driver circuits and final-controllers, A/D circuits, and other elements to provide the recited functions according to methods and systems known in the art.

The term peritoneal dialysis treatment refers to an automated peritoneal dialysis APD that includes multiple fill and drain cycles. In embodiments, APD is performed at night over an 7-12 hour period. In embodiments, APD is performed during the day. A peritoneal dialysis treatment may include the generation and fill of a last fill that is different from the prescription of the multiple fill/drain cycles over the majority of the APD. The fill volumes for APD can be adjusted as can the dwell time (time between fill and drain) and the number of fill/drain cycles. In embodiments, fill volumes may be 500 ml., 1000 ml., 1500 ml., 2000 ml., 2500 ml., 3000 ml. The long term (or weekly) concentrate containers contain sufficient concentrate to make multiple mixing containers-full of ready-to-use peritoneal dialysis fluid. That is, the long term concentrate containers have sufficient concentrate for multiple APD treatments. In embodiments, the long term concentrate containers are exchanged every several days, for example, weekly. The short term fluid circuit with a pre-connected mixing container is used for a single treatment and after its mixing container contents are exhausted and a treatment is finished, it is removed. At the beginning of a next treatment, the fluid circuit with a new mixing container is connected to the peritoneal dialysis admixer/cycler. Since APD treatments are frequently done on a daily basis, the short term fluid circuit with the pre-connected mixing container may be referred conveniently as a daily fluid circuit. That is, the daily fluid circuit is used for a single peritoneal dialysis treatment and has a mixing container whose capacity is sufficient for a single APD but not more than one treatment. Note that in embodiments, an additional fill may be generated by a daily disposable component for use in continuous ambulatory peritoneal dialysis (CAPD) after an APD treatment, for example.

In any of the embodiments, the peritoneal dialysis solution admixer/cycler controller may be programmed to receive indications of several events as it sequences its operations. For example, a signal may be generated either automatically or by user input that one or both of the long term concentrate container is replaced. Such a signal may be generated automatically by an electrical switch (not shown) connected to a latch 286 (FIG. 2G) that indicates release or connection of a container. Containers may have optical bar codes, near field communication (NFC), radio frequency identification, smart chip or other indicators to identify them uniquely. Using the identification, the peritoneal dialysis solution admixer/cycler controller may store a history of the container (locally in a non-volatile data store or on a server) in order to determine how much capacity it has left. The peritoneal dialysis solution admixer/cycler controller may further determine if the identified concentrate is expired. The peritoneal dialysis solution admixer/cycler controller may output a message or alarm output on a user interface to indicate when one of these conditions is determined. At the beginning of the set up of a preparation of a batch of ready-to-use peritoneal dialysis fluid, the peritoneal dialysis solution admixer/cycler controller may determine whether the long term concentrate containers have capacity sufficient to make a batch of ready-to-use peritoneal dialysis fluid. The peritoneal dialysis solution admixer/cycler controller may output an indication that one or both long term concentrate containers need(s) to be changed responsively to the determination. This check may be done each time the admixing operation is initiated. The determination may be initiated when the daily fluid circuit is partially or fully connected to the peritoneal dialysis solution admixer/cycler. The determination may be initiated when an operator enters a command to being guided set up by prompting, by user input, the peritoneal dialysis solution admixer/cycler controller to begin outputting a set up script stored by the peritoneal dialysis solution admixer/cycler controller.

In any of the embodiments, the volume of the long term concentrate containers may be at least sufficient to form 35 liters of ready-to-use peritoneal dialysis solution. In any of the embodiments, the volume of the long term concentrate containers may be at least sufficient to form 40 liters of ready-to-use peritoneal dialysis solution. In any of the embodiments, the volume of the long term concentrate containers may be at least sufficient to form 50 liters of ready-to-use peritoneal dialysis solution. In any of the embodiments, the volume of the long term concentrate containers may be at least sufficient to form 65 liters of ready-to-use peritoneal dialysis solution. In any of the embodiments, the volume of the long term concentrate containers may be at least sufficient to form 80 liters of ready-to-use peritoneal dialysis solution. In any of the embodiments, the volume of the long term concentrate containers may be at least sufficient to form 100 liters of ready-to-use peritoneal dialysis solution.

In any of the embodiments, the volume of the long term concentrate containers may be at least sufficient to form ready-to-use peritoneal dialysis fluid for 50 fill volumes. In any of the embodiments, the volume of the long term concentrate containers may be at least sufficient to form ready-to-use peritoneal dialysis fluid for 100 fill volumes. In any of the embodiments, the volume of the long term concentrate containers may be at least sufficient to form ready-to-use peritoneal dialysis fluid for 125 fill volumes. In any of the embodiments, the volume of the long term concentrate containers may be at least sufficient to form ready-to-use peritoneal dialysis fluid for 150 fill volumes.

In embodiments disclosed, a testable sterilizing filter is used to filter concentrates and water flowing into a fluid circuit that is replaced daily. In embodiments, the sterilizing filter is integrally connected to the fluid circuit. In embodiments, the sterilizing filter is of a type to which air is applied to perform an integrity test, identified herein as a testable sterilizing filter. In such filters, fluid cannot be drawn through them by a pump because a negative pressure in the fluid channel will draw air into the fluid via a connected air-line. In embodiments disclosed herein, pumps may be arranged to ensure that a positive pressure is maintained on the liquid channel through the testable filter by providing a pump arranged upstream thereof to push fluid. For example, in the disclosed embodiments, a water pump is provided in the water source to push water through filtration stages that purify the water and on the concentrate side of a fluid inlet with the testable filter, upstream of the testable filter, a pump may be provided to draw concentrate and push it through the sterilizing filter. In some cases, it may be possible to draw a low viscosity fluid through a testable filter. Advantageously, however, in some of the disclosed, the viscous concentrates are pushed through the testable filter. Note that as the term is used herein, the term "in-line" does not exclude testable filters with an air port for pressure testing.

In any of the embodiments, including the claims, the fluid circuit may contain no fluids. For example, in claims in which a mixing container is recited, the limitation may be added to any given claim that the fluid circuit contains no fluids, including concentrate, unless explicitly recited that a fluid is contained, for example a concentrate.

Any of the containers recited in the specification or claims may be made of polymeric sheet material, expanded thermoplastic, or other materials. Polymeric sheet material such as used for medical fluid bags may be welded or adhesively bonded to define internal volumes. Containers of sheet material may be collapsed to occupy minimal space when empty. Many of the embodiments in which a fluid circuit is recited may be formed of tubing which is welded or adhesively bonded to the containers of sheet material. The various details of forming such containers and fluid circuits are well known in the art.

It is, thus, apparent that there is provided, in accordance with the present disclosure, methods, devices, and system for preparing fluids, managing fluids, sterilizing fluids, treating patients and other functions. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A system for preparing dialysis treatment fluid, comprising:
   an integrally interconnected fluid circuit including a mixing container pre-connected to the fluid circuit and configured to perform fluid mixing to prepare the dialysis treatment fluid, the mixing container and fluid circuit being sealed from an external environment, and the mixing container having a single mixing container line;
   a flow diverter disposed in the mixing container and connected to the single mixing container line, the flow diverter being configured to cause ingoing fluid to enter an interior of the mixing container at a first location in the interior of the mixing container that is different from a second location in the interior of the mixing container from which outgoing flow exits the interior of the mixing container;
   the fluid circuit including a valve network having junctions and valve portions that mechanically interface with valve actuators to define selectable flow paths in the valve network;
   the valve network further including a pumping portion and a fluid inlet line with a connector for connection to a fluid source, the fluid inlet line being fluidly connected to the mixing container by the pumping portion;
   the valve network being fluidly connecting the mixing container to the fluid inlet line; and
   the fluid inlet line having at least one in-line sterilizing filter including either one of a pair of spaced sterilizing filters and a testable sterilizing filter with an air-line, wherein
   the flow diverter includes
      an elongated tube that conveys ingoing fluid to the interior of the mixing container through a first opening at a distal end of the elongated tube,
      a second opening at a proximal end of the elongated tube; and
      a check valve that prevents fluid flow out of the second opening but permits the fluid flow into the elongated tube through the second opening.

2. The system of claim 1, further comprising a peritoneal dialysis admixer/cycler with a controller that controls a pumping actuator in engagement with the pumping portion, the controller controlling the pumping actuator to mix fluid in said mixing container by intermittently exchanging the fluid with a pump or an accumulator connected to the valve network.

* * * * *